(12) United States Patent
Altman et al.

(10) Patent No.: US 11,547,739 B2
(45) Date of Patent: Jan. 10, 2023

(54) PEPTIDES AND METHODS RELATED TO ICOS SIGNALING

(71) Applicant: La Jolla Institute for Allergy and Immunology, La Jolla, CA (US)

(72) Inventors: Amnon Altman, La Jolla, CA (US); Kok-Fai Kong, La Jolla, CA (US); Shane Crotty, La Jolla, CA (US)

(73) Assignee: La Jolla Institute for Allergy and Immunology, La Jolla, CA (US)

( * ) Notice: Subject to any disclaimer, the term of this patent is extended or adjusted under 35 U.S.C. 154(b) by 153 days.

(21) Appl. No.: 16/062,614

(22) PCT Filed: Dec. 16, 2016

(86) PCT No.: PCT/US2016/067375
§ 371 (c)(1),
(2) Date: Jun. 14, 2018

(87) PCT Pub. No.: WO2017/106784
PCT Pub. Date: Jun. 22, 2017

(65) Prior Publication Data
US 2018/0369326 A1    Dec. 27, 2018

Related U.S. Application Data

(60) Provisional application No. 62/267,954, filed on Dec. 16, 2015.

(51) Int. Cl.
| | | |
|---|---|---|
| *A61K 38/17* | (2006.01) |
| *C07K 7/06* | (2006.01) |
| *C12N 5/0783* | (2010.01) |
| *A61K 38/00* | (2006.01) |
| *C07K 14/47* | (2006.01) |
| *A61P 37/00* | (2006.01) |
| *A61P 3/00* | (2006.01) |
| *A61P 35/00* | (2006.01) |
| *A61K 31/7088* | (2006.01) |
| *C07K 14/705* | (2006.01) |
| *C12N 15/63* | (2006.01) |

(52) U.S. Cl.
CPC .......... *A61K 38/17* (2013.01); *A61K 31/7088* (2013.01); *A61P 3/00* (2018.01); *A61P 35/00* (2018.01); *A61P 37/00* (2018.01); *C07K 7/06* (2013.01); *C07K 14/47* (2013.01); *C07K 14/70503* (2013.01); *C12N 5/0636* (2013.01); *C12N 15/63* (2013.01); *A61K 38/00* (2013.01); *C07K 2319/03* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 8,840,889 B2 * | 9/2014 | Chen ................ | C07K 14/70521 |
| | | | 424/139.1 |
| 9,193,789 B2 | 11/2015 | Coyle et al. | |
| 9,597,274 B2 * | 3/2017 | Idkowiak-Baldys ....................... | |
| | | | A61K 8/4926 |

FOREIGN PATENT DOCUMENTS

WO    WO-2013/126733 A1    8/2013

OTHER PUBLICATIONS

Hedl et al. 'Pattern Recognition Receptor Signaling in Human Dendritic Cells is Enhanced by ICOS Ligand and Modulated by the Crohn's Disease ICOSLG Risk Allele.' Immunity 40, 734-746, May 15, 2014.*
R & D Catalog No. 9945-CS Aug. 29, 2018.*
Deng et al. 'Expression of recombinant human ICOS and in vitro characterization of its bioactivity on B lymphocytes.' Sheng Wu Hua Xue Yu Sheng Wu Wu Li Xue Bao (Shanghai) Jul. 2003;35(7):601-5.*
Deng et al. 'Expression of recombinant human ICOS and in vitro characterization of its bioactivity on B lymphocytes.' Acta Biochimica et Biophysica 35(7):601-605, 2003.*
Database GenBank CAD57066.1, Nov. 21, 2002.
Lu, L-F. et al. (2009) "MicroRNA in the immune system, microRNA as an immune system," Immunology 127:291-298.
International Search Report and Written Opinion (ISA/RU) for International Application No. PCT/US2016/067375, dated Jun. 1, 2017.

* cited by examiner

*Primary Examiner* — Nora M Rooney
(74) *Attorney, Agent, or Firm* — Foley & Lardner LLP

(57) ABSTRACT

The present disclosure relates to methods and compositions useful for initiating and propagating ICOS-mediated signaling. In particular, the present disclosure provides three peptide motifs which promote ICOS binding and whose ablation leads to modulated ICOS signaling and modulated signaling mediated by TBK1, IRF4, IKKβ, or TBKBP1. The binding of these peptide motifs or the addition of such motifs as co-stimulatory agents leads to modulated immune responses, and provides new and unexpected therapies for neurodegenerative, autoimmune, metabolic, cancer inflammatory, or immunodeficiency conditions, diseases, or disorders.

6 Claims, 21 Drawing Sheets
Specification includes a Sequence Listing.

d e

SEQUENCE LISTING

```
<160> NUMBER OF SEQ ID NOS: 93

<210> SEQ ID NO 1
<211> LENGTH: 199
<212> TYPE: PRT
<213> ORGANISM: Homo sapiens

<400> SEQUENCE: 1

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Phe Lys Val Thr Leu Thr Gly Gly Tyr Leu
            115                 120                 125

His Ile Tyr Glu Ser Gln Leu Cys Cys Gln Leu Lys Phe Trp Leu Pro
        130                 135                 140

Ile Gly Cys Ala Ala Phe Val Val Val Cys Ile Leu Gly Cys Ile Leu
145                 150                 155                 160
```

```
Ile Cys Trp Leu Thr Lys Lys Lys Tyr Ser Ser Val His Asp Pro
            165                 170                 175

Asn Gly Glu Tyr Met Phe Met Arg Ala Val Asn Thr Ala Lys Lys Ser
        180                 185                 190

Arg Leu Thr Asp Val Thr Leu
        195

<210> SEQ ID NO 2
<211> LENGTH: 199
<212> TYPE: PRT
<213> ORGANISM: Pan troglodytes

<400> SEQUENCE: 2

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
            35                  40                  45

Gln Gln Phe Lys Met Gln Leu Leu Lys Gly Gly Gln Ile Leu Cys Asp
        50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp Arg Ser His Ala Asn Tyr Tyr Phe Cys Asn Leu Ser
            100                 105                 110

Ile Phe Asp Pro Pro Phe Lys Val Thr Leu Thr Gly Gly Tyr Leu
            115                 120                 125

His Ile Tyr Glu Ser Gln Leu Cys Cys Gln Leu Lys Phe Trp Leu Pro
        130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
            165                 170                 175

Asn Gly Glu Tyr Met Phe Met Arg Ala Val Asn Thr Ala Lys Lys Ser
        180                 185                 190

Arg Leu Thr Asp Val Thr Leu
        195

<210> SEQ ID NO 3
<211> LENGTH: 199
<212> TYPE: PRT
<213> ORGANISM: Pongo Abelii

<400> SEQUENCE: 3

Met Lys Ser Arg Leu Trp Tyr Leu Phe Leu Phe Cys Leu His Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
            35                  40                  45

Gln Gln Phe Lys Met Gln Leu Leu Lys Gly Gly Gln Ile Leu Cys Asp
        50                  55                  60

Leu Thr Lys Thr Lys Gly Ser Gly Asn Thr Val Ser Ile Lys Arg Leu
65                  70                  75                  80
```

```
Lys Phe Cys His Ser Gln Leu Ser Asn Asn Ser Val Ser Phe Phe Leu
                 85                  90                  95

Tyr Asn Leu Asp Arg Ser His Ala Asn Tyr Tyr Phe Cys Asn Leu Ser
            100                 105                 110

Ile Phe Asp Pro Pro Phe Lys Val Thr Leu Thr Gly Gly Tyr Leu
            115                 120                 125

His Ile Tyr Glu Ser Gln Leu Cys Cys Gln Leu Lys Phe Trp Leu Pro
130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Val His Asp Pro
                165                 170                 175

Asn Gly Glu Tyr Met Phe Met Arg Ala Val Asn Thr Ala Lys Lys Ser
                180                 185                 190

Lys Leu Thr Asp Val Thr Ile
                195

<210> SEQ ID NO 4
<211> LENGTH: 199
<212> TYPE: PRT
<213> ORGANISM: Macaca mulatta

<400> SEQUENCE: 4

Met Lys Ser Gly Leu Trp Tyr Phe Phe Leu Phe Cys Leu His Met Lys
1               5                   10                  15

Val Leu Thr Gly Glu Ile Asn Gly Ser Ala Asn Tyr Glu Met Phe Ile
                20                  25                  30

Phe His Asn Gly Gly Val Gln Ile Leu Cys Lys Tyr Pro Asp Ile Val
                35                  40                  45

Gln Gln Phe Lys Met Gln Leu Leu Lys Gly Gly Gln Ile Leu Cys Asp
            50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp Arg Ser His Ala Asn Tyr Tyr Phe Cys Asn Leu Ser
            100                 105                 110

Ile Phe Asp Pro Pro Phe Lys Val Thr Leu Thr Gly Gly Tyr Leu
            115                 120                 125

His Ile Tyr Glu Ser Gln Leu Cys Cys Gln Leu Lys Phe Trp Leu Pro
130                 135                 140

Ile Gly Cys Ala Thr Phe Val Val Cys Ile Phe Gly Cys Ile Leu
145                 150                 155                 160

Ile Cys Trp Leu Thr Lys Lys Lys Tyr Ser Ser Thr Val His Asp Pro
                165                 170                 175

Asn Gly Glu Tyr Met Phe Met Arg Ala Val Asn Thr Ala Lys Lys Ser
                180                 185                 190

Arg Leu Thr Asp Val Thr Val
                195

<210> SEQ ID NO 5
<211> LENGTH: 208
<212> TYPE: PRT
<213> ORGANISM: Canis familiaris
```

```
<400> SEQUENCE: 5

Met Lys Ser Asp Leu Trp Tyr Phe Leu Leu Phe Cys Phe Gln Val Glu
1               5                   10                  15

Ala Leu Thr Gly Glu Ile Asn Asp Ser Thr Lys Ser Glu Met Phe Thr
            20                  25                  30

Phe His Asp Gly Gly Val Gln Ile Leu Cys Lys Phe Asn Ala Ile Val
        35                  40                  45

Ser Gln Tyr Lys Met Glu Leu Leu Lys Gly Thr Glu Val Leu Cys Asp
    50                  55                  60

Leu Thr Thr Thr Lys Glu Asn Gly Asn Thr Val Ser Lys Asn Pro Lys
65                  70                  75                  80

Phe Cys Gln Ser Gln Ser Ser Asp Gly Val Ser Phe Phe Leu Tyr
            85                  90                  95

Asn Leu Asp Ser Ser His Ala Ser Tyr Tyr Ala Cys Gln Leu Ser Ile
            100                 105                 110

Phe Asp Pro Pro Phe Gln Arg Lys Asn Ile Ser Arg Glu Tyr Leu
        115                 120                 125

Asn Val Tyr Glu Ser Gln Thr Cys Cys Gln Leu Lys Phe Trp Leu Pro
130                 135                 140

Ile Gly Cys Ala Ala Phe Val Val Tyr Ile Phe Gly Cys Ile Phe
145                 150                 155                 160

Leu Cys Trp Leu Thr Lys Lys Lys Tyr Arg Ser Ser Val His Asp Pro
            165                 170                 175

Asn Ser Glu Tyr Met Phe Met Ala Ala Val Asn Thr Ala Lys Lys Pro
            180                 185                 190

Gly Leu Thr Gly Val Thr His Asn Leu Glu Leu Cys Gly Thr Gln Ala
            195                 200                 205

<210> SEQ ID NO 6
<211> LENGTH: 180
<212> TYPE: PRT
<213> ORGANISM: Felis catus

<400> SEQUENCE: 6

Met Phe Thr Phe His Asp Gly Gly Ile Gln Ile Ser Cys Lys Phe Ser
1               5                   10                  15

Glu Ile Ala Leu Gln Phe Lys Met Lys Leu Leu Lys Gly Thr Glu Val
            20                  25                  30

Leu Cys Asp Leu Thr Lys Thr Lys Glu Ser Gly Asn Thr Val Ser Ile
        35                  40                  45

Lys Asn Leu Lys Phe Cys Gln Thr Gln Leu Phe Asn Asp Ser Val Ser
    50                  55                  60

Phe Phe Leu Tyr Asn Leu Asp Ser Ser His Ala Ser Tyr Tyr Thr Cys
65                  70                  75                  80

Glu Leu Ser Ile Phe Asp Pro Pro Phe Gln Lys Lys Asn Ile Ser
            85                  90                  95

Arg Glu Tyr Leu Asn Ile Tyr Glu Ser Gln Ile Cys Cys Gln Leu Lys
            100                 105                 110

Phe Trp Leu Pro Ile Gly Cys Ser Ala Phe Val Val Tyr Ile Phe
        115                 120                 125

Gly Cys Val Phe Leu Cys Trp Leu Thr Lys Lys Lys Tyr Arg Ser Ser
    130                 135                 140

Gly His Asp Pro Asn Ser Glu Tyr Met Phe Met Ala Ala Val Asn Thr
145                 150                 155                 160
```

```
Ala Lys Lys Pro Gly Leu Thr Gly Val Thr His Asn Leu Glu Leu Cys
                165                 170                 175

Gly Thr Gln Ala
            180

<210> SEQ ID NO 7
<211> LENGTH: 209
<212> TYPE: PRT
<213> ORGANISM: Bos taurus

<400> SEQUENCE: 7

Met Lys Ser Asp Leu Arg Tyr Phe Phe Leu Phe Cys Ile Gln Val Glu
1               5                   10                  15

Ile Leu Ala Gly Glu Phe Asn Asp Ser Ala Ala Ser Glu Met Phe Ile
            20                  25                  30

Phe His Asn Gly Gly Val Gln Ile Leu Cys Lys Tyr Pro Asp Thr Val
            35                  40                  45

Arg Gln Phe Lys Met Gln Leu Leu Lys Gly Asp Asn Val Leu Cys Asp
50                  55                  60

Leu Thr Lys Thr Lys Glu Asn Glu Asp Thr Val Ser Ile Arg Asn Leu
65                  70                  75                  80

Asn Val Cys Lys Phe Gln Leu Ser Asn Ser Val Ser Phe Phe Leu
                85                  90                  95

Tyr Asn Leu Asp Ser Ser Tyr Ala Ser Tyr Tyr Ile Cys Lys Leu Ser
                100                 105                 110

Ile Phe Asp Pro Pro Phe Gln Val Asp Ile Leu Ser Arg Glu Tyr
            115                 120                 125

Leu Asn Ile Tyr Glu Ser Glu Leu Cys Cys Gln Leu Lys Phe Trp Leu
130                 135                 140

Pro Ile Gly Cys Ala Ala Phe Val Thr Val Cys Val Phe Gly Cys Val
145                 150                 155                 160

Leu Met Tyr Trp Leu Thr Lys Lys Tyr Pro Thr Ser Val His Asp
                165                 170                 175

Pro Asn Ser Glu Tyr Met Phe Met Ala Ala Val Asn Thr Ala Lys Lys
            180                 185                 190

Pro Ala Pro Thr Asp Val Thr Arg Asn Leu Glu Leu Pro Gly Thr Gln
            195                 200                 205

Ala

<210> SEQ ID NO 8
<211> LENGTH: 209
<212> TYPE: PRT
<213> ORGANISM: Ailuropoda melanoleuca

<400> SEQUENCE: 8

Met Lys Ser Asp Leu Trp Tyr Phe Leu Leu Phe Cys Phe Gln Val Glu
1               5                   10                  15

Ala Leu Thr Gly Glu Ile Asn Asp Ser Ala Lys Ser Glu Met Phe Thr
            20                  25                  30

Phe His Asp Gly Gly Val Gln Ile Leu Cys Lys Phe Ser Asp Thr Val
            35                  40                  45

Trp Gln Phe Lys Met Lys Leu Trp Lys Gly Thr Glu Val Leu Cys Asp
50                  55                  60

Leu Thr Lys Thr Lys Glu Ser Gly Asn Thr Glu Ser Ile Lys Asn Pro
65                  70                  75                  80
```

Lys Ser Cys Gln Ser Gln Leu Ser Asn Asp Gly Val Ser Phe Phe Leu
            85                  90                  95

Asn Asn Leu Asp Ser Ser His Ala Ser Tyr Tyr Ala Cys Glu Leu Ser
        100                 105                 110

Ile Phe Asp Pro Pro Phe Gln Lys Lys Asn Ile Ser Arg Glu Tyr
        115                 120                 125

Leu Asn Val Tyr Glu Ser Gln Thr Cys Cys Gln Leu Lys Phe Trp Leu
        130                 135                 140

Pro Ile Gly Cys Ala Ala Phe Val Val Tyr Ile Phe Gly Cys Val
145                 150                 155                 160

Phe Leu Cys Trp Leu Thr Lys Lys Tyr Arg Ser Ser Val His Asp
                165                 170                 175

Pro Asn Ser Glu Tyr Met Phe Met Ala Ala Val Asn Thr Ala Lys Lys
        180                 185                 190

Pro Gly Val Thr Gly Val Thr His Asn Leu Glu Leu Cys Gly Thr Gln
        195                 200                 205

Ala

<210> SEQ ID NO 9
<211> LENGTH: 200
<212> TYPE: PRT
<213> ORGANISM: Mus musculus

<400> SEQUENCE: 9

Met Lys Pro Tyr Phe Cys Arg Val Phe Val Phe Cys Phe Leu Ile Arg
1               5                   10                  15

Leu Leu Thr Gly Glu Ile Asn Gly Ser Ala Asp His Arg Met Phe Ser
            20                  25                  30

Phe His Asn Gly Gly Val Gln Ile Ser Cys Lys Tyr Pro Glu Thr Val
        35                  40                  45

Gln Gln Leu Lys Met Arg Leu Phe Arg Glu Arg Glu Val Leu Cys Glu
    50                  55                  60

Leu Thr Lys Thr Lys Gly Ser Gly Asn Ala Val Ser Ile Lys Asn Pro
65                  70                  75                  80

Met Leu Cys Leu Tyr His Leu Ser Asn Asn Ser Val Ser Phe Phe Leu
                85                  90                  95

Asn Asn Pro Asp Ser Ser Gln Gly Ser Tyr Tyr Phe Cys Ser Leu Ser
            100                 105                 110

Ile Phe Asp Pro Pro Phe Gln Glu Arg Asn Leu Ser Gly Gly Tyr
        115                 120                 125

Leu His Ile Tyr Glu Ser Gln Leu Cys Cys Gln Leu Lys Leu Trp Leu
    130                 135                 140

Pro Val Gly Cys Ala Ala Phe Val Val Val Leu Leu Phe Gly Cys Ile
145                 150                 155                 160

Leu Ile Ile Trp Phe Ser Lys Lys Lys Tyr Gly Ser Ser Val His Asp
                165                 170                 175

Pro Asn Ser Glu Tyr Met Phe Met Ala Ala Val Asn Thr Asn Lys Lys
            180                 185                 190

Ser Arg Leu Ala Gly Val Thr Ser
        195                 200

<210> SEQ ID NO 10
<211> LENGTH: 200
<212> TYPE: PRT
<213> ORGANISM: Rattus norvegicus

<400> SEQUENCE: 10

```
Met Lys Pro Tyr Phe Ser Cys Val Phe Val Phe Cys Phe Leu Ile Lys
1               5                   10                  15

Leu Leu Thr Gly Glu Leu Asn Asp Leu Ala Asn His Arg Met Phe Ser
            20                  25                  30

Phe His Asp Gly Gly Val Gln Ile Ser Cys Asn Tyr Pro Glu Thr Val
        35                  40                  45

Gln Gln Leu Lys Met Gln Leu Phe Lys Asp Arg Glu Val Leu Cys Asp
    50                  55                  60

Leu Thr Lys Thr Lys Gly Ser Gly Asn Thr Val Ser Ile Lys Asn Pro
65                  70                  75                  80

Met Ser Cys Pro Tyr Gln Leu Ser Asn Asn Ser Val Ser Phe Phe Leu
                85                  90                  95

Asp Asn Ala Asp Ser Ser Gln Gly Ser Tyr Phe Leu Cys Ser Leu Ser
            100                 105                 110

Ile Phe Asp Pro Pro Phe Gln Glu Lys Asn Leu Ser Gly Gly Tyr
        115                 120                 125

Leu Leu Ile Tyr Glu Ser Gln Leu Cys Cys Gln Leu Lys Leu Trp Leu
    130                 135                 140

Pro Val Gly Cys Ala Ala Phe Val Ala Ala Leu Leu Phe Gly Cys Ile
145                 150                 155                 160

Phe Ile Val Trp Phe Ala Lys Lys Lys Tyr Arg Ser Ser Val His Asp
                165                 170                 175

Pro Asn Ser Glu Tyr Met Phe Met Ala Ala Val Asn Thr Asn Lys Lys
            180                 185                 190

Ser Arg Leu Ala Gly Met Thr Ser
        195                 200
```

<210> SEQ ID NO 11
<211> LENGTH: 203
<212> TYPE: PRT
<213> ORGANISM: Taeniopygia guttata

<400> SEQUENCE: 11

```
Met Lys Ser Asp Leu Trp Tyr Phe Phe Leu Phe Cys Phe Gln Val Glu
1               5                   10                  15

Val Leu Thr Gly Glu Ile Asn Asp Ser Ala Lys Tyr Glu Met Phe Thr
            20                  25                  30

Phe His Asn Gly Gly Val Gln Ile Val Cys Lys Tyr Pro Glu Ile Val
        35                  40                  45

Gln Gln Phe Lys Met Gln Leu Leu Lys Gly Glu Gln Val Leu Cys Asp
    50                  55                  60

Leu Arg Gln Thr Lys Glu Ser Gly Asn Thr Val Ser Ile Lys Ala Leu
65                  70                  75                  80

Lys Phe Cys Gln Tyr Gln Leu Phe Asn Asn Ser Val Ser Phe Phe Leu
                85                  90                  95

Tyr Asn Leu Asp Ser Ser His Ala Ser Tyr Tyr Phe Cys Lys Leu Ser
            100                 105                 110

Thr Phe Asp Pro Pro Phe Gln Val Glu Ile Leu Arg Gly Glu Tyr
        115                 120                 125

Leu His Ile Tyr Glu Ser Gln Leu Cys Cys Gln Leu Lys Phe Trp Leu
    130                 135                 140

Pro Ile Gly Cys Ala Ala Phe Ala Val Val Tyr Ile Phe Gly Cys Val
145                 150                 155                 160
```

```
Phe Ile Phe Trp Leu Thr Lys Lys Lys Tyr Gln Ser Ser Val His Asp
                165                 170                 175

Pro Asn Ser Glu Tyr Met Phe Met Ala Ala Val Asn Thr Ala Lys Lys
            180                 185                 190

Pro Thr Pro Pro Glu Leu Ser Gly Thr Arg Ala
        195                 200

<210> SEQ ID NO 12
<211> LENGTH: 360
<212> TYPE: PRT
<213> ORGANISM: Oryctolagus cuniculus

<400> SEQUENCE: 12

Met Lys Ser Gly Ile Leu Ala Cys Leu Ile Phe Phe Gln Phe Glu Ala
1               5                   10                  15

Leu Ser Ala Arg Asn Arg His Arg Glu Arg Lys Lys Gln Lys Ser Pro
            20                  25                  30

Gln Lys Ala Ala Glu Thr Thr Ala Lys Met Gly Gly Glu Glu Ala Thr
        35                  40                  45

Arg Arg Lys Glu Gly Val Glu Ala Trp Arg Ala Ser Glu Glu Pro Cys
    50                  55                  60

Trp Glu Gly Gly Arg Asn Leu Arg Ser Arg Phe Arg Lys Lys Ile Gln
65                  70                  75                  80

Pro His Ser His Ile Pro Phe Arg Lys Lys Thr Asp Ala Glu Glu Val
                85                  90                  95

Gly Met Ser Asn Pro Gly Ala Ala Ser Phe Met Thr Gln Ile Leu Trp
            100                 105                 110

Leu Thr Gln Ser His Leu Ser Lys Ile Ala Leu Ile Trp Leu Val Ile
        115                 120                 125

Ser Ser Ser Asp Thr Lys Ile Ile Cys Phe Phe Ile Ala Ser Leu Arg
    130                 135                 140

Lys Gly Ala Arg Thr Leu Asn Ala Ile Thr Phe Val Leu Gly Leu Val
145                 150                 155                 160

Asp Pro Leu Pro Ser Gln Glu Thr Lys Pro Cys Glu Glu Lys Leu Gly
                165                 170                 175

Gln Thr Ile Glu Glu Ser Asn Ala Thr Ala His Gln Lys Met Met Ala
            180                 185                 190

Phe His Asn Gly Val Val Lys Val Thr Cys His Tyr Pro Arg Ser Ala
        195                 200                 205

Arg Asp Phe Thr Met Gln Leu Leu Lys Gly Thr Met Arg Gln Lys Val
    210                 215                 220

Cys Glu Leu Ile Arg Asp Lys Asp Ile Thr Asn Thr Thr Gln Lys
225                 230                 235                 240

Glu Leu Ile Tyr Cys Gln Pro Asp Leu Ser Asn Asp Ser Val Ile Phe
                245                 250                 255

Thr Leu Ser Asn Leu Asp Ile Arg His Ala Asp Tyr Tyr Phe Cys Ser
            260                 265                 270

Leu Glu Val Ser Phe Pro Pro Tyr Gln Asn Cys Thr Pro Asp Glu
        275                 280                 285

Ala Tyr Leu Tyr Val Tyr Glu Ser Lys Phe Cys Ser Lys Leu Thr Phe
    290                 295                 300

Trp Leu Pro Val Gly Leu Ala Val Phe Ser Met Leu Ser Cys Ile Cys
305                 310                 315                 320

Cys Ile Leu Ala Phe Trp Leu Arg Asn Lys Ser Asn Gln Cys Pro Ser
                325                 330                 335
```

```
Ser Leu His Glu Pro Asn Ser Glu Tyr Met Pro Met Ala Ala Val Thr
            340                 345                 350

Ala Ala Lys Lys Ser Gly Phe Arg
            355                 360

<210> SEQ ID NO 13
<211> LENGTH: 229
<212> TYPE: PRT
<213> ORGANISM: Meleagris gallopavo

<400> SEQUENCE: 13

Met Phe Thr Ala Asp Arg Lys Leu Met Pro Leu Cys Gln Ala Ser Met
1               5                   10                  15

Lys Ser Val Ala Val Thr Phe Tyr Leu Phe Cys Phe Gln Phe Glu Ala
            20                  25                  30

Leu Cys Gly Ala Asp Thr Cys Ser Ser Arg Leu Cys Lys Asn Ile Asp
        35                  40                  45

Lys Leu Gln Val Ser Asp Pro Gln Gly Ile Val Lys Phe Glu Asn Gly
    50                  55                  60

Asn Phe Lys Leu Ile Phe Gln Asn Pro Lys Asn Val Ser Glu Phe Ser
65                  70                  75                  80

Met Thr Leu Leu Lys Gly His Glu Arg Lys Ala Ile Cys Ala Leu His
                85                  90                  95

Val Ser Lys Asn Lys Ala Val Pro Glu Ser Asn Val Thr Tyr Cys Gln
            100                 105                 110

Ala Glu His Ser Asn Thr Ser Thr Thr Phe Ile Leu Thr Asn Leu Asp
        115                 120                 125

Arg Lys His Ile Asp Thr Tyr Thr Cys Cys Leu Glu Ser Leu Leu Pro
    130                 135                 140

Pro Pro Tyr Ile Asp Cys His Leu Lys Glu Thr Tyr Leu Tyr Ile Gln
145                 150                 155                 160

Asp Lys Glu Asp Cys Phe Ser Gln Gly Ile Met Ser Trp Ile Ile Ile
                165                 170                 175

Gly Leu Ile Ala Phe Ala Leu Ile Ser Cys Val Cys Val Ile Ala
            180                 185                 190

Cys Ser Leu Arg Asn Lys Asn Gln Gln Cys Glu Ser Ser His Glu
        195                 200                 205

Tyr Asn Ser Glu Tyr Met Pro Met Ala Ala Val Asn Ala Ala Lys Asn
    210                 215                 220

Gln Glu Ser Glu Val
225

<210> SEQ ID NO 14
<211> LENGTH: 212
<212> TYPE: PRT
<213> ORGANISM: Gallus gallus

<400> SEQUENCE: 14

Met Lys Thr Val Ala Val Thr Phe Cys Leu Leu Cys Phe Gln Phe Glu
1               5                   10                  15

Ala Leu Cys Gly Val Asp Thr Cys Ser Ser Arg Leu Cys Lys Asn Ile
            20                  25                  30

Asp Lys Leu Gln Val Ser Asp Pro Gln Gly Ile Val Glu Phe Glu Asn
        35                  40                  45

Gly Asn Phe Lys Leu Ile Phe Gln Asn Pro Lys Asn Val Asn Glu Phe
    50                  55                  60
```

```
Ser Met Thr Leu Leu Lys Gly Arg Glu Arg Lys Ala Ile Cys Ala Leu
 65                  70                  75                  80

His Met Asn Asn Lys Lys Ala Val Pro Glu Ser Asn Val Thr Tyr Cys
                 85                  90                  95

Gln Ala Glu His Ser Asp Thr Ser Thr Thr Phe Ile Leu Thr Asn Leu
            100                 105                 110

Asp Arg Lys His Ile Asp Thr Tyr Thr Cys Cys Leu Glu Ser Leu Leu
        115                 120                 125

Pro Pro Pro Tyr Ile His Cys His Leu Lys Glu Thr Tyr Leu Tyr Ile
130                 135                 140

Gln Asp Lys Glu Asp Cys Ser Ser Gln Gly Ile Met Ser Trp Ile Ile
145                 150                 155                 160

Ile Gly Leu Ile Ala Phe Ala Leu Ile Phe Cys Val Cys Phe Val Val
                165                 170                 175

Ala Cys His Leu Arg Asn Lys Asn Gln Gln Cys Glu Ser Asn Ser His
            180                 185                 190

Glu Tyr Asn Ser Glu Tyr Met Pro Met Ala Ala Val Asn Ala Ala Lys
        195                 200                 205

Lys Pro Arg Ile
210

<210> SEQ ID NO 15
<211> LENGTH: 212
<212> TYPE: PRT
<213> ORGANISM: Anas platyrhynchos

<400> SEQUENCE: 15

Met Lys Ser Val Ala Val Thr Leu Cys Leu Leu Cys Phe Gln Phe Gly
  1               5                  10                  15

Ala Leu Cys Gly Ala Asp Thr Cys Ser Ser Arg Pro Cys Lys Asn Ile
                 20                  25                  30

Asp Gln Leu His Val Ser Asp Ser Gln Val Met Val Glu Phe Asn Ser
            35                  40                  45

Gly Thr Phe Lys Phe Ile Phe His Asn Pro Lys Asn Val Ser Glu Phe
        50                  55                  60

Ser Met Thr Leu Phe Lys Gly His Glu Lys Lys Glu Ile Cys Ala Leu
 65                  70                  75                  80

His Val Ser Lys Glu Lys Ala Ile Pro Lys Ser Asn Val Thr Tyr Cys
                 85                  90                  95

Gln Ala Glu His Ser Asn Thr Ser Thr Thr Phe Ile Leu Thr Asn Leu
            100                 105                 110

Glu Arg Lys His Ile Asp Thr Tyr Thr Tyr Cys Leu Glu Met Phe Leu
        115                 120                 125

Pro Pro Pro Tyr Ile Asp Cys Arg Leu Lys Glu Thr Tyr Leu Tyr Ile
130                 135                 140

Gln Asp Lys Glu Asp Cys Ile Ser Leu Gly Leu Met Thr Trp Val Thr
145                 150                 155                 160

Ile Gly Leu Ile Val Phe Ala Met Ile Ser Cys Val Cys Val Ala
                165                 170                 175

Ala Cys Arg Leu Arg Asn Lys Asn Gln Gln Cys Glu Ser Asn Ser His
            180                 185                 190

Glu Tyr Asn Ser Glu Tyr Met Pro Met Ala Ala Val Asn Ala Ala Lys
        195                 200                 205

Lys Thr Arg Ile
210
```

```
<210> SEQ ID NO 16
<211> LENGTH: 211
<212> TYPE: PRT
<213> ORGANISM: Taeniopygia guttata

<400> SEQUENCE: 16

Met Lys Ala Val Ala Val Thr Phe Cys Val Leu Cys Phe Gln Phe Glu
1               5                   10                  15

Ala Leu Tyr Gly Val Asp Gly Cys Ser Ser Ala Cys Lys Asn Ile
            20                  25                  30

Asp Gln Ala His Val Ser Asp Gly Glu Val Met Val Glu Phe Glu Asn
                35                  40                  45

Gly Asn Phe His Phe Thr Phe Pro Asn Pro Lys Ser Val Ser Glu Phe
        50                  55                  60

Ser Met Thr Leu Phe Lys Gly Arg Glu Lys Lys Glu Ile Cys Ala Ile
65                  70                  75                  80

His Leu Ser Lys Glu Arg Val Ile Ser Lys Ser Asn Val Thr Tyr Cys
                85                  90                  95

Gln Thr Gln Asn Ser Ser Ser Thr Ile Phe Ile Leu Lys Asn Leu
            100                 105                 110

Gly Lys Lys His Ile Asp Val Tyr Thr Cys Cys Leu Glu Ile Phe Leu
        115                 120                 125

Pro Pro Pro Tyr Ile Glu Arg Cys Leu Lys Glu Thr Phe Leu Tyr Ile
130                 135                 140

Gln Asp Lys Glu Asp Cys Phe Ser Leu Gly Leu Met Leu Trp Ile Ile
145                 150                 155                 160

Ile Gly Val Ile Ile Phe Ala Ile Ser Cys Val Cys Val Val Ala
            165                 170                 175

Cys Cys Leu Arg Asn Lys Asn Gln Lys Cys Glu Ser Asn Ser His Glu
                180                 185                 190

Tyr Asn Ser Glu Tyr Met Pro Met Ala Ala Val Asn Ala Ala Lys Lys
            195                 200                 205

Pro Arg Ile
    210

<210> SEQ ID NO 17
<211> LENGTH: 210
<212> TYPE: PRT
<213> ORGANISM: Xenopus Tropicalis

<400> SEQUENCE: 17

Met Asn Val Asn Leu Thr Gly Phe Pro Leu Phe Ile Leu Leu Val Leu
1               5                   10                  15

His Ala Gln Leu Ser Lys Ser Tyr Pro Lys Val Val Ile Ala Ser Gln
            20                  25                  30

Asp Gly Glu Pro Cys Leu Leu Cys His His Val Pro Ser Thr Asp Ser
        35                  40                  45

Lys Phe Asn Leu Thr Leu Met Arg Gly Asn Lys Gln Glu Val Cys
    50                  55                  60

Met Val Tyr Thr Asp Gly Lys Asn Thr Ser Phe Tyr Ser Trp Asn Asp
65                  70                  75                  80

Asn Pro Lys Cys Asn Trp Thr Lys Ser Asn Asp Ser Ser Ile Ser Phe
                85                  90                  95

Thr Leu Ser Asn Phe Asp Ile Lys His Thr Asp Asn Tyr Thr Cys Glu
            100                 105                 110
```

```
Ile Arg Ile Phe Tyr Pro Pro Pro Phe Arg Ser Ile Ile Ile Asn Glu
        115                 120                 125

Thr Tyr Val Tyr Ile His Asp Leu Gln Gln Cys Gly Ser Gly Met Gln
    130                 135                 140

Glu Phe Ile Ile Trp Ile Leu Thr Gly Leu Ala Val Phe Leu Phe Leu
145                 150                 155                 160

Cys Cys Ile Phe Thr Phe Cys Leu Trp Ile Gln Asn Arg Phe Arg Arg
                165                 170                 175

Lys Cys Leu Ser Gln Gly Asn Thr Gln Asn Asn Glu Cys Asn Ser Glu
            180                 185                 190

Tyr Met Pro Met Ala Ser Val Asn Pro Ala Lys Arg Pro Val Ile Pro
        195                 200                 205

Arg Leu
    210

<210> SEQ ID NO 18
<211> LENGTH: 10
<212> TYPE: PRT
<213> ORGANISM: Artificial Sequence
<220> FEATURE:
<223> OTHER INFORMATION: Proximal Motif from ICOS canis familiaris
<220> FEATURE:
<221> NAME/KEY: MISC_FEATURE
<222> LOCATION: (1)..(1)
<223> OTHER INFORMATION: X may be present or absent, and when present
      may be S.
<220> FEATURE:
<221> NAME/KEY: MISC_FEATURE
<222> LOCATION: (4)..(6)
<223> OTHER INFORMATION: Each X may be independently any amino acid.
<220> FEATURE:
<221> NAME/KEY: MISC_FEATURE
<222> LOCATION: (8)..(9)
<223> OTHER INFORMATION: Each X may be independently any amino acid.
<220> FEATURE:
<221> NAME/KEY: MISC_FEATURE
<222> LOCATION: (10)..(10)
<223> OTHER INFORMATION: X may be any amino acid, but preferably is D or
      E.

<400> SEQUENCE: 18

Xaa Ser Ser Xaa Xaa Xaa Pro Xaa Xaa Xaa
1               5                   10

<210> SEQ ID NO 19
<211> LENGTH: 4
<212> TYPE: PRT
<213> ORGANISM: Artificial Sequence
<220> FEATURE:
<223> OTHER INFORMATION: YXXM Motif from ICOS
<220> FEATURE:
<221> NAME/KEY: MISC_FEATURE
<222> LOCATION: (2)..(2)
<223> OTHER INFORMATION: X may be any amino acid, but preferably may be
      M
<220> FEATURE:
<221> NAME/KEY: MISC_FEATURE
<222> LOCATION: (3)..(3)
<223> OTHER INFORMATION: X may be any amino acid, but preferably may be
      F or P

<400> SEQUENCE: 19

Tyr Xaa Xaa Met
1
```

-continued

```
<210> SEQ ID NO 20
<211> LENGTH: 7
<212> TYPE: PRT
<213> ORGANISM: Artificial Sequence
<220> FEATURE:
<223> OTHER INFORMATION: Distal Motif of ICOS
<220> FEATURE:
<221> NAME/KEY: MISC_FEATURE
<222> LOCATION: (1)..(1)
<223> OTHER INFORMATION: X may be any amino acid, but preferably is A or
      S

<400> SEQUENCE: 20

Xaa Val Asn Thr Ala Lys Lys
1               5

<210> SEQ ID NO 21
<211> LENGTH: 199
<212> TYPE: PRT
<213> ORGANISM: artificial sequence
<220> FEATURE:
<223> OTHER INFORMATION: hICOS modified with proximal motif poly A

<400> SEQUENCE: 21

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ala Ala Ala Ala Ala Ala Ala
                165                 170                 175

Ala Ala Ala Tyr Met Phe Met Arg Ala Val Asn Thr Ala Lys Lys Ser
            180                 185                 190

Arg Leu Thr Asp Val Thr Leu
        195

<210> SEQ ID NO 22
<211> LENGTH: 10
<212> TYPE: PRT
<213> ORGANISM: artificial sequence
<220> FEATURE:
<223> OTHER INFORMATION: Poly A proximal motif alone

<400> SEQUENCE: 22

Ala Ala Ala Ala Ala Ala Ala Ala Ala Ala
1               5                   10
```

```
<210> SEQ ID NO 23
<211> LENGTH: 7
<212> TYPE: PRT
<213> ORGANISM: Artificial Sequence
<220> FEATURE:
<223> OTHER INFORMATION: Linker

<400> SEQUENCE: 23

Leu Glu Ser Gly Gly Gly Gly
1               5

<210> SEQ ID NO 24
<211> LENGTH: 10
<212> TYPE: PRT
<213> ORGANISM: Artificial Sequence
<220> FEATURE:
<223> OTHER INFORMATION: hICOS proximal motif alone

<400> SEQUENCE: 24

Ser Ser Ser Val His Asp Pro Asn Gly Glu
1               5                   10

<210> SEQ ID NO 25
<211> LENGTH: 4
<212> TYPE: PRT
<213> ORGANISM: artificial sequence
<220> FEATURE:
<223> OTHER INFORMATION: hICOS YXXM Motif alone

<400> SEQUENCE: 25

Tyr Met Phe Met
1

<210> SEQ ID NO 26
<211> LENGTH: 7
<212> TYPE: PRT
<213> ORGANISM: artificial sequence
<220> FEATURE:
<223> OTHER INFORMATION: hICOS distal motif alone

<400> SEQUENCE: 26

Ala Val Asn Thr Ala Lys Lys
1               5

<210> SEQ ID NO 27

<400> SEQUENCE: 27

000

<210> SEQ ID NO 28

<400> SEQUENCE: 28

000

<210> SEQ ID NO 29
<211> LENGTH: 10
<212> TYPE: PRT
<213> ORGANISM: artificial sequence
<220> FEATURE:
<223> OTHER INFORMATION: proximal motif derived from Macaca mulatta

<400> SEQUENCE: 29

Ser Ser Thr Val His Asp Pro Asn Gly Glu
1               5                   10
```

```
<210> SEQ ID NO 30
<400> SEQUENCE: 30

000

<210> SEQ ID NO 31
<211> LENGTH: 9
<212> TYPE: PRT
<213> ORGANISM: artificial sequence
<220> FEATURE:
<223> OTHER INFORMATION: proximal motif derived from Felis catus

<400> SEQUENCE: 31

Ser Ser Gly His Asp Pro Asn Ser Glu
1               5

<210> SEQ ID NO 32
<211> LENGTH: 9
<212> TYPE: PRT
<213> ORGANISM: artificial sequence
<220> FEATURE:
<223> OTHER INFORMATION: proximal motif derived from Bos Taurus

<400> SEQUENCE: 32

Thr Ser Val His Asp Pro Asn Ser Glu
1               5

<210> SEQ ID NO 33
<211> LENGTH: 9
<212> TYPE: PRT
<213> ORGANISM: artificial sequence
<220> FEATURE:
<223> OTHER INFORMATION: Proximal motif derived from Ailuropoda
      melanoleuca

<400> SEQUENCE: 33

Ser Ser Val His Asp Pro Asn Ser Glu
1               5

<210> SEQ ID NO 34
<400> SEQUENCE: 34

000

<210> SEQ ID NO 35
<400> SEQUENCE: 35

000

<210> SEQ ID NO 36
<400> SEQUENCE: 36

000

<210> SEQ ID NO 37
<211> LENGTH: 9
<212> TYPE: PRT
<213> ORGANISM: artificial sequence
<220> FEATURE:
<223> OTHER INFORMATION: Proximal motif derived from Meleagris gallopavo

<400> SEQUENCE: 37

Ser Ser Leu His Glu Pro Asn Ser Glu
1               5
```

```
<210> SEQ ID NO 38
<211> LENGTH: 9
<212> TYPE: PRT
<213> ORGANISM: artificial sequence
<220> FEATURE:
<223> OTHER INFORMATION: Proximal motif derived from Anas platyrhynchos

<400> SEQUENCE: 38

Ser Asn Ser His Glu Tyr Asn Ser Glu
1               5

<210> SEQ ID NO 39

<400> SEQUENCE: 39

000

<210> SEQ ID NO 40
<211> LENGTH: 9
<212> TYPE: PRT
<213> ORGANISM: artificial sequence
<220> FEATURE:
<223> OTHER INFORMATION: Proximal motif derived from Xenopus tropicalis

<400> SEQUENCE: 40

Thr Gln Asn Asn Glu Cys Asn Ser Glu
1               5

<210> SEQ ID NO 41
<211> LENGTH: 4
<212> TYPE: PRT
<213> ORGANISM: artificial sequence
<220> FEATURE:
<223> OTHER INFORMATION: alternate YXXM motif

<400> SEQUENCE: 41

Tyr Met Pro Met
1

<210> SEQ ID NO 42
<211> LENGTH: 31
<212> TYPE: PRT
<213> ORGANISM: artificial sequence
<220> FEATURE:
<223> OTHER INFORMATION: C terminal derived from Homo sapiens

<400> SEQUENCE: 42

Lys Tyr Ser Ser Ser Val His Asp Pro Asn Gly Glu Tyr Met Phe Met
1               5                   10                  15

Arg Ala Val Asn Thr Ala Lys Lys Ser Arg Leu Thr Asp Val Thr
            20                  25                  30

<210> SEQ ID NO 43
<211> LENGTH: 31
<212> TYPE: PRT
<213> ORGANISM: artificial sequence
<220> FEATURE:
<223> OTHER INFORMATION: C termimnal derived from Pan troglodytes

<400> SEQUENCE: 43

Lys Tyr Ser Ser Ser Val His Asp Pro Asn Gly Glu Tyr Met Phe Met
1               5                   10                  15

Arg Ala Val Asn Thr Ala Lys Lys Ser Arg Leu Thr Asp Val Thr
            20                  25                  30
```

```
<210> SEQ ID NO 44
<211> LENGTH: 32
<212> TYPE: PRT
<213> ORGANISM: artificial sequence
<220> FEATURE:
<223> OTHER INFORMATION: C terminal derived from Pongo abelii

<400> SEQUENCE: 44

Lys Tyr Ser Ser Ser Val His Asp Pro Asn Gly Glu Tyr Met Phe Met
1               5                   10                  15

Arg Ala Val Asn Thr Ala Lys Lys Ser Lys Leu Thr Asp Val Thr Ile
            20                  25                  30

<210> SEQ ID NO 45
<211> LENGTH: 31
<212> TYPE: PRT
<213> ORGANISM: artificial sequence
<220> FEATURE:
<223> OTHER INFORMATION: C terminal derived from Macaca mulatta

<400> SEQUENCE: 45

Lys Tyr Ser Ser Thr Val His Asp Pro Asn Gly Glu Tyr Met Phe Met
1               5                   10                  15

Arg Ala Val Asn Thr Ala Lys Lys Ser Arg Leu Thr Gly Thr Thr
            20                  25                  30

<210> SEQ ID NO 46
<211> LENGTH: 41
<212> TYPE: PRT
<213> ORGANISM: artificial sequence
<220> FEATURE:
<223> OTHER INFORMATION: C terminal derived from Canis Familiaris

<400> SEQUENCE: 46

Lys Tyr Arg Ser Ser Val His Asp Pro Asn Ser Glu Tyr Met Phe Met
1               5                   10                  15

Ala Ala Val Asn Thr Ala Lys Lys Pro Gly Leu Thr Gly Val Thr His
            20                  25                  30

Asn Leu Glu Leu Cys Gly Thr Gln Ala
        35                  40

<210> SEQ ID NO 47
<211> LENGTH: 41
<212> TYPE: PRT
<213> ORGANISM: artificial sequence
<220> FEATURE:
<223> OTHER INFORMATION: C terminal derived from Felis catus

<400> SEQUENCE: 47

Lys Tyr Arg Ser Ser Gly His Asp Pro Asn Ser Glu Tyr Met Phe Met
1               5                   10                  15

Ala Ala Val Asn Thr Ala Lys Lys Pro Gly Leu Thr Gly Val Thr His
            20                  25                  30

Asn Leu Glu Leu Cys Gly Thr Gln Ala
        35                  40

<210> SEQ ID NO 48
<211> LENGTH: 41
<212> TYPE: PRT
<213> ORGANISM: artificial sequence
<220> FEATURE:
<223> OTHER INFORMATION: C terminal derived from Bos Taurus
```

```
<400> SEQUENCE: 48

Lys Tyr Pro Thr Ser Val His Asp Pro Asn Ser Glu Tyr Met Phe Met
 1               5                  10                  15

Ala Ala Val Asn Thr Ala Lys Lys Pro Ala Pro Thr Asp Val Thr Arg
            20                  25                  30

Asn Leu Glu Leu Pro Gly Thr Gln Ala
        35                  40

<210> SEQ ID NO 49
<211> LENGTH: 41
<212> TYPE: PRT
<213> ORGANISM: artificial sequence
<220> FEATURE:
<223> OTHER INFORMATION: C terminal derived from Ailuopoda melanoleuca

<400> SEQUENCE: 49

Lys Tyr Arg Ser Ser Val His Asp Pro Asn Ser Glu Tyr Met Phe Met
 1               5                  10                  15

Ala Ala Val Asn Thr Ala Lys Lys Pro Gly Val Thr Gly Val Thr His
            20                  25                  30

Asn Leu Glu Leu Cys Gly Thr Gln Ala
        35                  40

<210> SEQ ID NO 50
<211> LENGTH: 31
<212> TYPE: PRT
<213> ORGANISM: artificial sequence
<220> FEATURE:
<223> OTHER INFORMATION: C terminal derived from Mus musculus

<400> SEQUENCE: 50

Lys Tyr Gly Ser Ser Val His Asp Pro Asn Ser Glu Tyr Met Phe Met
 1               5                  10                  15

Ala Ala Val Asn Thr Asn Lys Lys Ser Arg Leu Ala Gly Thr Ala
            20                  25                  30

<210> SEQ ID NO 51
<211> LENGTH: 32
<212> TYPE: PRT
<213> ORGANISM: artificial sequence
<220> FEATURE:
<223> OTHER INFORMATION: C terminal derived from Rattus norvegicus

<400> SEQUENCE: 51

Lys Tyr Arg Ser Ser Val His Asp Pro Asn Ser Glu Tyr Met Phe Met
 1               5                  10                  15

Ala Ala Val Asn Thr Asn Lys Lys Ser Arg Leu Ala Gly Met Thr Ser
            20                  25                  30

<210> SEQ ID NO 52
<211> LENGTH: 31
<212> TYPE: PRT
<213> ORGANISM: artificial sequence
<220> FEATURE:
<223> OTHER INFORMATION: C term derived from Oryctolagus cuniculus

<400> SEQUENCE: 52

Lys Tyr Gln Ser Ser Val His Asp Pro Asn Ser Glu Tyr Met Phe Met
 1               5                  10                  15

Ala Ala Val Asn Thr Ala Lys Lys Pro Thr Pro Pro Val Ile Leu
            20                  25                  30
```

```
<210> SEQ ID NO 53
<211> LENGTH: 28
<212> TYPE: PRT
<213> ORGANISM: artificial sequence
<220> FEATURE:
<223> OTHER INFORMATION: C term derived from Ornithorhynchus anatinus

<400> SEQUENCE: 53

Gln Cys Pro Ser Ser Leu His Glu Pro Asn Ser Glu Tyr Met Pro Met
1               5                   10                  15

Ala Ala Val Thr Ala Ala Lys Lys Ser Gly Phe Arg
            20                  25

<210> SEQ ID NO 54
<211> LENGTH: 27
<212> TYPE: PRT
<213> ORGANISM: artificial sequence
<220> FEATURE:
<223> OTHER INFORMATION: C terminal derived from Meleagris gallopavo

<400> SEQUENCE: 54

Gln Cys Glu Ser Ser Ser His Glu Tyr Asn Ser Glu Tyr Met Pro Met
1               5                   10                  15

Ala Ala Val Asn Ala Ala Lys Lys Pro Arg Ile
            20                  25

<210> SEQ ID NO 55
<211> LENGTH: 27
<212> TYPE: PRT
<213> ORGANISM: artificial sequence
<220> FEATURE:
<223> OTHER INFORMATION: C terminal derived from Gallus gallus

<400> SEQUENCE: 55

Gln Cys Glu Ser Asn Ser His Glu Tyr Asn Ser Glu Tyr Met Pro Met
1               5                   10                  15

Ala Ala Val Asn Ala Ala Lys Lys Pro Arg Ile
            20                  25

<210> SEQ ID NO 56
<211> LENGTH: 27
<212> TYPE: PRT
<213> ORGANISM: artificial sequence
<220> FEATURE:
<223> OTHER INFORMATION: C terminal derived from Anas platyrhynchos

<400> SEQUENCE: 56

Gln Cys Glu Ser Asn Ser His Glu Tyr Asn Ser Glu Tyr Met Pro Met
1               5                   10                  15

Ala Ala Val Asn Ala Ala Lys Lys Thr Arg Ile
            20                  25

<210> SEQ ID NO 57
<211> LENGTH: 27
<212> TYPE: PRT
<213> ORGANISM: artificial sequence
<220> FEATURE:
<223> OTHER INFORMATION: C terminal derived from Taeniopygia guttata

<400> SEQUENCE: 57

Lys Cys Glu Ser Asn Ser His Glu Tyr Asn Ser Glu Tyr Met Pro Met
1               5                   10                  15

Ala Ala Val Asn Ala Ala Lys Lys Pro Arg Ile
            20                  25
```

```
<210> SEQ ID NO 58
<211> LENGTH: 30
<212> TYPE: PRT
<213> ORGANISM: artificial sequence
<220> FEATURE:
<223> OTHER INFORMATION: C terminal derived from Xenopus tropicalis

<400> SEQUENCE: 58

Gln Gly Asn Thr Gln Asn Asn Glu Cys Asn Ser Glu Tyr Met Pro Met
1               5                   10                  15

Ala Ser Val Asn Pro Ala Lys Arg Pro Val Ile Pro Arg Leu
            20                  25                  30

<210> SEQ ID NO 59
<211> LENGTH: 22
<212> TYPE: DNA
<213> ORGANISM: artificial sequence
<220> FEATURE:
<223> OTHER INFORMATION: Short Hairpin RNA targeting Tbk1 gene.

<400> SEQUENCE: 59
aagacataaa gtgcttatta tg                                          22

<210> SEQ ID NO 60
<211> LENGTH: 22
<212> TYPE: DNA
<213> ORGANISM: artificial sequence
<220> FEATURE:
<223> OTHER INFORMATION: short hairpin RNA targeting ICOS gene.

<400> SEQUENCE: 60
ttcagttaat atggtttact at                                          22

<210> SEQ ID NO 61
<211> LENGTH: 20
<212> TYPE: PRT
<213> ORGANISM: artificial sequence
<220> FEATURE:
<223> OTHER INFORMATION: LCMV gp61-80 peptide

<400> SEQUENCE: 61

Gly Leu Asn Gly Pro Asp Ile Tyr Lys Gly Val Tyr Gln Phe Lys Ser
1               5                   10                  15

Val Glu Phe Asp
            20

<210> SEQ ID NO 62
<211> LENGTH: 22
<212> TYPE: DNA
<213> ORGANISM: artificial sequence
<220> FEATURE:
<223> OTHER INFORMATION: Icos Forward primer

<400> SEQUENCE: 62
actggtgatc tctatgctgt ca                                          22

<210> SEQ ID NO 63
<211> LENGTH: 22
<212> TYPE: DNA
<213> ORGANISM: artificial sequence
<220> FEATURE:
<223> OTHER INFORMATION: Icos Reverse primer

<400> SEQUENCE: 63
ttctggaagt ccatacgcat tg                                          22
```

```
<210> SEQ ID NO 64
<211> LENGTH: 20
<212> TYPE: DNA
<213> ORGANISM: artificial sequence
<220> FEATURE:
<223> OTHER INFORMATION: Tbk1 Forward primer

<400> SEQUENCE: 64
tgacccacct cctttttcaag                                              20

<210> SEQ ID NO 65
<211> LENGTH: 20
<212> TYPE: DNA
<213> ORGANISM: artificial sequence
<220> FEATURE:
<223> OTHER INFORMATION: Tbk1 Reverse primer

<400> SEQUENCE: 65
ttagggtcat gcacactgga                                               20

<210> SEQ ID NO 66
<211> LENGTH: 10
<212> TYPE: PRT
<213> ORGANISM: artificial sequence
<220> FEATURE:
<223> OTHER INFORMATION: TRAF2 Serine Tongs derived from Homo sapiens

<400> SEQUENCE: 66

Ser Ser Ser Phe Gln Arg Pro Val Asn Asp
1               5                   10

<210> SEQ ID NO 67
<211> LENGTH: 10
<212> TYPE: PRT
<213> ORGANISM: artificial sequence
<220> FEATURE:
<223> OTHER INFORMATION: TRAF2 Serine Tongs derived from Mus Musculus

<400> SEQUENCE: 67

Ser Ser Ser Phe Gln Arg Pro Val Ser Asp
1               5                   10

<210> SEQ ID NO 68
<211> LENGTH: 10
<212> TYPE: PRT
<213> ORGANISM: artificial sequence
<220> FEATURE:
<223> OTHER INFORMATION: TRAF2 Serine Tongs derived from Gallus gallus

<400> SEQUENCE: 68

Ser Ser Ser Phe Gln Arg Pro Val Thr Glu
1               5                   10

<210> SEQ ID NO 69
<211> LENGTH: 10
<212> TYPE: PRT
<213> ORGANISM: artificial sequence
<220> FEATURE:
<223> OTHER INFORMATION: TRAF2 Serine Tongs derived from Dario rerio

<400> SEQUENCE: 69

Ser Ser Ser Phe Gln Arg Pro Val Ser Asp
1               5                   10
```

<210> SEQ ID NO 70
<211> LENGTH: 10
<212> TYPE: PRT
<213> ORGANISM: artificial sequence
<220> FEATURE:
<223> OTHER INFORMATION: TRAF2 Serine Tongs derived from Branchiostoma
      floridae

<400> SEQUENCE: 70

Ser Ser Ser Phe Lys Arg Pro Thr Ser Asp
1               5                   10

<210> SEQ ID NO 71
<211> LENGTH: 10
<212> TYPE: PRT
<213> ORGANISM: artificial sequence
<220> FEATURE:
<223> OTHER INFORMATION: TRAF2 Serine Tongs derived from amphimedon
      queenslandica

<400> SEQUENCE: 71

Ser Ser Ser Phe Gln Arg Pro Lys Ser Asp
1               5                   10

<210> SEQ ID NO 72
<211> LENGTH: 501
<212> TYPE: PRT
<213> ORGANISM: Homo sapiens

<400> SEQUENCE: 72

Met Ala Ala Ala Ser Val Thr Pro Pro Gly Ser Leu Glu Leu Leu Gln
1               5                   10                  15

Pro Gly Phe Ser Lys Thr Leu Leu Gly Thr Lys Leu Glu Ala Lys Tyr
                20                  25                  30

Leu Cys Ser Ala Cys Arg Asn Val Leu Arg Arg Pro Phe Gln Ala Gln
            35                  40                  45

Cys Gly His Arg Tyr Cys Ser Phe Cys Leu Ala Ser Ile Leu Ser Ser
        50                  55                  60

Gly Pro Gln Asn Cys Ala Ala Cys Val His Glu Gly Ile Tyr Glu Glu
65                  70                  75                  80

Gly Ile Ser Ile Leu Glu Ser Ser Ala Phe Pro Asp Asn Ala Ala
                85                  90                  95

Arg Arg Glu Val Glu Ser Leu Pro Ala Val Cys Pro Ser Asp Gly Cys
                100                 105                 110

Thr Trp Lys Gly Thr Leu Lys Glu Tyr Glu Ser Cys His Glu Gly Arg
            115                 120                 125

Cys Pro Leu Met Leu Thr Glu Cys Pro Ala Cys Lys Gly Leu Val Arg
        130                 135                 140

Leu Gly Glu Lys Glu Arg His Leu Glu His Cys Pro Glu Arg Ser
145                 150                 155                 160

Leu Ser Cys Arg His Cys Arg Ala Pro Cys Cys Gly Ala Asp Val Lys
                165                 170                 175

Ala His His Glu Val Cys Pro Lys Phe Pro Leu Thr Cys Asp Gly Cys
                180                 185                 190

Gly Lys Lys Lys Ile Pro Arg Glu Lys Phe Gln Asp His Val Lys Thr
            195                 200                 205

Cys Gly Lys Cys Arg Val Pro Cys Arg Phe His Ala Ile Gly Cys Leu
        210                 215                 220

Glu Thr Val Glu Gly Glu Lys Gln Gln Glu His Glu Val Gln Trp Leu
225                 230                 235                 240

```
Arg Glu His Leu Ala Met Leu Leu Ser Ser Val Leu Glu Ala Lys Pro
                245                 250                 255

Leu Leu Gly Asp Gln Ser His Ala Gly Ser Glu Leu Leu Gln Gly Cys
        260                 265                 270

Glu Ser Leu Glu Lys Lys Thr Ala Thr Phe Glu Asn Ile Val Cys Val
            275                 280                 285

Leu Asn Arg Glu Val Glu Arg Val Ala Met Thr Ala Glu Ala Cys Ser
        290                 295                 300

Arg Gln His Arg Leu Asp Gln Asp Lys Ile Glu Ala Pro Ser Ser Lys
305                 310                 315                 320

Val Gln Gln Leu Glu Arg Ser Ile Gly Leu Lys Asp Leu Ala Met Ala
                325                 330                 335

Asp Leu Glu Gln Lys Val Ser Glu Met Glu Ala Ser Thr Tyr Asp Gly
        340                 345                 350

Val Phe Ile Trp Lys Ile Ser Asp Phe Ala Arg Lys Arg Gln Glu Ala
            355                 360                 365

Val Ala Gly Arg Ile Pro Ala Ile Phe Ser Pro Ala Phe Tyr Thr Arg
        370                 375                 380

Arg Tyr Gly Tyr Lys Met Cys Leu Arg Ile Tyr Leu Asn Gly Asp Gly
385                 390                 395                 400

Thr Gly Arg Gly Thr His Leu Ser Leu Phe Phe Val Val Met Lys Gly
                405                 410                 415

Pro Asn Asp Ala Leu Leu Arg Trp Pro Phe Asn Gln Lys Val Thr Leu
        420                 425                 430

Met Leu Leu Asp Gln Asn Asn Arg Glu His Val Ile Asp Ala Phe Arg
            435                 440                 445

Pro Asp Val Thr Ser Ser Phe Gln Arg Pro Val Asn Asp Met Asn
        450                 455                 460

Ile Ala Ser Gly Cys Pro Leu Phe Cys Pro Val Ser Lys Met Glu Ala
465                 470                 475                 480

Lys Asp Ser Tyr Val Arg Asp Ala Ile Phe Ile Lys Ala Ile Val
                485                 490                 495

Asp Leu Thr Gly Leu
            500

<210> SEQ ID NO 73
<211> LENGTH: 501
<212> TYPE: PRT
<213> ORGANISM: Mus musculus

<400> SEQUENCE: 73

Met Ala Ala Ala Ser Val Thr Ser Pro Gly Ser Leu Glu Leu Leu Gln
1               5                   10                  15

Pro Gly Phe Ser Lys Thr Leu Leu Gly Thr Arg Leu Glu Ala Lys Tyr
            20                  25                  30

Leu Cys Ser Ala Cys Lys Asn Ile Leu Arg Arg Pro Phe Gln Ala Gln
        35                  40                  45

Cys Gly His Arg Tyr Cys Ser Phe Cys Leu Thr Ser Ile Leu Ser Ser
    50                  55                  60

Gly Pro Gln Asn Cys Ala Ala Cys Val Tyr Glu Gly Leu Tyr Glu Glu
65                  70                  75                  80

Gly Ile Ser Ile Leu Glu Ser Ser Ala Phe Pro Asp Asn Ala Ala
                85                  90                  95

Arg Arg Glu Val Glu Ser Leu Pro Ala Val Cys Pro Asn Asp Gly Cys
            100                 105                 110
```

```
Thr Trp Lys Gly Thr Leu Lys Glu Tyr Glu Ser Cys His Glu Gly Leu
            115                 120                 125
Cys Pro Phe Leu Leu Thr Glu Cys Pro Ala Cys Lys Gly Leu Val Arg
        130                 135                 140
Leu Ser Glu Lys Glu His His Thr Glu Gln Glu Cys Pro Lys Arg Ser
145                 150                 155                 160
Leu Ser Cys Gln His Cys Arg Ala Pro Cys Ser His Val Asp Leu Glu
                165                 170                 175
Val His Tyr Glu Val Cys Pro Lys Phe Pro Leu Thr Cys Asp Gly Cys
            180                 185                 190
Gly Lys Lys Lys Ile Pro Arg Glu Thr Phe Gln Asp His Val Arg Ala
            195                 200                 205
Cys Ser Lys Cys Arg Val Leu Cys Arg Phe His Thr Val Gly Cys Ser
        210                 215                 220
Glu Met Val Glu Thr Glu Asn Leu Gln Asp His Glu Leu Gln Arg Leu
225                 230                 235                 240
Arg Glu His Leu Ala Leu Leu Leu Ser Ser Phe Leu Glu Ala Gln Ala
                245                 250                 255
Ser Pro Gly Thr Leu Asn Gln Val Gly Pro Glu Leu Leu Gln Arg Cys
            260                 265                 270
Gln Ile Leu Glu Gln Lys Ile Ala Thr Phe Glu Asn Ile Val Cys Val
        275                 280                 285
Leu Asn Arg Glu Val Glu Arg Val Ala Val Thr Ala Glu Ala Cys Ser
290                 295                 300
Arg Gln His Arg Leu Asp Gln Asp Lys Ile Glu Ala Leu Ser Asn Lys
305                 310                 315                 320
Val Gln Gln Leu Glu Arg Ser Ile Gly Leu Lys Asp Leu Ala Met Ala
                325                 330                 335
Asp Leu Glu Gln Lys Val Ser Glu Leu Glu Val Ser Thr Tyr Asp Gly
            340                 345                 350
Val Phe Ile Trp Lys Ile Ser Asp Phe Thr Arg Lys Arg Gln Glu Ala
        355                 360                 365
Val Ala Gly Arg Thr Pro Ala Ile Phe Ser Pro Ala Phe Tyr Thr Ser
    370                 375                 380
Arg Tyr Gly Tyr Lys Met Cys Leu Arg Val Tyr Leu Asn Gly Asp Gly
385                 390                 395                 400
Thr Gly Arg Gly Thr His Leu Ser Leu Phe Phe Val Val Met Lys Gly
                405                 410                 415
Pro Asn Asp Ala Leu Leu Gln Trp Pro Phe Asn Gln Lys Val Thr Leu
            420                 425                 430
Met Leu Leu Asp His Asn Asn Arg Glu His Val Ile Asp Ala Phe Arg
        435                 440                 445
Pro Asp Val Thr Ser Ser Ser Phe Gln Arg Pro Val Ser Asp Met Asn
    450                 455                 460
Ile Ala Ser Gly Cys Pro Leu Phe Cys Pro Val Ser Lys Met Glu Ala
465                 470                 475                 480
Lys Asn Ser Tyr Val Arg Asp Asp Ala Ile Phe Ile Lys Ala Ile Val
                485                 490                 495
Asp Leu Thr Gly Leu
            500
```

<210> SEQ ID NO 74
<211> LENGTH: 527
<212> TYPE: PRT
<213> ORGANISM: Gallus gallus

<400> SEQUENCE: 74

Met Ala Ala Ala Asn Ser Thr Pro Pro Gly Ser Leu Asp Leu Ser Gln
1               5                   10                  15

Pro Gly Phe Ala Lys Glu Ile Leu Gly Thr Lys Leu Glu Val Lys Tyr
            20                  25                  30

Leu Cys Ser Asp Cys Arg Asn Ile Leu Arg Arg Pro Phe Gln Ala Gln
        35                  40                  45

Cys Gly His Arg Tyr Cys Ser Tyr Cys Leu Lys Ile Ile Ser Ser
    50                  55                  60

Gly Pro Gln Lys Cys Ala Ser Cys Ile Gln Glu Gly Ile Tyr Glu Glu
65                  70                  75                  80

Gly Ile Ser Ile Leu Glu Thr Ser Ala Phe Pro Asp Asn Ala Ala
                85                  90                  95

Arg Arg Glu Val Glu Ser Leu Pro Ala Val Cys Ile Asn Glu Gly Cys
            100                 105                 110

Thr Trp Lys Gly Thr Ile Lys Glu Tyr Glu Ser Cys His Glu Gly Asn
        115                 120                 125

Cys Pro Phe Leu Leu Ile Glu Cys Gln Ala Cys Arg Gly Val Ile Pro
130                 135                 140

Leu Asn Glu Lys Glu Arg His Ser Glu Arg Glu Cys Pro Glu Arg Thr
145                 150                 155                 160

Leu Asn Cys Lys Tyr Cys Lys Ser Leu Phe Tyr Phe Pro Asp Ile Lys
                165                 170                 175

Ala His Asp Glu Val Cys Pro Lys Phe Pro Leu Thr Cys Asp Gly Cys
            180                 185                 190

Gly Lys Lys Lys Ile Pro Arg Glu Lys Phe Gln Asp His Val Lys Asn
        195                 200                 205

Cys Gly Lys Cys Lys Val Pro Cys Arg Phe Lys Val Val Gly Cys Ala
210                 215                 220

Glu Met Val Glu Asn Glu Lys Leu Pro Glu His Glu Ser Lys Cys Leu
225                 230                 235                 240

Ala Glu His Leu Tyr Met Leu Leu Ser Phe Val Leu Ser Leu Lys Ser
                245                 250                 255

Gly Ser Gly Asp Leu Lys His Leu Pro Ala Ile Pro Ser Ser Gln Ser
            260                 265                 270

Ser Ser Pro Leu Leu Ala Ala Asn Ser Leu Cys Pro Glu Ser Glu Leu
        275                 280                 285

Phe Lys Ser Leu Glu Leu Leu Gly Arg Cys Asp Ala Leu Glu Lys Lys
290                 295                 300

Thr Val Thr Phe Glu Asn Ile Val Cys Val Leu Asn Arg Glu Val
305                 310                 315                 320

Arg Val Ser Leu Thr Ala Glu Ala Tyr Ser Arg Gln His Arg Leu Asp
                325                 330                 335

Gln Glu Gln Ile Glu Thr Leu Ser Asn Lys Val Arg Gly Leu Glu Arg
            340                 345                 350

Ser Ile Gly Leu Lys Asp Leu Ala Met Ala Glu Met Glu Lys Ile
        355                 360                 365

Arg Asn Met Glu Ala Ser Thr Tyr Asp Gly Val Phe Ile Trp Lys Ile
370                 375                 380

```
Thr Glu Phe Ala Arg Lys Arg Gln Glu Ala Ile Thr Gly Arg Ser Pro
385                 390                 395                 400

Ala Ile Phe Ser Pro Ala Phe Tyr Thr Ser Lys Tyr Gly Tyr Lys Met
            405                 410                 415

Cys Leu Arg Val Tyr Leu Asn Gly Asp Gly Thr Gly Arg Gly Thr His
            420                 425                 430

Leu Ser Leu Phe Phe Val Val Met Lys Gly Pro Asn Asp Ala Leu Leu
            435                 440                 445

Arg Trp Pro Phe Asn Gln Lys Val Thr Leu Met Leu Leu Asp Gln Asn
450                 455                 460

Asn Arg Glu His Ile Ile Asp Ala Phe Arg Pro Asp Val Thr Ser Ser
465                 470                 475                 480

Ser Phe Gln Arg Pro Val Thr Glu Met Asn Ile Ala Ser Gly Cys Pro
            485                 490                 495

Leu Phe Cys Pro Val Ser Val Met Glu Ala Lys Asn Ser Tyr Val Arg
            500                 505                 510

Asp Asp Ala Ile Phe Ile Lys Ala Ile Val Asp Leu Ser Gly Leu
            515                 520                 525

<210> SEQ ID NO 75
<211> LENGTH: 575
<212> TYPE: PRT
<213> ORGANISM: danio rerio

<400> SEQUENCE: 75

Met Ala Ala Gln Glu Pro Ser Pro Pro Ser Ser Leu Glu Gly Asn Lys
1               5                   10                  15

Pro Gly Phe Pro Lys Lys Ile Leu Ala Asn Lys Leu Glu Asp Lys His
            20                  25                  30

Leu Cys Asn Ile Cys Leu Lys Ile Leu Arg Arg Pro Phe Gln Ala Gln
        35                  40                  45

Cys Gly His Arg Phe Cys Ser Tyr Cys Phe Asn Lys Ala Val Ser Ser
    50                  55                  60

Gly Pro Gln Lys Cys Ser Ala Cys Ile Lys Glu Asp Ile Phe Glu Glu
65                  70                  75                  80

Pro Thr Ser Ile Leu Lys Gln Gly Cys Ala Phe Pro Asp Asn Ala Ala
                85                  90                  95

Lys Arg Glu Val Glu Ala Leu Glu Ala Val Cys Ile Asn Glu Glu Cys
            100                 105                 110

Ser Trp Thr Gly Thr Ile Lys Glu Tyr Glu Ala Asn His Glu Gly Lys
        115                 120                 125

Cys Asp Phe Arg Ile Leu Pro Cys Pro Ser Cys Lys Glu Leu Leu Arg
    130                 135                 140

Ala Asn Glu Leu Glu Arg His Asn Glu Arg Gly Cys Pro Glu Arg Thr
145                 150                 155                 160

Leu Asn Cys Lys Tyr Cys Lys Glu Pro Phe His Phe Lys Asn Ile Lys
                165                 170                 175

Ala His Asp Glu Ile Cys Pro Lys Tyr Pro Met Ile Cys Glu Gly Cys
            180                 185                 190

Ala Lys Lys Lys Ile Pro Arg Glu Lys Tyr Val Asp His Ile Lys Leu
        195                 200                 205

Cys Thr Lys Phe Arg Thr Pro Cys Arg Phe His Val Val Gly Cys Asp
    210                 215                 220

Met Thr Val Glu Lys Glu Lys Ile His Asp His Glu Gln Ala Cys Ser
225                 230                 235                 240
```

```
Tyr Glu His Leu Asn Leu Leu His Phe Ile Met Gly Ile Lys Val
            245                 250                 255

Asn Leu Glu Ser Leu Gln Pro Gln Ser Leu Glu Leu Ala Ser His Lys
            260                 265                 270

Ile His Glu Leu His Gln Ser Leu Arg Glu Leu Glu Leu Lys Met Gly
            275                 280                 285

Gln Leu Cys Gly Ala Gly Ala Ser Val Gln Gly Ala Cys Ala Leu Pro
            290                 295                 300

Pro Pro Pro Pro Ala Pro Thr Leu Gly Thr Ser Phe Thr Pro Leu
305             310                 315                 320

Pro Thr Ala Val Gly Ala Ala Leu Glu Leu Gln Leu His Ser Glu Lys
            325                 330                 335

Thr Lys Val Val Glu Leu Ser Arg Arg Cys Gln Glu Leu Glu Leu Lys
            340                 345                 350

Val Asn Thr Phe Glu Asn Ile Val Cys Val Leu Asn Arg Glu Met Glu
            355                 360                 365

Arg Ser Ala Thr Thr Met Glu Ala Tyr Asn Arg Gln His Arg Leu Asp
            370                 375                 380

Gln Asp Lys Ile Glu Ile Leu Asn Asn Lys Val Arg Gln Leu Glu Arg
385             390                 395                 400

Thr Val Gly Leu Arg Asp Leu Ser Ile Val Glu Met Glu Ala Lys Met
            405                 410                 415

Arg Glu Met Ser Ala Ala Thr Tyr Asp Gly Val Phe Val Trp Lys Ile
            420                 425                 430

Ser Asp Phe Ser Lys Lys Arg Gln Asp Ala Val Ala Gly Arg Ala Pro
            435                 440                 445

Ala Met Phe Ser Pro Ala Phe Tyr Thr Ser Lys Tyr Gly Tyr Lys Met
            450                 455                 460

Cys Leu Arg Ile Tyr Leu Asn Gly Asp Gly Thr Gly Arg Gly Thr His
465             470                 475                 480

Leu Ser Leu Phe Phe Val Val Met Arg Gly His Ser Asp Ala Leu Leu
            485                 490                 495

Lys Trp Pro Phe Asn Gln Lys Val Thr Leu Met Leu Leu Asp Gln Asn
            500                 505                 510

Asn Arg Glu His Ile Ile Asp Ala Phe Arg Pro Asp Ile Ser Ser Ser
            515                 520                 525

Ser Phe Gln Arg Pro Val Ser Asp Met Asn Ile Ala Ser Gly Cys Pro
            530                 535                 540

Leu Phe Cys Pro Leu Ser Lys Leu Asp Ser Lys Asn Ser Tyr Ile Arg
545             550                 555                 560

Asp Asp Thr Ile Phe Ile Lys Ala Ile Val Asp Leu Thr Gly Leu
            565                 570                 575

<210> SEQ ID NO 76
<211> LENGTH: 482
<212> TYPE: PRT
<213> ORGANISM: Branchiostoma floridae

<400> SEQUENCE: 76

Met Pro Gly Tyr Ser Arg Glu Ile Phe Glu Val Arg Val Glu Asp Lys
1               5                   10                  15

Tyr Leu Cys Ser Ala Cys Arg Leu Val Leu Arg Glu Pro Phe Gln Thr
            20                  25                  30

Tyr Cys Gly His Arg Tyr Cys Lys Ser Cys Leu Asp Glu Ile Phe Glu
            35                  40                  45
```

```
Tyr Ala Phe Pro Asp Arg Ala Ile Lys Arg Asp Ile Gly Asp Leu Pro
     50                  55                  60

Val Lys Cys Leu Asn Ala Gly Leu Cys Glu Trp Lys Gly Lys Ala Glu
 65                  70                  75                  80

Gln Tyr Asp Glu His Gln Glu Thr Cys Glu Phe Val Leu Ile Pro Cys
                     85                  90                  95

Pro Lys Gln Gly Cys Gly Lys Gln Val Met Arg Met Asp Leu Ala Ala
                100                 105                 110

His Leu Glu Lys Glu Cys Ala Val Arg Gln Val Lys Cys Lys Tyr Cys
                115                 120                 125

Ala Gln Glu Ile Leu Leu Lys Asp Glu Lys Asp His Leu Phe Ile Cys
            130                 135                 140

Pro Gln Val Pro Val Asn Cys Asp Phe Cys Gly Lys Lys Ile Pro
145                 150                 155                 160

Arg Ala Gln Leu Gln Gln His Gln Asp Glu Asp Thr Gly Asp Cys Lys
                165                 170                 175

Arg Leu Lys Val Ala Cys Arg Phe Ala Lys Val Gly Cys Gln Ala Lys
                180                 185                 190

Leu Glu Arg Glu Lys Leu Asn Asp His Ile Ala Lys Asn His Val Asp
            195                 200                 205

His Leu Asn His Leu Leu Asp Asn His Leu Thr Leu Met Glu Lys Val
210                 215                 220

Asn Leu Leu Lys Gln Asn Pro Gln Ala Gln His Met Gln Gln Ala Met
225                 230                 235                 240

Ala Ser Lys Gln Glu Glu Met Arg His Lys Tyr Val Ala Met Glu Thr
            245                 250                 255

Arg Val Ala Thr Phe Glu Gly Ile Val Ala Val Leu Asn Arg Glu Ile
                260                 265                 270

Glu Lys Cys Ser Ala Thr Ile Glu Ala Tyr Glu Arg Gln Arg Arg Gln
            275                 280                 285

Asp Arg Glu Ile Ile Glu Ser Ile Glu Arg Lys Met Lys Ser Gln Glu
            290                 295                 300

Arg Ile Ile Ala Leu Lys Asp Val Ala Leu Ala Glu Gln Asp Leu Arg
305                 310                 315                 320

Ile Thr Ser Leu Glu Met Thr Ser Tyr Asp Ala Thr Leu Leu Trp Lys
                325                 330                 335

Ile Gln Asp Phe Thr Arg Lys Arg His Asp Ala Ile Thr Gly Lys Thr
                340                 345                 350

Thr Ser Ile Tyr Ser Pro Cys Phe Tyr Thr Ser Arg Thr Gly Tyr Lys
            355                 360                 365

Met Cys Ala Arg Ile Tyr Leu Asn Gly Asp Gly Met Gly Lys Gly Ser
            370                 375                 380

His Ile Ser Leu Phe Phe Val Leu Met Arg Gly His Phe Asp Gly Leu
385                 390                 395                 400

Leu Arg Trp Pro Phe Arg Gln Lys Val Thr Phe Met Leu Leu Asp Gln
                405                 410                 415

Asn Asn Arg Glu His Val Ile Asp Ala Phe Arg Pro Asp Pro Thr Ser
            420                 425                 430

Ser Ser Phe Lys Arg Pro Thr Ser Asp Met Asn Ile Ala Ser Gly Cys
            435                 440                 445

Pro Leu Phe Met Pro Leu Ser Gln Leu Glu Ser Thr Arg His Ala Tyr
450                 455                 460
```

Val Arg Asp Asp Ala Ile Phe Leu Lys Ile Ile Val Asp Thr Ser Asp
465                 470                 475                 480

Leu Asn

<210> SEQ ID NO 77
<211> LENGTH: 498
<212> TYPE: PRT
<213> ORGANISM: Amphimedon queenslandica

<400> SEQUENCE: 77

Met Pro Gly Tyr Asp Leu Lys Ile Asn Gly Glu Tyr Ala Arg Ile Glu
1               5                   10                  15

Ser Leu Gln Cys Ser Ser Cys Glu Leu Ile Leu Lys Asp Ala Ile Gln
            20                  25                  30

Asn Glu Asp Gly Gln Arg Phe Cys Lys Ser Cys Trp Glu Glu Ala Ile
        35                  40                  45

Ser Ser Ser Lys Ala Gln Lys Leu Gly Ile Asn Pro Lys Glu Glu
    50                  55                  60

Ile His Pro Asp Ile Ala Val Arg Arg Glu Ile Asp Arg Leu Pro Val
65                  70                  75                  80

Leu Cys Glu Asn Tyr Glu Asn Gly Cys Asp Trp Thr Gly Lys Leu Lys
                85                  90                  95

Asp His Glu His Asp His Lys Ala Ile Cys Glu Tyr Lys Thr Met Arg
            100                 105                 110

Cys Pro Leu Gly Cys Gly Lys Arg Ile Pro Leu Gly Lys Leu Arg Lys
        115                 120                 125

His Glu Lys Glu Glu Cys Pro Phe Arg Gln Val Arg Cys Gln Tyr Cys
130                 135                 140

Arg Ser Glu Leu Leu Ala Gly Asp Tyr Asp Asp His Leu Leu Asn Cys
145                 150                 155                 160

Pro Asn Ala Pro Tyr Thr Cys Gly His Cys His Thr Glu Met Pro Arg
                165                 170                 175

Ser Glu Ile His Lys Ser Leu Ser Lys His Pro Asn Pro Ile Ser His
            180                 185                 190

Leu Glu Asn Asp Gln Val Phe Met His Leu Gln Met Leu Gly Leu Ala
        195                 200                 205

Met Lys Arg Leu Glu Thr His Phe Asn Val Ala Leu Lys Asp Ile Lys
210                 215                 220

Lys Glu Leu Thr Glu Ile Asp Glu Ser Asn Ser Lys Phe Lys Asp Lys
225                 230                 235                 240

Met Ile Asn Glu Ser Ser Ser Leu Thr Lys Gln Val Lys Gln Leu Glu
                245                 250                 255

Glu Arg Leu Lys Gly Glu Pro Ser Asn Arg Ile Ile Ile Glu Leu Gln
            260                 265                 270

Gly Glu Val Thr Lys Leu Ala Glu Arg Val Ser Lys Val Glu Ser Gly
        275                 280                 285

Ala Ser Tyr Arg Pro Leu Asn Gln Gly Tyr Asp Asp Met Ser Thr Ser
290                 295                 300

Asp Ser Lys Met Gly Gly Ser Ile Glu His Lys Leu Ala Glu Gln Glu
305                 310                 315                 320

Arg Thr Ser Gly Met Leu Lys Val His Leu Ser Glu Leu Glu Leu Gln
                325                 330                 335

Leu Gln Ala Ser Leu Ala Ser Thr Tyr Asn Gly Ser Phe Leu Trp Arg
            340                 345                 350

```
Ile Pro Asp Val Lys Arg Arg Lys Arg Asp Ala Ile Glu Gly Lys Ile
            355                 360                 365

Thr Ser Ile Tyr Ser Pro Pro Phe Tyr Thr Gly Arg Asn Gly Tyr Lys
        370                 375                 380

Met Cys Ile Arg Ala Tyr Leu Asn Gly Asp Gly Ile Gly Tyr Asn Thr
385                 390                 395                 400

His Leu Ser Ile Phe Phe Val Leu Met Lys Gly Glu Tyr Asp Pro Leu
            405                 410                 415

Leu Lys Trp Pro Phe Asp Phe Lys Val Ser Leu Ile Met Val Asp Gln
            420                 425                 430

Asp His Lys Arg His Ile Val Gln Thr Phe Lys Pro Ser Pro Ser Ser
            435                 440                 445

Ser Ser Phe Gln Arg Pro Lys Ser Asp Met Asn Ile Ala Ser Gly Cys
        450                 455                 460

Pro Lys Phe Ala Glu Leu Lys Ile Leu Asp Asn Glu Ser Tyr Val Lys
465                 470                 475                 480

Glu Asp Val Met Tyr Val Lys Ala Ile Val Asp Thr Thr Arg Ile Phe
                485                 490                 495

His Pro

<210> SEQ ID NO 78
<211> LENGTH: 10
<212> TYPE: PRT
<213> ORGANISM: artificial sequence
<220> FEATURE:
<223> OTHER INFORMATION: TRAF3 Serine Tongs derived from Homo sapiens

<400> SEQUENCE: 78

Ser Ser Ser Phe Lys Lys Pro Thr Gly Glu
1               5                   10

<210> SEQ ID NO 79
<211> LENGTH: 10
<212> TYPE: PRT
<213> ORGANISM: artificial sequence
<220> FEATURE:
<223> OTHER INFORMATION: TRAF3 Serine Tongs derived from Mus musculus

<400> SEQUENCE: 79

Ser Ser Ser Phe Lys Lys Pro Thr Gly Glu
1               5                   10

<210> SEQ ID NO 80
<211> LENGTH: 10
<212> TYPE: PRT
<213> ORGANISM: artificial sequence
<220> FEATURE:
<223> OTHER INFORMATION: TRAF3 Serine Tongs derived from Gallus gallus

<400> SEQUENCE: 80

Ser Ser Ser Phe Lys Lys Pro Thr Gly Glu
1               5                   10

<210> SEQ ID NO 81
<211> LENGTH: 10
<212> TYPE: PRT
<213> ORGANISM: artificial sequence
<220> FEATURE:
<223> OTHER INFORMATION: TRAF3 Serine Tongs derived from Dario rerio
```

```
<400> SEQUENCE: 81

Ser Ser Ser Phe Arg Arg Pro Thr Gly Glu
1               5                   10

<210> SEQ ID NO 82
<211> LENGTH: 10
<212> TYPE: PRT
<213> ORGANISM: artificial sequence
<220> FEATURE:
<223> OTHER INFORMATION: TRAF3 Serine Tongs derived from Eptatretus
      brugeri

<400> SEQUENCE: 82

Ser Ser Ser Phe Lys Arg Pro Thr Ser Glu
1               5                   10

<210> SEQ ID NO 83
<211> LENGTH: 10
<212> TYPE: PRT
<213> ORGANISM: artificial sequence
<220> FEATURE:
<223> OTHER INFORMATION: TRAF3 Serine Tongs derived from Pinctada fucata

<400> SEQUENCE: 83

Ser Ser Ser Phe Arg Lys Pro Thr Thr Glu
1               5                   10

<210> SEQ ID NO 84
<211> LENGTH: 10
<212> TYPE: PRT
<213> ORGANISM: artificial sequence
<220> FEATURE:
<223> OTHER INFORMATION: TRAF3 Serine Tongs derived from
      Strongylocentrotus purpuratus

<400> SEQUENCE: 84

Ser Ser Ser Phe Gln Arg Pro Thr Ser Asn
1               5                   10

<210> SEQ ID NO 85
<211> LENGTH: 10
<212> TYPE: PRT
<213> ORGANISM: artificial sequence
<220> FEATURE:
<223> OTHER INFORMATION: TRAF3 Serine Tongs derived from Nematostella
      vectensis

<400> SEQUENCE: 85

Ser Ser Ser Phe Lys Arg Pro Thr Ser Asn
1               5                   10

<210> SEQ ID NO 86
<211> LENGTH: 568
<212> TYPE: PRT
<213> ORGANISM: homo sapiens

<400> SEQUENCE: 86

Met Glu Ser Ser Lys Lys Met Asp Ser Pro Gly Ala Leu Gln Thr Asn
1               5                   10                  15

Pro Pro Leu Lys Leu His Thr Asp Arg Ser Ala Gly Thr Pro Val Phe
            20                  25                  30

Val Pro Glu Gln Gly Gly Tyr Lys Glu Lys Phe Val Lys Thr Val Glu
        35                  40                  45

Asp Lys Tyr Lys Cys Glu Lys Cys His Leu Val Leu Cys Ser Pro Lys
    50                  55                  60
```

```
Gln Thr Glu Cys Gly His Arg Phe Cys Glu Ser Cys Met Ala Ala Leu
 65                  70                  75                  80

Leu Ser Ser Ser Pro Lys Cys Thr Ala Cys Gln Glu Ser Ile Val
             85                  90                  95

Lys Asp Lys Val Phe Lys Asp Asn Cys Cys Lys Arg Glu Ile Leu Ala
            100                 105                 110

Leu Gln Ile Tyr Cys Arg Asn Glu Ser Arg Gly Cys Ala Glu Gln Leu
            115                 120                 125

Met Leu Gly His Leu Leu Val His Leu Lys Asn Asp Cys His Phe Glu
            130                 135                 140

Glu Leu Pro Cys Val Arg Pro Asp Cys Lys Glu Lys Val Leu Arg Lys
145                 150                 155                 160

Asp Leu Arg Asp His Val Glu Lys Ala Cys Lys Tyr Arg Glu Ala Thr
                165                 170                 175

Cys Ser His Cys Lys Ser Gln Val Pro Met Ile Ala Leu Gln Lys His
                180                 185                 190

Glu Asp Thr Asp Cys Pro Cys Val Val Ser Cys Pro His Lys Cys
            195                 200                 205

Ser Val Gln Thr Leu Leu Arg Ser Glu Leu Ser Ala His Leu Ser Glu
            210                 215                 220

Cys Val Asn Ala Pro Ser Thr Cys Ser Phe Lys Arg Tyr Gly Cys Val
225                 230                 235                 240

Phe Gln Gly Thr Asn Gln Gln Ile Lys Ala His Glu Ala Ser Ser Ala
            245                 250                 255

Val Gln His Val Asn Leu Leu Lys Glu Trp Ser Asn Ser Leu Glu Lys
            260                 265                 270

Lys Val Ser Leu Leu Gln Asn Glu Ser Val Glu Lys Asn Lys Ser Ile
            275                 280                 285

Gln Ser Leu His Asn Gln Ile Cys Ser Phe Glu Ile Glu Ile Glu Arg
            290                 295                 300

Gln Lys Glu Met Leu Arg Asn Asn Glu Ser Lys Ile Leu His Leu Gln
305                 310                 315                 320

Arg Val Ile Asp Ser Gln Ala Glu Lys Leu Lys Glu Leu Asp Lys Glu
                325                 330                 335

Ile Arg Pro Phe Arg Gln Asn Trp Glu Glu Ala Asp Ser Met Lys Ser
                340                 345                 350

Ser Val Glu Ser Leu Gln Asn Arg Val Thr Glu Leu Glu Ser Val Asp
            355                 360                 365

Lys Ser Ala Gly Gln Val Ala Arg Asn Thr Gly Leu Leu Glu Ser Gln
            370                 375                 380

Leu Ser Arg His Asp Gln Met Leu Ser Val His Asp Ile Arg Leu Ala
385                 390                 395                 400

Asp Met Asp Leu Arg Phe Gln Val Leu Glu Thr Ala Ser Tyr Asn Gly
                405                 410                 415

Val Leu Ile Trp Lys Ile Arg Asp Tyr Lys Arg Arg Lys Gln Glu Ala
                420                 425                 430

Val Met Gly Lys Thr Leu Ser Leu Tyr Ser Gln Pro Phe Tyr Thr Gly
            435                 440                 445

Tyr Phe Gly Tyr Lys Met Cys Ala Arg Val Tyr Leu Asn Gly Asp Gly
            450                 455                 460

Met Gly Lys Gly Thr His Leu Ser Leu Phe Phe Val Ile Met Arg Gly
465                 470                 475                 480
```

```
Glu Tyr Asp Ala Leu Leu Pro Trp Pro Phe Lys Gln Lys Val Thr Leu
                485                 490                 495

Met Leu Met Asp Gln Gly Ser Ser Arg Arg His Leu Gly Asp Ala Phe
            500                 505                 510

Lys Pro Asp Pro Asn Ser Ser Ser Phe Lys Lys Pro Thr Gly Glu Met
            515                 520                 525

Asn Ile Ala Ser Gly Cys Pro Val Phe Val Ala Gln Thr Val Leu Glu
            530                 535                 540

Asn Gly Thr Tyr Ile Lys Asp Asp Thr Ile Phe Ile Lys Val Ile Val
545                 550                 555                 560

Asp Thr Ser Asp Leu Pro Asp Pro
                565

<210> SEQ ID NO 87
<211> LENGTH: 567
<212> TYPE: PRT
<213> ORGANISM: mus musculus

<400> SEQUENCE: 87

Met Glu Ser Ser Lys Lys Met Asp Ala Ala Gly Thr Leu Gln Pro Asn
1               5                   10                  15

Pro Pro Leu Lys Leu Gln Pro Asp Arg Gly Ala Gly Ser Val Leu Val
                20                  25                  30

Pro Glu Gln Gly Gly Tyr Lys Glu Lys Phe Val Lys Thr Val Glu Asp
            35                  40                  45

Lys Tyr Lys Cys Glu Lys Cys Arg Leu Val Leu Cys Asn Pro Lys Gln
50                  55                  60

Thr Glu Cys Gly His Arg Phe Cys Glu Ser Cys Met Ala Ala Leu Leu
65                  70                  75                  80

Ser Ser Ser Ser Pro Lys Cys Thr Ala Cys Gln Glu Ser Ile Ile Lys
                85                  90                  95

Asp Lys Val Phe Lys Asp Asn Cys Cys Lys Arg Glu Ile Leu Ala Leu
                100                 105                 110

Gln Val Tyr Cys Arg Asn Glu Gly Arg Gly Cys Ala Glu Gln Leu Thr
            115                 120                 125

Leu Gly His Leu Leu Val His Leu Lys Asn Glu Cys Gln Phe Glu Glu
130                 135                 140

Leu Pro Cys Leu Arg Ala Asp Cys Lys Glu Lys Val Leu Arg Lys Asp
145                 150                 155                 160

Leu Arg Asp His Val Glu Lys Ala Cys Lys Tyr Arg Glu Ala Thr Cys
                165                 170                 175

Ser His Cys Lys Ser Gln Val Pro Met Ile Lys Leu Gln Lys His Glu
            180                 185                 190

Asp Thr Asp Cys Pro Cys Val Val Ser Cys Pro His Lys Cys Ser
                195                 200                 205

Val Gln Thr Leu Leu Arg Ser Glu Leu Ser Ala His Leu Ser Glu Cys
        210                 215                 220

Val Asn Ala Pro Ser Thr Cys Ser Phe Lys Arg Tyr Gly Cys Val Phe
225                 230                 235                 240

Gln Gly Thr Asn Gln Gln Ile Lys Ala His Glu Ala Ser Ser Ala Val
                245                 250                 255

Gln His Val Asn Leu Leu Lys Glu Trp Ser Asn Ser Leu Glu Lys Lys
            260                 265                 270

Val Ser Leu Leu Gln Asn Glu Ser Val Glu Lys Asn Lys Ser Ile Gln
        275                 280                 285
```

```
Ser Leu His Asn Gln Ile Cys Ser Phe Glu Ile Glu Ile Glu Arg Gln
    290                 295                 300

Lys Glu Met Leu Arg Asn Asn Glu Ser Lys Ile Leu His Leu Gln Arg
305                 310                 315                 320

Val Ile Asp Ser Gln Ala Glu Lys Leu Lys Glu Leu Asp Lys Glu Ile
                325                 330                 335

Arg Pro Phe Arg Gln Asn Trp Glu Glu Ala Asp Ser Met Lys Ser Ser
            340                 345                 350

Val Glu Ser Leu Gln Asn Arg Val Thr Glu Leu Glu Ser Val Asp Lys
        355                 360                 365

Ser Ala Gly Gln Ala Ala Arg Asn Thr Gly Leu Leu Glu Ser Gln Leu
370                 375                 380

Ser Arg His Asp Gln Met Leu Ser Val His Asp Ile Arg Leu Ala Asp
385                 390                 395                 400

Met Asp Leu Arg Phe Gln Val Leu Glu Thr Ala Ser Tyr Asn Gly Val
                405                 410                 415

Leu Ile Trp Lys Ile Arg Asp Tyr Lys Arg Arg Lys Glu Ala Val
            420                 425                 430

Met Gly Lys Thr Leu Ser Leu Tyr Ser Gln Pro Phe Tyr Thr Gly Tyr
        435                 440                 445

Phe Gly Tyr Lys Met Cys Ala Arg Val Tyr Leu Asn Gly Asp Gly Met
450                 455                 460

Gly Lys Gly Thr His Leu Ser Leu Phe Phe Val Ile Met Arg Gly Glu
465                 470                 475                 480

Tyr Asp Ala Leu Leu Pro Trp Pro Phe Lys Gln Lys Val Thr Leu Met
                485                 490                 495

Leu Met Asp Gln Gly Ser Ser Arg Arg His Leu Gly Asp Ala Phe Lys
            500                 505                 510

Pro Asp Pro Asn Ser Ser Phe Lys Lys Pro Thr Gly Glu Met Asn
        515                 520                 525

Ile Ala Ser Gly Cys Pro Val Phe Val Ala Gln Thr Val Leu Glu Asn
530                 535                 540

Gly Thr Tyr Ile Lys Asp Asp Thr Ile Phe Ile Lys Val Ile Val Asp
545                 550                 555                 560

Thr Ser Asp Leu Pro Asp Pro
                565

<210> SEQ ID NO 88
<211> LENGTH: 464
<212> TYPE: PRT
<213> ORGANISM: gallus gallus

<400> SEQUENCE: 88

Met Asp Thr Ser Lys Lys Thr Glu Pro Pro Leu Ser Val Glu Met Val
1               5                   10                  15

Gln Gln Arg Ala Asn Pro Asp Arg Ser Pro Ser Ala Ser Ile Tyr Val
                20                  25                  30

Pro Glu Gln Gly Gly Tyr Lys Glu Lys Phe Val Asn Ala Val Glu Asp
            35                  40                  45

Lys Tyr Lys Cys Glu Lys Cys His Phe Ile Leu Cys Asn Pro Lys Gln
    50                  55                  60

Thr Glu Cys Gly His Arg Phe Cys Glu Thr Cys Met Asn Ala Leu Leu
65                  70                  75                  80

Ser Thr Pro Ser Pro Lys Cys Thr Ala Cys Gln Glu Ser Ile Val Lys
                85                  90                  95
```

```
Asp Lys Val Phe Lys Asp Asn Cys Cys Arg Arg Glu Leu Leu Ala Leu
            100                 105                 110

Gln Ile Tyr Cys Arg Asn Glu Asn Lys Gly Cys Lys Glu Gln Leu Ser
        115                 120                 125

Leu Gly Gln Leu Leu Met His Leu Lys Thr Asp Cys Gln Phe Glu Glu
130                 135                 140

Leu Pro Cys Pro Arg Ala Asp Cys Lys Glu Lys Ile Leu Arg Lys Asp
145                 150                 155                 160

Leu Pro Asp His Val Glu Lys Thr Cys Lys Tyr Arg Glu Thr Thr Cys
                165                 170                 175

Lys Tyr Cys Lys Ser Gln Val Pro Met Ile Met Leu Gln Lys His Glu
            180                 185                 190

Asp Thr Asp Cys Pro Cys Val Met Val Ser Cys Pro His Lys Cys Ser
        195                 200                 205

Val Lys Thr Leu Met Arg Ser Glu Arg Val Ile Asp Ser Gln Ala Glu
    210                 215                 220

Lys Leu Lys Glu Leu Asp Lys Glu Ile Arg Pro Phe Arg Gln Asn Trp
225                 230                 235                 240

Glu Glu Ala Asp Ser Met Lys Ser Ser Val Glu Ser Leu Gln Asn Arg
                245                 250                 255

Val Thr Glu Leu Glu Ser Val Asp Lys Thr Ala Gly Gln Gly Ala Arg
            260                 265                 270

Asn Thr Ser Met Leu Glu Thr Gln Leu Ser Arg His Asp Gln Met Leu
        275                 280                 285

Ser Val His Asp Ile Arg Leu Ala Asp Met Asp Leu Arg Phe Gln Val
    290                 295                 300

Leu Glu Thr Ala Ser Tyr Asn Gly Val Leu Ile Trp Lys Ile Arg Asp
305                 310                 315                 320

Tyr Lys Arg Arg Lys Gln Glu Ala Val Met Gly Lys Thr Leu Ser Leu
                325                 330                 335

Tyr Ser Gln Pro Phe Tyr Thr Gly Tyr Phe Gly Tyr Lys Met Cys Ala
            340                 345                 350

Arg Val Tyr Leu Asn Gly Asp Gly Met Gly Lys Gly Thr His Leu Ser
        355                 360                 365

Leu Phe Phe Val Ile Met Arg Gly Glu Tyr Asp Ala Leu Leu Pro Trp
    370                 375                 380

Pro Phe Lys Gln Lys Val Thr Leu Met Leu Met Asp Gln Gly Pro Ser
385                 390                 395                 400

Arg Arg His Leu Gly Asp Ala Phe Lys Pro Asp Pro Asn Ser Ser Ser
                405                 410                 415

Phe Lys Lys Pro Thr Gly Glu Met Asn Ile Ala Ser Gly Cys Pro Val
            420                 425                 430

Phe Val Ala Gln Thr Val Leu Glu Asn Gly Thr Tyr Ile Lys Asp Asp
        435                 440                 445

Thr Ile Phe Ile Lys Val Ile Val Asp Thr Ser Asp Leu Pro Asp Pro
    450                 455                 460

<210> SEQ ID NO 89
<211> LENGTH: 573
<212> TYPE: PRT
<213> ORGANISM: danio rerio
```

<400> SEQUENCE: 89

```
Met Ser Ala Gly Arg Asn Val Glu Gln Gln Ile Pro Leu Gln Gln Arg
1               5                   10                  15

Pro Pro Ser Leu Ala Met Pro Ser Met Ala Gln Arg Pro Arg Pro Glu
            20                  25                  30

Pro Gly Phe Ser Pro Leu His Gly Gly Phe Arg Asp His Phe Val Thr
        35                  40                  45

Thr Pro Glu Pro Lys Tyr Cys Cys Glu Thr Cys Arg Leu Val Leu Cys
    50                  55                  60

Asn Pro Arg Gln Thr Glu Cys Gly His Arg Phe Cys Glu Ser Cys Ile
65                  70                  75                  80

Asn Glu Leu Leu Ser Lys Pro Asn Pro Val Cys Pro Ala Asp Leu Leu
                85                  90                  95

Pro Leu Phe Glu Asp Lys Ile Phe Arg Asp Val Cys Cys Asn Arg Glu
            100                 105                 110

Ile Met Ala Leu Lys Val Tyr Cys Arg Ser Glu Lys Asn Gly Cys Lys
            115                 120                 125

Glu Gln Met Cys Leu Gln Gln Val Met Glu His Leu Val Ile Cys Pro
130                 135                 140

Tyr Phe Glu Val Pro Cys Pro Leu Gly Lys Cys Lys Glu Lys Met Met
145                 150                 155                 160

Arg Lys Asp Met Pro Glu His Leu Ser Arg Lys Cys Lys His Arg Glu
                165                 170                 175

Val Thr Cys Glu Phe Cys Ser Leu Lys Met Ala Leu Thr Glu Leu Gln
            180                 185                 190

Lys His Lys Glu Thr Val Cys Pro Ala Phe Pro Val Ala Cys Pro Asn
        195                 200                 205

His Cys Ser Phe Ser Ser Ile Leu Arg Ser Glu Leu Ser Ser His Gln
210                 215                 220

His Asp Cys Pro Lys Ala Gln Val Thr Cys Ser Phe Ile Arg Tyr Gly
225                 230                 235                 240

Cys Ser Tyr Lys Gly Leu Asn Gln Glu Met Arg Glu His Glu Ser Ser
                245                 250                 255

Phe Ala Ser Glu His Leu Arg Met Met Ala Val Arg Asn Thr Thr Leu
            260                 265                 270

Glu Ala Lys Val Glu Asp Val Lys Ser Glu Leu Met Glu Arg Tyr Lys
        275                 280                 285

Val Leu Pro Ser Leu Ser Ser Arg Leu Ala Glu Val Glu Arg Gln Tyr
    290                 295                 300

Glu Glu Met Arg Glu Lys Asn Arg Gln Leu Glu Gln Lys Leu Val Ser
305                 310                 315                 320

Met Gln Met Leu Met Ser Ser His Ser Glu Lys Leu Leu Glu Val Glu
                325                 330                 335

Met Glu Leu Arg Glu Leu Arg Pro Leu Arg Ala Met Arg Glu Glu Val
            340                 345                 350

Glu Thr Leu Arg Gly Ser Val Glu Ser Met Arg Ser Met Val Ser Ser
        355                 360                 365

Leu Asp Ser Ser Cys Val Asn Ser Ala Ser Gly Ser His Thr Leu Ala
    370                 375                 380

Ser Leu Glu Gln Gln Leu Thr Arg His Asp Asp Leu Met Ser Val His
385                 390                 395                 400

Asp Val Arg Leu Ala Glu Met Asp Leu Lys Leu Gln Val Leu Glu Thr
                405                 410                 415
```

```
Ala Ser Phe Asn Gly Thr Leu Ile Trp Lys Ile Arg Asp Tyr Lys Arg
                420                 425                 430

Arg Lys Gln Glu Ala Val Val Ser Lys Thr Leu Ser Leu Tyr Ser Gln
            435                 440                 445

Pro Phe Tyr Thr Gly Tyr Phe Gly Tyr Lys Met Cys Ala Arg Val Tyr
        450                 455                 460

Leu Asn Gly Asp Gly Met Gly Lys Gly Thr His Leu Ser Leu Phe Phe
465                 470                 475                 480

Val Val Met Arg Gly Glu Tyr Asp Ala Leu Leu Gln Trp Pro Phe Lys
                485                 490                 495

Gln Lys Val Thr Leu Met Leu Met Asp Gln Gly Pro Ala Arg Lys His
            500                 505                 510

Leu Gly Asp Ala Phe Lys Pro Asp Pro Ser Ser Ser Phe Arg Arg
        515                 520                 525

Pro Thr Gly Glu Met Asn Ile Ala Ser Gly Cys Pro Leu Phe Val Ala
530                 535                 540

Gln Thr Val Leu Glu Asn Gly Thr Tyr Ile Lys Asp Asp Thr Ile Phe
545                 550                 555                 560

Ile Lys Val Thr Val Asp Thr Ser Asp Leu Pro Asp Pro
                565                 570

<210> SEQ ID NO 90
<211> LENGTH: 561
<212> TYPE: PRT
<213> ORGANISM: Eptatretus burgeri

<400> SEQUENCE: 90

Met Val Pro Ala Leu Gly Ile Cys Phe Pro Lys Val Pro Leu Arg Ser
1               5                   10                  15

Arg Pro Leu Gln Ile Ser Trp Pro Pro Leu Arg Gly Tyr Ala Tyr Asn
            20                  25                  30

Phe Val Glu Thr Pro Pro Ala Lys Tyr Cys Cys Gly Val Cys Ser Leu
        35                  40                  45

Pro Leu Arg Glu Ala His Gln Thr Gly Cys Gly His Arg Leu Cys Arg
50                  55                  60

Ser Cys Ala Asp Gly Leu Leu Thr Glu Thr Asn Pro Gln Cys Pro Glu
65                  70                  75                  80

Cys Ser Glu Pro Leu Asp Gln Lys Gln Val Tyr Arg Asp Thr Cys Cys
                85                  90                  95

Asn Arg Glu Ile Leu Asn Leu His Val Phe Cys Pro Asn Glu Ala Ser
            100                 105                 110

Gly Cys Cys Glu Thr Met Val Leu His Lys Leu Leu Val His Leu Asp
        115                 120                 125

Thr Cys Pro Tyr Glu Leu Val Ala Cys His Asn Asp Ala Cys Ser Met
        130                 135                 140

His Leu Ala Arg Leu Tyr Met Pro Gln His His Gly Thr Cys Pro Phe
145                 150                 155                 160

Arg Leu Glu Phe Cys Lys Phe Cys Ser Ala Pro Val Pro Cys Val Gln
                165                 170                 175

Leu Glu Glu His Lys Gln Thr Cys Pro Lys Tyr Leu Pro Cys Pro
            180                 185                 190

Asn Asn Cys Asp Glu His Gly Ile Pro Arg Asn Glu Leu Glu Lys His
        195                 200                 205

Leu Val Gln Cys Ala Leu Thr Glu Gln Pro Cys Ser Phe His Arg Phe
210                 215                 220
```

```
Gly Cys Asp Phe Lys Ala Cys Gly Lys Gly Val Ser Glu His Glu Ala
225                 230                 235                 240

Gly Ser Val Pro Gln His Leu Leu Val Leu Arg Lys His Thr Glu
            245                 250                 255

Leu Gln Glu Thr Leu Gly Gln Val Gln Gly Leu Glu Gln Lys Ala
        260                 265                 270

Ser Val Phe Glu Gln Met Gln Leu Arg Leu Glu Arg Ala Glu Arg Asp
        275                 280                 285

Ala Glu His Trp Gly Lys Leu Val Ser Lys Asn Glu Ala Ser Leu Thr
    290                 295                 300

Ser Thr Met Glu Lys Val Thr Ser Gln Thr Lys Arg Met Gln Val Leu
305                 310                 315                 320

Glu Lys Leu Trp Glu Ser Ser Asn Gly Leu Ser Thr Met Ser Leu Glu
                325                 330                 335

Ser Ser Arg Ser Arg Glu Cys His Asp Asn Leu Lys Gly Val Arg Gln
            340                 345                 350

Met Leu Glu Val Val Lys Thr Arg Leu Ser Thr Leu Gly Ser Leu Gln
        355                 360                 365

Ser Thr Val Gly Thr Met Glu Lys Thr Leu Gln Thr His Glu Ser Leu
370                 375                 380

Leu Pro Val His Thr Gln Arg Leu Ala Asp Thr Asp Leu Arg Phe Gln
385                 390                 395                 400

Leu Leu Glu Thr Val Ser Cys Ser Gly Arg Leu Val Trp Lys Leu Thr
                405                 410                 415

Asp Tyr Ala Gln Arg Lys Gln Asp Ala Thr Thr Gly Ile Thr Pro Ser
            420                 425                 430

Leu Tyr Ser Gln Pro Phe Tyr Thr Thr Thr Phe Gly Tyr Lys Met Cys
        435                 440                 445

Ala Arg Val Tyr Leu Asn Gly Asp Gly Val Gly Arg Gly Thr His Leu
    450                 455                 460

Ser Leu Phe Phe Val Val Met Arg Gly Glu Tyr Asp Thr Ile Leu Ser
465                 470                 475                 480

Trp Pro Phe Arg Gln Arg Val Thr Leu Met Leu Leu Asp Gln Gly Pro
                485                 490                 495

Gly Arg Lys His Leu Ser Asp Thr Phe Lys Pro Asp Pro Thr Ser Ser
            500                 505                 510

Ser Phe Lys Arg Pro Thr Ser Glu Met Asn Val Ala Ser Gly Cys Pro
        515                 520                 525

Met Phe Val Ser His Gly Val Leu Glu Ser Arg Thr Tyr Leu Lys Asp
    530                 535                 540

Asp Ser Ile Phe Leu Ser Ile Val Val Asp Arg Thr Gly Leu Asp Asp
545                 550                 555                 560

Leu

<210> SEQ ID NO 91
<211> LENGTH: 540
<212> TYPE: PRT
<213> ORGANISM: pinctada fucata

<400> SEQUENCE: 91

Met Cys Lys Ile Cys Asn Asp Val Leu Arg Asp Ala Val Gln Thr Phe
1               5                   10                  15

Cys Gly His Arg Ile Cys Leu Gln Cys Ile Asp Gln Ala Leu Gln Gly
            20                  25                  30
```

-continued

```
Arg Glu Ser Ile Pro Cys Pro Ala Lys Glu Gly Cys Val Asp Leu
             35                  40                  45
Lys Arg Glu Glu Ile Asn Arg Asp Ser Ser Ala Arg Arg Glu Val Arg
 50                  55                  60
Ala Leu Asp Val Phe Cys Pro Phe Glu Asp Gly Gly Cys Lys Lys Thr
 65                  70                  75                  80
Leu Gln Trp Lys Asp Leu Gln Thr His Glu Glu Thr Cys Glu Phe Arg
                 85                  90                  95
Pro Val Pro Cys Pro Asn Tyr Leu His Gly Cys Glu Val Ile Ile Ser
                100                 105                 110
Tyr Lys Asp Val Asp Glu His Leu Lys Glu Cys Pro Tyr Arg Pro Tyr
             115                 120                 125
Arg Cys Gln Phe Cys Asn Gln Glu Val Pro Leu Ala Leu Lys Gln Gln
         130                 135                 140
His Glu Thr Glu Thr Cys Pro Arg Ile Pro Ile Pro Cys Arg Tyr Glu
145                 150                 155                 160
Cys Gly Ile Asn Pro Leu Pro Arg Glu Glu Leu Glu Ala His Leu Ile
                165                 170                 175
Thr Cys Pro Lys Arg Pro Gln Arg Cys Arg Tyr His Ser Val Gly Cys
             180                 185                 190
Thr Phe Glu Gly Thr Ser Glu Glu Val Gln Gln His Glu Arg Asp Asp
         195                 200                 205
Thr Asp Arg His Leu Glu Leu Ile Thr Met Tyr Thr Ala Asn Met Asp
     210                 215                 220
Leu Gln Ser Leu Glu Val Arg Arg Glu Leu Gln Asp Met Ser Leu Glu
225                 230                 235                 240
Arg Asp Asn Ser Arg Arg Leu Leu Asp Asp Val Ser Arg Gln Met Ala
                245                 250                 255
Glu Ile Lys Arg Ser Met Asp Asp Met Lys Ile Gln Val Arg Asp Val
             260                 265                 270
Lys Leu Lys Ile Val Ser Gln Thr Glu Arg Ile Ile His Val Glu Arg
         275                 280                 285
Lys Val Glu Asp Leu Ala Lys Lys Asp Ser Val Asp Arg His Ala Arg
     290                 295                 300
Asp Leu Gln Val Ile Arg Glu Thr Gln Ala Ser Met Ser Glu Arg Ile
305                 310                 315                 320
Arg Gln Leu Glu Gly Arg Ala Pro Ser Gln Gly Asn Pro Ala Val Pro
                325                 330                 335
Ala Ile Glu Gly Asn Thr Gly Ser Val Val Pro Gln Val Gln Gln His
             340                 345                 350
Glu Arg Gln Leu Gly Leu Gln Asp Ile Arg Leu Ala Glu Leu Asp Leu
         355                 360                 365
Arg Phe Gln Val Leu Glu Thr Ala Ser Tyr Asp Gly Thr Leu Ile Trp
     370                 375                 380
Lys Ile Lys Asp Tyr Ser Arg Arg Lys Gln Asp Ala Ile Thr Gly Arg
385                 390                 395                 400
Thr Leu Ser Leu Tyr Ser Gln Pro Phe Tyr Thr Ser Arg Thr Gly Tyr
                405                 410                 415
Lys Met Cys Ala Arg Val Tyr Leu Asn Gly Asp Gly Met Gly Arg Gly
             420                 425                 430
Thr His Leu Ser Leu Phe Phe Val Ile Met Arg Gly Glu Tyr Asp Thr
         435                 440                 445
```

```
Leu Leu Ser Trp Pro Phe Lys Gln Lys Val Thr Leu Met Leu Leu Asp
450                 455                 460
Gln Asp Thr Gly Thr Arg His Leu Ser Asp Thr Phe Arg Pro Asp Pro
465                 470                 475                 480
Ser Ser Ser Ser Phe Arg Lys Pro Thr Thr Glu Met Asn Val Ala Ser
                485                 490                 495
Gly Cys Pro Leu Phe Val Ser His Ala Val Leu Glu Thr Arg Thr Tyr
            500                 505                 510
Val Arg Glu Asp Thr Ile Phe Ile Lys Ile Ile Val Asp Thr Glu Gly
            515                 520                 525
Leu Tyr Glu Asp Ser Ile Leu Lys Glu Arg Arg Ser
530                 535                 540

<210> SEQ ID NO 92
<211> LENGTH: 637
<212> TYPE: PRT
<213> ORGANISM: Strongylocentrotus purpuratus

<400> SEQUENCE: 92

Met Pro Phe Lys Asp Glu Thr Ala Leu Met Asn Asn Thr His Ser Glu
1               5                   10                  15
Ser Val Ile Ile Ile Tyr Leu Ile Leu Gly Ser Leu Ile Asn Phe Thr
                20                  25                  30
Thr Leu Ala Ser Leu Phe Ser Lys Ser Gly Ile Leu His Leu Gln Ala
            35                  40                  45
Ile Phe Cys His Gln Ala Gln Gln Arg Ser Ala Ser Leu Phe Tyr Leu
        50                  55                  60
Gly Ile Lys Lys Ser Arg His Arg Phe Val Leu Ser Ser Met Ala Glu
65                  70                  75                  80
Lys Gly Ala Glu Val Asn Pro Ser Ile Arg Ser Leu Gln Ser Asp Thr
                85                  90                  95
Gly Glu Leu Glu Gly Gln Pro Gly Ser Gly Ala Ser Phe Gln Gly Ala
            100                 105                 110
Ser Pro Pro Pro Ser Tyr Leu Glu Leu Pro Gly Tyr Ser Thr Asn Ile
        115                 120                 125
Phe Lys Ser Pro Pro Ser Glu Gly Tyr Ile Cys Gly Ile Cys Ala Gln
130                 135                 140
Val Val Arg Trp Pro Val Gln Thr Asp Cys Ala Cys Gly Leu Phe Cys
145                 150                 155                 160
His Gly Cys Leu His Arg Tyr Ile Gly Asp Glu Thr Gly Ser Leu Glu
                165                 170                 175
Cys Pro Arg Cys His Asp Met Phe Pro Thr Thr Glu Thr Gln Arg Asp
            180                 185                 190
Lys Ile Ala His Lys Lys Leu Leu Lys Leu Asp Ile Ile Cys Pro His
        195                 200                 205
Gly Cys Gly Thr Asp Met Leu Leu Arg Asp Leu Asp Lys His Glu Glu
210                 215                 220
Glu Cys Ser Phe Val Ile Ile Glu Cys Ile His Lys His Gln Gly Cys
225                 230                 235                 240
Lys Glu Leu Ile Lys Arg Ile Asp Leu Val Lys His Leu Glu Thr Gln
                245                 250                 255
Cys Asp Phe Arg Lys Glu Ser Cys Gln His Cys Gly Gln Gln Phe Ile
            260                 265                 270
Ala Thr Glu Leu Glu Lys His Glu Lys Val Cys Ala Phe Thr Glu Ser
        275                 280                 285
```

```
Val Thr Lys Val Leu Met Ala Lys Gly Gly Asp Gly Glu Gly Ala Gly
    290                 295                 300

Ala Ala Ser Glu Gln Val Val Thr Gln Glu Leu Met Lys Thr Val Ala
305                 310                 315                 320

Ile Asn Leu Glu Ala Lys Ile Ala Glu Val Arg Arg Ile Met Thr Glu
                325                 330                 335

Ile Asp Asn Gln Gly Lys Val Leu Lys Lys Leu Tyr Glu Asp Ser Arg
                340                 345                 350

Ala Thr Ile Asn Lys Asn Thr Asp Asn Leu Ser Asp Val Asp Lys Ser
                355                 360                 365

Val Lys Gln Leu Gln Lys Met Val Leu Thr Lys Leu Ser Lys Leu Pro
    370                 375                 380

Asp Ile Glu Arg Ser Val Gly Thr Ser Leu Ser Arg Thr Glu Phe Glu
385                 390                 395                 400

Ser His Lys Glu Ser Val Gln Gly Ile Arg Glu Leu Asp Ser Gln
                405                 410                 415

Lys Thr Arg Ile Ser Glu Leu Glu Asp Gln Ser Ser Gly Thr Ile
                420                 425                 430

Gly Gly Ser Gly Glu Gly Ile Ser Lys His Leu Lys Asp Gln Ile Ala
                435                 440                 445

Asn Asn Thr Glu Lys Val Asn Tyr Phe Asp Asp Gln Ile Asn Met Tyr
    450                 455                 460

Ser Met Arg Leu Ala Glu His Glu Leu Arg Phe Gln Phe Gln Glu Thr
465                 470                 475                 480

Ala Ser Tyr Asp Gly Thr Leu Ile Trp Lys Ile Lys Glu Phe Ala Arg
                485                 490                 495

Arg Lys Arg Asp Ala Asp Asn Gly Lys Thr Leu Ser Leu Tyr Ser Gln
                500                 505                 510

Pro Phe Tyr Thr Ser Arg Phe Gly Tyr Lys Met Cys Ala Arg Ile Tyr
                515                 520                 525

Leu Asn Gly Asp Gly Ile Gly Lys Gly Thr His Val Ser Leu Phe Phe
    530                 535                 540

Val Val Met Lys Gly Asp Tyr Asp Ala Leu Leu Pro Trp Pro Phe Ser
545                 550                 555                 560

Gln Lys Val Thr Leu Met Leu Leu Asp Gln Glu Thr Gly Arg His
                565                 570                 575

Leu Ser Asp Ser Phe Arg Pro Asp Pro Thr Ser Thr Ser Phe Gln Arg
                580                 585                 590

Pro Ser Thr Asn Met Asn Ile Ala Ser Gly Cys Pro Leu Phe Val Ser
                595                 600                 605

Gln Ser Val Leu Lys Asp Pro Ala Tyr Val Lys Glu Asp Thr Ile Phe
    610                 615                 620

Ile Lys Val Val Val Asp Thr Thr Asp Leu Tyr Gly Pro
625                 630                 635

<210> SEQ ID NO 93
<211> LENGTH: 531
<212> TYPE: PRT
<213> ORGANISM: Nematostella vectensis

<400> SEQUENCE: 93

Met Gln Asp Glu Gly Phe Gln Thr Glu Leu Phe Val Glu Pro Leu Asp
1               5                   10                  15

Pro Lys Tyr Arg Cys Pro Val Cys Gly Asn Ala Leu Lys His Pro Val
                20                  25                  30
```

-continued

Gln Thr Pro Cys Gly His Arg Phe Cys Glu Gly Cys Leu Glu Pro Ile
 35                  40                  45

Leu Arg Gly Pro Ser Lys Cys Pro Val Asp Gly Glu Glu Leu Lys Ile
 50                  55                  60

Asp Gly Val Phe Lys Asp Val Cys Cys Arg Arg Glu Ile Leu Cys Leu
 65                  70                  75                  80

Ala Cys Tyr Cys Pro Asn Arg Gln Leu Gly Cys Glu Trp Met Lys Asp
                 85                  90                  95

Leu Gln Tyr Leu Glu Glu His Arg Ala Asn Cys Glu Tyr Lys Gly Val
             100                 105                 110

Gln Cys His Asn Pro Gly Cys Gln Glu Lys Val Ala Lys Arg Asp Leu
         115                 120                 125

Glu Ala His Leu Glu Arg Cys Glu Phe Lys Pro Ser Asp Cys Gln Tyr
     130                 135                 140

Cys Leu Gln Arg Ile Pro Ala Ala Ser Met Glu Asp His Leu Gln Thr
145                 150                 155                 160

Cys Glu Lys His Pro Val Val Cys Pro His Cys Gly Ala Glu Gly Ile
                165                 170                 175

Cys Arg Asp Glu Leu Leu His His Gln Thr Asn Ile Cys Glu Gln Ala
            180                 185                 190

Glu Leu Pro Cys Ser Phe Ala Lys His Gly Cys His Phe Lys Gly Thr
        195                 200                 205

Arg Glu Ala Leu Glu Thr His Phe Arg Asp Gln Ala Ser Val His Val
    210                 215                 220

Asn Leu Leu Leu Thr Ala Thr Gln Asn Glu Glu Lys Ala Arg Ser Glu
225                 230                 235                 240

Met Ala Ala Lys Leu Ser Gln Met Glu Lys Glu Arg Ala Lys Gln Gln
                245                 250                 255

Glu Gln Met Tyr Glu Gln Arg Glu Ala Leu Ala Val Ala Asn Gln Asn
            260                 265                 270

Leu Arg Thr Tyr Gln Gly Lys Leu Asn Val Ile Glu Arg Ser Val Ala
        275                 280                 285

Glu Gln Arg Arg Glu Leu Ala Glu Leu Lys Glu Arg Ile Gln Leu Gln
    290                 295                 300

Glu Val Glu Ala Ala Ile Arg Glu Gln Asp Arg Arg Leu Gly Met Ile
305                 310                 315                 320

Glu Asn Glu Ala Ser Arg Gly Ala Ala Pro Ser Ser Gly Pro Gly Ser
                325                 330                 335

Met Gly Gly Thr Met Ala Leu Glu Arg Arg Gln Asp Arg Asn Glu His
            340                 345                 350

Gln Leu Ala Leu His Asp Ile Gln Leu Ala Glu His Asp Leu Lys Leu
        355                 360                 365

Gln Met Leu Glu Ala Thr Ser Tyr Asp Gly Thr Tyr Ile Trp Lys Ile
    370                 375                 380

Asp Glu Tyr Thr Arg Arg Tyr Gln Glu Gly Val Ser Gly Lys Thr Pro
385                 390                 395                 400

Ser Ile Tyr Ser Pro Pro Phe Tyr Val Gly Arg Tyr Gly Tyr Lys Ala
                405                 410                 415

Cys Ala Arg Val Tyr Pro Asn Gly Asp Gly Met Gly Lys Gly Ser His
            420                 425                 430

Leu Ser Leu Phe Phe Val Leu Met Arg Gly Glu Phe Asp Ala Leu Leu
        435                 440                 445

```
-continued

Pro Trp Pro Phe Arg Gln Lys Val Thr Phe Lys Leu Leu Asp Gln Asp
    450             455             460

Arg Val His Asp Ile Gly Asp Thr Phe Arg Pro Asp Pro Thr Ser Ser
465             470             475             480

Ser Phe Lys Arg Pro Thr Ser Asn Met Asn Ile Ala Ser Gly Cys Pro
                485             490             495

Leu Phe Ile Ser His Thr Asn Leu Gln Thr Arg Ala Tyr Val Arg Asp
            500             505             510

Asp Thr Met Phe Ile Lys Ile Ala Val Asp Thr Thr Gly Leu Pro Pro
        515             520             525

Met Gly Phe
    530
```

PEPTIDES AND METHODS RELATED TO ICOS SIGNALING

CROSS-REFERENCE TO RELATED PATENT APPLICATIONS

This patent application is a national stage entry under U.S.C. § 371 International Application No. PCT/US2016/067375 filed Dec. 16, 20216, which in turn, claims the benefit of, and priority to, U.S. Provisional Patent Application No. 62/267,954 filed on Dec. 16, 2015. The entire content of the foregoing application is incorporated herein by reference, including all text, tables, and drawings.

STATEMENT REGARDING FEDERALLY SPONSORED RESEARCH OR DEVELOPMENT

This invention was made with government support under NIH grants CA 35299, A1109976, A1063107, and A1072543. The government has certain rights in the invention.

The entire content of the foregoing application is incorporated herein by reference, including all text, tables, and drawings.

REFERENCE TO A "SEQUENCE LISTING," A TABLE, OR A COMPUTER PROGRAM LISTING APPENDIX

Sequence Listing file Name: 116639-0260_SL
Sequence Listing file Size: 114,839 bytes
The entire contents of the sequence listing are hereby expressly incorporated by reference which has been submitted electronically in ASCII format. Said ASCII copy was created on Jun. 15, 2022.

BACKGROUND

The inducible costimulatory (ICOS) protein serves an important function in the regulation of T-cell dependent immune responses. ICOS is significant in regulating cytokine production from recently activated T-cells. ICOS delivers an important signal for T cell-dependent B cell activation in a secondary immune response. ICOS contributes in part to a Th2 and not Th1 effector function when highly differentiated T helper cells are generated. (See Coyle et al., Immunity, (2000) 13:95-105, the entire contents of which are hereby incorporated by reference). ICOS ligation, for instance, fails to provide a costimulatory signal for IL-2 production. ICOS is also overexpressed in Th2 effector cells, and binding of ICOS by an antibody reduced IL-5 and IL-13 secretion, and inhibited cytokine production from Th2, but not Th1 cells (in a dose-dependent manner).

Furthermore, ICOS serves a particularly important function in the development of B cells by T follicular helper cells.

The process of diversifying antigen receptors intrinsically carries the risk of self-antigen recognition, leading to destruction of self-tissues and autoimmune manifestations. One of the safeguard mechanisms is to insulate the Ab-generating machinery to a specialized anatomical compartment, known as the germinal center (GC), embedded within secondary lymphoid organs, such as the spleen, lymph nodes, tonsils and Peyer's patches. Inside GCs, B cells undergo successive rounds of random somatic hypermutation, affinity maturation and isotype class switching. Only B cells expressing the high-affinity, class-switched Abs specific for the immunizing antigen are licensed to exit the GCs and to survive as long-lived plasma cells and/or memory B cells. Guiding B cells through these stochastic events is a subset of $CD4^+$ T helper cells, known as T follicular helper (Tfh) cells.

In secondary lymphoid organs, B and T cells are organized orderly into B cell follicles and T cell zones, based on the gradients of CXCL13 and CCL19/21 chemokines, respectively. Homing of T cells into B-cell follicles requires the concomitant up-regulation of the CXCL13-binding CXCR5 chemokine receptor, and the down-regulation of CCL19/21-responding CCR7 chemokine receptor. This preconditioning process occurs at the priming stage during the interaction between dendritic cells (DC) and naïve T cells. Additionally, during the priming phase, T cells conditioned to enter B-cell follicles acquire a distinct transcriptional profile by up-regulating B-cell lymphoma 6 (Bcl6), the canonical transcription factor of Tfh cells, and repressing the expression of BLIMP1. The $CXCR5^+Bcl6^+CD4^+$ T cells, hereafter dubbed nascent Tfh cells, which appear as early as 2-3 days after viral infection or protein immunization, migrate to the T-B border. At this site, contiguous interaction between nascent $CXCR5^+Bcl6^+$ Tfh cells and cognate B cells allows for further maturation of Tfh cells. Fully mature Tfh cells, hereafter dubbed GC Tfh cells, are crucial to support the production of high-affinity Abs. GC Tfh cells are distinguishable from nascent Tfh cells by the elevated expression of multiple markers, including the PD-1 receptor.

The ICOS-ICOSL receptor-ligand pair is essential. Homozygous ICOS loss is found in patients suffering from common variable immunodeficiency with a concomitant decrease in $CXCR5^+$ memory Tfh cells in blood and GC reactions. Similarly, $Icos^{-/-}$ and $Icosl^{-/-}$ mice have defective GCs, impaired humoral response to antigens, and lack immunological memory. ICOS-ICOSL engagement generates co-stimulatory signals that not only allows the ultimate effector Tfh program, but also drives the motility of Tfh cells deep into the B-cell follicles, and promotes B-cell positive selection and affinity maturation in GCs.

While ICOS is clearly essential for most Tfh cell and GC functions, the molecular basis for why ICOS is so critical for Tfh cell development and function remains relatively unclear. To date, phosphoinositide-3-kinase (PI3K) is the only signaling molecule known to interact with the short cytoplasmic tail of ICOS via the YxxM motif. However, PI3K associates with, and signals from, other cell surface receptors, including CD28 and CTLA-4. Furthermore, studies exploring the importance of the association between PI3K and ICOS in T cell biology have revealed that disruption of the ICOS-PI3K interaction, or selective deletion of PI3K components from T cells, do not result in a full phenocopy of $Icos^{-/-}$ knockout animals. These studies implied that ICOS-dependent, but PI3K-independent, signaling pathways mediated by other, unknown ICOS-interacting signaling molecules, are involved in ICOS signaling.

Thus, the present disclosure relates to methods and compositions useful for initiating and propagating ICOS-mediated signaling. In particular, the present disclosure provides three peptide motifs which promote ICOS binding and whose ablation leads to modulated ICOS signaling or signaling mediated by TBK1, IRF4, IKKβ, or TBKBP1. The binding these peptide motifs or the addition of such motifs as co-stimulatory agents leads to modulated immune responses, and provides new and unexpected therapies for neurodegenerative, autoimmune, metabolic, cancer or inflammatory conditions.

SUMMARY OF THE INVENTION

The invention will be briefly described by use of the following non-limiting embodiments. A skilled artisan would understand how such embodiments may be modified and combined to demonstrate specific aspects of the present invention. As such, each embodiment may be combined with other embodiments as understood by the skilled artisan.

A first embodiment includes one or more peptides comprising ICOS motifs. This includes motifs such as those specifically shown in the figures and sequence listings, and their orthologous counterparts. In particular aspects, these peptides include:
  a) SEQ ID NO:18;
  b) SEQ ID NO: 19;
  c) SEQ ID NO: 20;
  d) any of SEQ ID NO: 24-26, 29, 31-33, 37, 38 and 40-58;
  e) at least two of SEQ ID NO:18, SEQ ID NO: 19, SEQ ID NO: 20 and SEQ ID NO: 24-26, 29, 31-33, 37, 38 and 40-58; or
  f) each of SEQ ID NO:18, SEQ ID NO: 19 and SEQ ID NO: 20.

In a second embodiment, the invention includes modified ICOS protein comprising, where the amino acid sequence of ICOS has been modified by addition, deletion or substitution of amino acid residues. In particular aspects, these modified ICOS proteins include:
  a) A protein sequence comprising any of SEQ ID NOs: 1-17, where one or more amino acids have been added, deleted or substituted;
  b) A protein sequence having at least 80%, at least 85%, at least 90%, at least 92%, at least 95%, or at least 99% sequence identity to any of SEQ ID Nos: 1-17;
  c) A protein sequence of any of SEQ ID Nos: 1-17, where one or more amino acids have been added, deleted, or substituted in the cytoplasmic domain;
  d) a protein sequence comprising SEQ ID NO: 1, where one or more amino acid residues are added, deleted, or substituted at amino acid positions amino acid positions 170-179, 180-184, or 186-193;
  e) a protein sequence comprising SEQ ID NO: 1, substituted at amino acid position 170179 with X1SSX2X3X4PX5X6X7, where X1 may be absent or present, and if present X1 is any amino acid, and X2-7 may be any amino acid (SEQ ID NO: 18), substituted at positions 180-183 with YX1X2M where X1 and X2 may be any amino acid, (SEQ ID NO: 19), or substituted at amino acid positions 186-193, with XVNTAKK, where X may be any amino acid (SEQ ID NO: 20);
  f) a protein sequence comprising SEQ ID NO: 1, substituted at amino acid position 170179 with X1SSX2X3X4PX5X6X7, where X1 may be absent or present, and if present may be S; X2, X3, X4, X5; and X6 may be any amino acid and X7 is D or E (SEQ ID NO: 18), substituted at positions 180-183 with YX1X2M where X1 and X2 may be any amino acid, but X1 preferably is M, X2 may be any amino acid but preferably is F or P (SEQ ID NO: 19), or substituted at amino acid positions 186-193, with XVNTAKK, where X may be A or S (SEQ ID NO: 20);
  g) a truncated ICOS protein wherein the protein includes amino acids 1-169 of SEQ ID NO: 1, amino acids 1-179 of SEQ ID NO: 1, or amino acids 1-185 of SEQ ID NO: 1, but less than the full-length ICOS protein, and their orthologous counterparts; and
  h) peptides having from about 19 to about 100 amino acid residues, about 20 to about 100 amino acids, or about 30 to about 100 amino acids comprising amino acids 170-199 of SEQ ID NO: 1, amino acids 180-199 of SEQ ID NO: 1, or amino acids 186-199 of SEQ ID NO: 1, and their orthologous counterparts.

A third embodiment of the present invention includes a modified ICOS protein fragment comprising a protein fragment from the cytoplasmic domain of an ICOS protein. In one aspect, the ICOS protein is selected from any of SEQ ID NO: 1-17. In certain aspects, the ICOS protein fragment includes one or more of:
  a) at least one of SEQ ID NO: 18, SEQ ID NO: 27-40, SEQ ID NO: 19, SEQ ID NO: 41, or SEQ ID NO: 20; or
  b) peptide sequences selected from one or more of X1 SSX2X3X4PX5X6X7, where X1 may be absent or present, and if present may be S; X2, X3, X4, X5; and X6 may be any amino acid and X7 is preferably D or E (SEQ ID NO: 18), YX1X2M where X1 and X2 may be any amino acid, (SEQ ID NO: 19), or XVNTAKK, where X may be any amino acid (SEQ ID NO: 20).

A fourth embodiment includes nucleic acids encoding any of the peptides, proteins, or protein fragments of embodiments 1-3.

A fifth embodiment includes chimeric antigen receptor (CAR) comprising an antigen recognition domain (extracellular domain), a transmembrane domain, and a cytoplasmic domain comprising a protein or peptide according to any of the preceding embodiments.

A sixth embodiment includes a vector comprising a DNA sequence encoding a protein, peptide, or CAR according to any of the preceding embodiments.

A seventh embodiment includes a nucleic acid inhibitor of ICOS. In one aspect, the nucleic acid inhibitor blocks or interferes with the transcription or translation of a motif of ICOS. In a particular aspect the nucleic acid inhibitor of ICOS is selected from antisense, ribonucleic acid enzymes (ribozymes), small interfering RNA (siRNA), Dicer-substrate RNA (dsRNA), small hairpin RNA (shRNA), asymmetrical interfering RNA (aiRNA), and micro RNA (miRNA).

An eighth embodiment includes a cell expressing any of the peptides or proteins of any of the preceding embodiments, or comprising the vector according to the sixth embodiment or a nucleic acid inhibitor according to the seventh embodiment. In one aspect, the cell is an immune effector cell. In a particular aspect, the cell is a T cell.

A ninth embodiment includes a composition comprising: one or more peptides, proteins, or protein fragments according to any of the preceding embodiments, one or more nucleic acids according to embodiment 4, a CAR according to embodiment 5, one or more vectors according to embodiment 6, one or more nucleic acid inhibitors according to embodiment 7, and/or one or more cells according to embodiments 8. In one particular aspect, the composition is a pharmaceutical composition. A particular pharmaceutical composition includes a pharmaceutically acceptable carrier. In a particular aspect, the composition is for use in a method of treating autoimmune diseases, neurodegenerative diseases, metabolic diseases, cancer, inflammatory diseases, and immunodeficiencies.

A tenth embodiment includes an adjuvant comprising the composition according to the ninth embodiment.

An eleventh embodiment includes a method of modulating the interaction between ICOS and TBK1. In one aspect, the method includes contacting a cell with an agonist or antagonist of ICOS-mediated or TBK1-mediated immune signaling. In one aspect, the cell is a T-cell or a B-cell, and in particular may be a Tfh cell. In a particular aspect, the agonist or antagonist is selected from:
  a) one or more peptides, proteins, or protein fragments of embodiments 1-3,
  b) one or more nucleic acids according to embodiment 4,
  c) the CAR according to embodiment 5,
  d) one or more vectors according to embodiment 6,
  e) one or more nucleic acid inhibitors according to embodiments 7-9, and
  f) one or more cells according to embodiments 10-12.

A twelfth embodiment includes a method of modulating the interaction between TBKBP1, IKKβ and IRF4 and BATF by modulating the interaction between ICOS and TBK1.

A thirteenth embodiment includes a method of treating infectious diseases, autoimmune diseases, neurodegenerative diseases, metabolic diseases, cancer, inflammatory diseases, or immunodeficiencies comprising administering a composition according to the ninth embodiment to a subject in need thereof. In a particular aspect, the disease is treatment of infection with *Leishmania major*, improved allograft survival, improved T-cell-dependent antibody production, treatment of allergic lung disease, improves tumor immunity, regulation of autoimmune diabetes, improved T-cell tolerance, ALS, cancer, or obesity. In a particular aspect, the composition is an antagonist of ICOS/TBK1-mediated immune signaling and the disease is an autoimmune, metabolic, or inflammatory disease. In yet a further aspect, the composition is an agonist of ICOS/TBK1-mediated immune signaling and the composition is a vaccine. In another aspect, the composition is an agonist of ICOS/TBK1-mediated immune signaling and the disease is cancer or an immune-deficiency disorder.

A fourteenth embodiment includes a method of modulating Tfh cell development by modulating the interaction between ICOS and TBK1. In a particular aspect, the method comprises treating infectious diseases, autoimmune diseases, neurodegenerative diseases, metabolic diseases, cancer, inflammatory diseases, or immunodeficiencies. In yet another aspect the method comprises agonizing the interaction between ICOS and TBK1 to increase, enhance, promote or elicit Tfh cell development or activity. In yet a further aspect, the method comprises treatment of cancer, neurodegenerative disease or an immunodeficiency disorder. In another aspect, the method comprises increasing, enhancing, promoting or eliciting immune response to a vaccine. In a particular aspect, the method comprises agonizing the interaction between ICOS and TBK1 to inhibit, block or decrease Tfh cell development or activity. In another aspect, the method comprises treatment of autoimmune diseases, metabolic disease, obesity or inflammatory disease.

DETAILED DESCRIPTION

Figure 1:
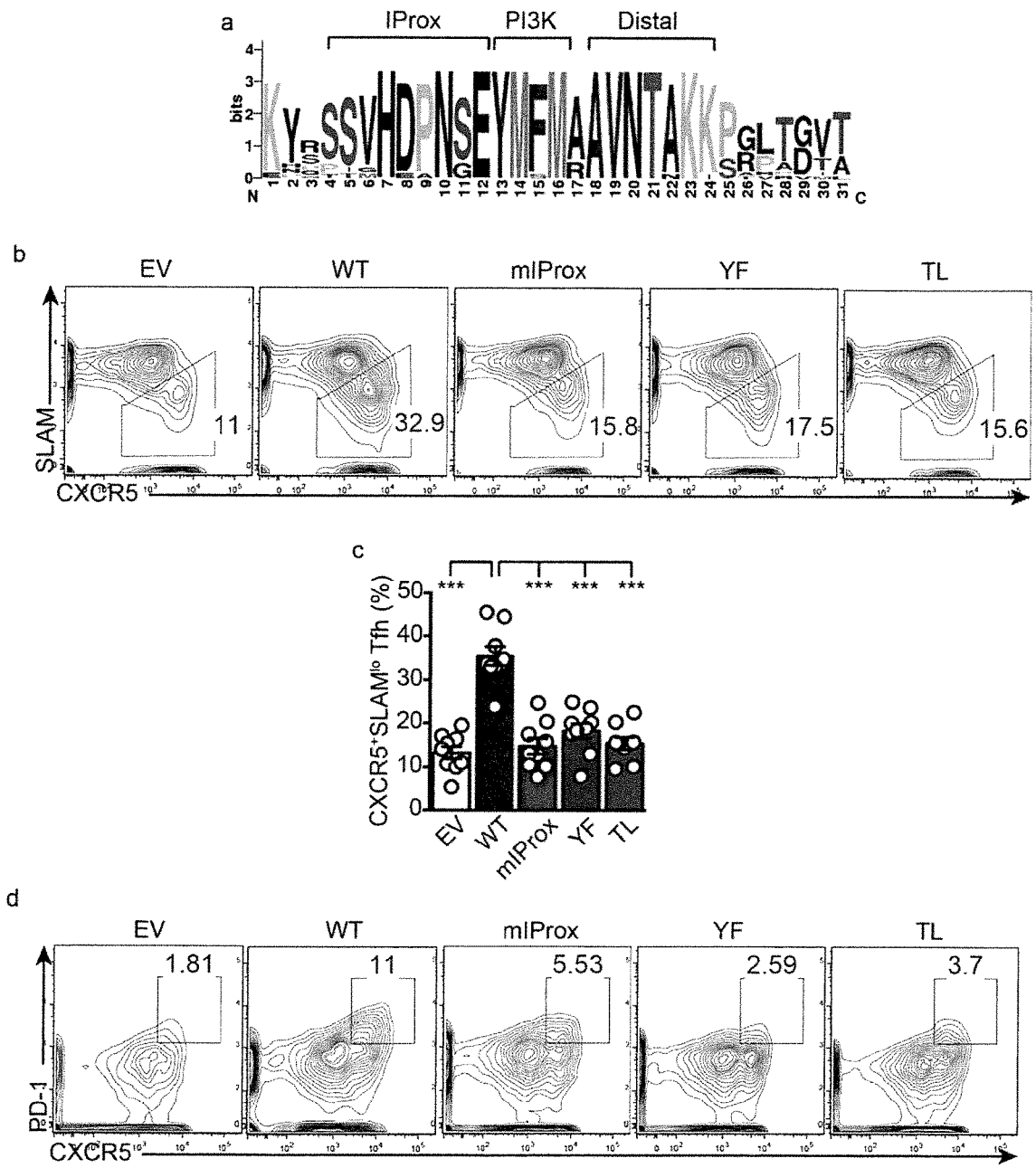
FIG. 1. Importance of a novel ICOS signaling motif in Tfh cell development. (a) Evolutionary conservation of the ICOS cytoplasmic tail. (b-e) Icos$^{-/-}$ SMARTA CD4$^+$ T cells transduced with RV encoding WT ICOS, ICOS with alanine-substituted IProx motif (mIProx), mutation of the PI3K-binding site (Y181F; YF), or tailless (deletion of amino acid residues 170200; TL) were adoptively transferred into B6 mice, which were infected with LCMV Armstrong strain. CXCR5$^+$SLAM$^{lo}$ Tfh cells (b, c), and CXCR5$^+$PD1$^{hi}$ GC Tfh cells (d, e) were analyzed 7 d later by FACS (b, d), with cumulative data from three independent experiments shown in (c, e). Each data point represents a single mouse. Shown are mean±SEM; ANOVA with post-hoc Tukey's corrections. (f-l) Icos$^{-/-}$ SMARTA CD4$^+$ T cells transduced as in (b) were adoptively transferred into CD4-CrexBcl6$^{fl/fl}$ recipients, which were immunized with KLH-gp61 absorbed to alum. CD95$^+$GL7$^+$ GC B cells (f, g), and CD138$^+$IgD$^-$ plasma cells (h, i), were analyzed 10 d later by FACS (f, h), with cumulative data from two independent experiments shown in (g, i). Anti-KLH-gp61 IgG from sera of immunized mice were analyzed with ELISA and presented as absorbance at 450 nm (j), and the endpoint titer (k) and area under curve (l) were calculated. Each data point represents a single mouse. Shown are mean±SEM; unpaired two-tailed Student's t-test. *P<0.01; P<0.001; *P<0.0001.
Figure 1:
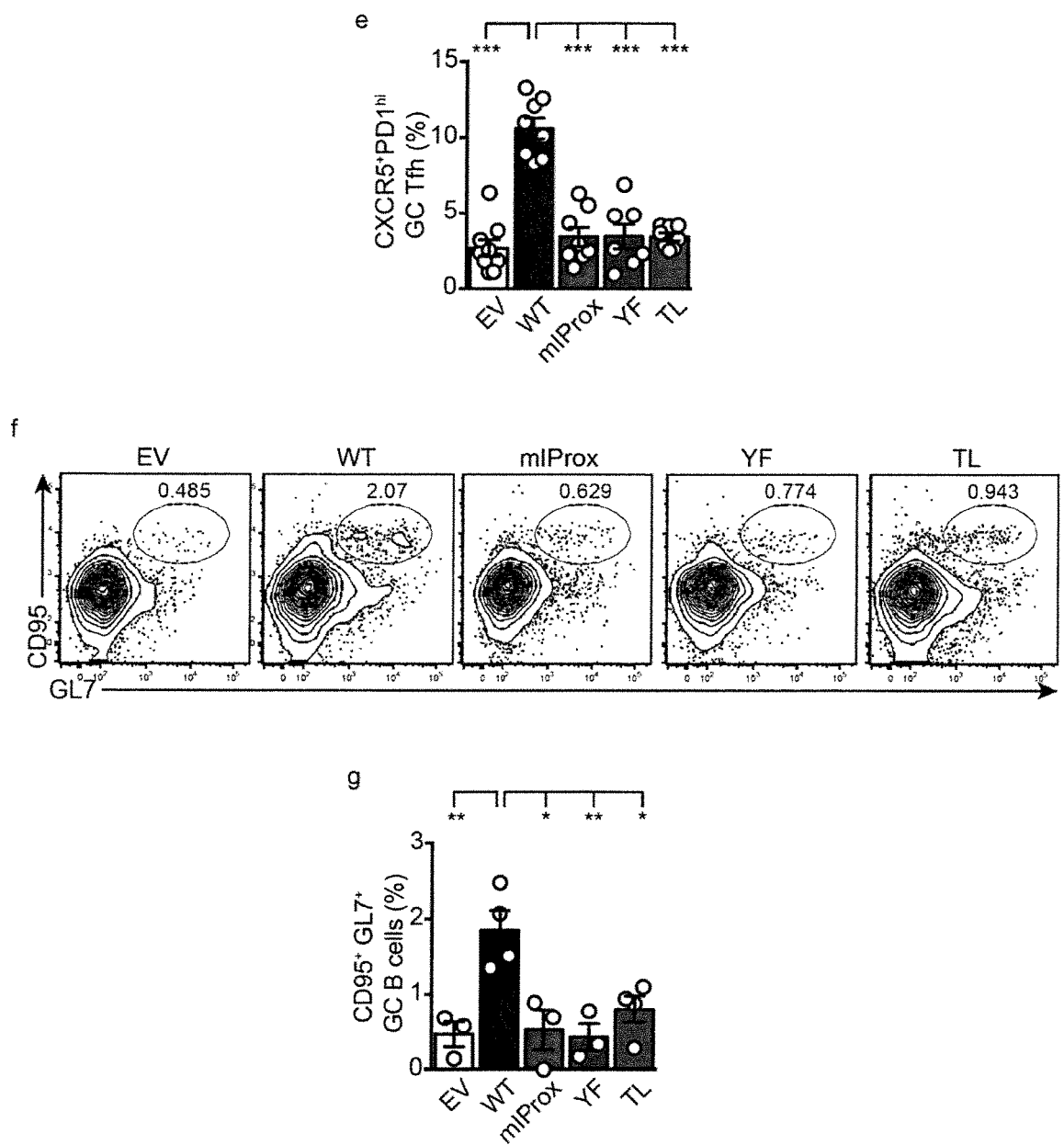
Figure 1:
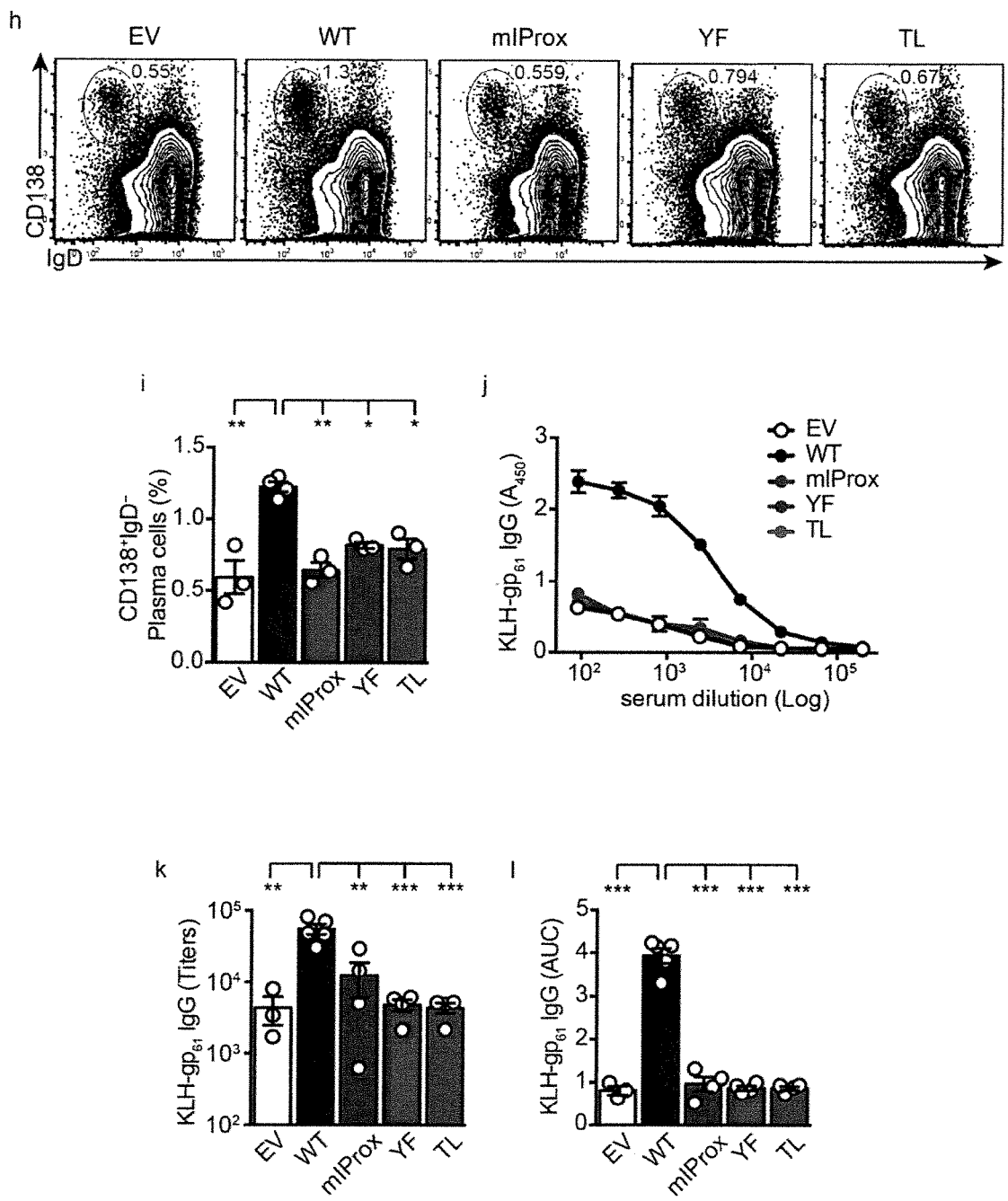

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

In case of conflict, the present specification, including definitions, will control. In addition, the materials, methods, and examples are illustrative only and not intended to be limiting.

I. Definitions

In one embodiment, the present compounds may have an agonist activity. An agonist, as used herein, is a mimetic of the natural ligand and produces a similar biological effect as the natural ligand when it binds to the receptor or binding partner. It binds at the same binding site, and leads, in the absence of the natural ligand, to either a full or partial response. In the latter case, it is called a partial agonist.

In another embodiment, the present compounds may have an inverse agonist activity. As used herein, the term "inverse agonist" is a ligand which when bound to its receptor or binding partner, decreases or inhibits the receptor's or binding partner's basal activity. If either the natural ligand or an agonist binds to the receptor site or binding partner's binding site, the basal activity is increased. If however, an inverse agonist binds, the activity is decreased.

In yet another embodiment, the present compounds have an antagonist activity. Antagonist is defined broadly and is used to mean a ligand which decreases the effects of an agonist. These may be immediate effects or downstream effects. An antagonist may be a competitive antagonist, which interferes with the binding of the agonist with its receptor, or a non-competitive agonist, which binds at a different location than the agonist.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "antisense" is intended to refer to polynucleotide molecules complementary to a portion of an RNA expression product of UC41, as defined herein. "Complementary" polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Antisense polynucleotides, when introduced into a target cell, specifically bind to their target polynucleotide (such as the sequence encoding ICOS or the ICOS motifs) and interfere with transcription, RNA processing, transport, translation and/or stability. Antisense RNA constructs, or DNA encoding such antisense RNAs, may be employed to inhibit gene transcription or translation or both within a host cell, either in vitro or in vivo, such as within a host animal, including a human subject.

As an alternative to targeted antisense delivery, targeted ribozymes may be used. The term "ribozyme" is refers to an RNA-based enzyme capable of targeting and cleaving particular base sequences in both DNA and RNA. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is an immune-modulatory disease, and is defined as a disorder that results from an autoimmune response. An autoimmune disease is the result of an inappropriate and excessive response to a self-antigen. Examples of autoimmune diseases include but are not limited to, Addision's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barre syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Identity" or "percent identity," in the context of two or more polypeptide sequences, refers to two or more sequences or subsequences that are the same or have a specified percentage of amino acid residues that are the same (e.g., share at least about 70%, at least about 75%, at least about 80%, at least about 85%, at least about 88% identity, at least about 89%, at least about 90%, at least about 91%, at least about 92%, at least about 93%, at least about 94%, at least about 95%, at least about 96%, at least about 97%, at least about 98%, or at least about 99% identity) over a specified region to a reference sequence, when compared and aligned for maximum correspondence over a comparison window, or designated region as measured using a sequence comparison algorithms or by manual alignment and visual inspection.

Optimal alignment of sequences for comparison and determination of sequence identity can be determined by a sequence comparison algorithm or by visual inspection. When optimally aligning sequences and determining sequence identity by visual inspection, percent sequence identity is calculated as the number of residues of the test sequence that are identical to the reference sequence divided by the number of non-gap positions and multiplied by 100. When using a sequence comparison algorithm, test and reference sequences are entered into a computer, subsequence coordinates and sequence algorithm program parameters are designated. The sequence comparison algorithm then calculates the percent sequence identities for the test sequences relative to the reference sequence, based on the program parameters.

An algorithm that may be used to determine whether a modified ICOS or LCOS fragment has sequence identity to a reference sequence, such as SEQ ID NO: 1 (unmodified ICOS) or a specific portion thereof is the BLAST algorithm, which is described in Altschul et al., 1990, J. Mol. Biol. 215:403-410, which is incorporated herein by reference. Software for performing BLAST analyses is publicly available through the National Center for Biotechnology Information (on the worldwide web at ncbi.nlm.nih.gov/). Other programs that may be used include the Needleman-Wunsch procedure, J. Mol. Biol. 48: 443-453 (1970), using blosum62, a Gap start penalty of 7 and gap extend penalty of 1; and gapped BLAST 2.0 (see Altschul, et al. 1997, Nucleic Acids Res., 25:3389-3402) both available to the public at the National Center for Biotechnology Information Web site.

Multiple sequences can be aligned with each other by visual inspection or using a sequence comparison algorithm, such as PSI-BLAST (Altschul, et al., 1997, supra) or "T-Coffee" (Notredame et al., 2000, J. Mol. Bio. 302:205-17). T-Coffee alignments may be carried out using default parameters (T-Coffee Technical Documentation, Version 8.01, July 2009, WorldWideWeb .tcoffee.org), or Protein Align. In Protein Align, alignments are computed by optimizing a function based on residue similarity scores (obtained from applying an amino acid substitution matrix to pairs of aligned residues) and gap penalties. Penalties are imposed for introducing and extending gaps in one sequence with respect to another. The final optimized function value is referred to as the alignment score. When aligning multiple sequences, Protein Align optimizes the "sum of pairs" score, i.e., the sum of all the separate pairwise alignment scores.

The phrase "substantial sequence identity" or "substantial identity," in the context of two nucleic acid or polypeptide sequences, refers to a sequence that has at least 70% identity to a reference sequence. Percent identity can be any integer from 70% to 100%. Two nucleic acid or polypeptide sequences that have 100% sequence identity are said to be "identical." A nucleic acid or polypeptide sequence are said to have "substantial sequence identity" to a reference sequence when the sequences have at least about 70%, at least about 75%, at least 80%, at least 85%, at least 90%, at least 91%, at least 92%, at least 93%, at least 94%, at least 95%, at least 96%, at least 97%, at least 98%, or at least 99% or greater sequence identity as determined using the methods described herein, such as BLAST using standard parameters as described above.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts.

The term "interfering RNA" or "RNAi" or "interfering RNA sequence" as used herein includes single-stranded RNA (e.g., mature miRNA, ssRNAi oligonucleotides, ssDNAi oligonucleotides), double-stranded RNA (i.e., duplex RNA such as siRNA, Dicer-substrate dsRNA, shRNA, aiRNA, or pre-miRNA), a DNA-RNA hybrid (see, e.g., PCT Publication No. WO 2004/078941), or a DNA-DNA hybrid (see, e.g., PCT Publication No. WO 2004/104199) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Preferably, the interfering RNA molecules are chemically synthesized. The disclosures of each of the above patent documents are herein incorporated by reference in their entirety for all purposes.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule. As used herein, the term "siRNA" includes RNA-RNA duplexes as well as DNA-RNA hybrids (see, e.g., PCT Publication No. WO 2004/078941).

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

A nucleic acid (such as a polynucleotide), a polypeptide, or a cell is "recombinant" when it is artificial or engineered, or derived from or contains an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant. DNA may be in the form of, e.g., antisense molecules, plasmid DNA, DNA- DNA duplexes, pre-condensed DNA, PCR products, vectors (P1, PAC, BAC, YAC, artificial chromosomes), expression cassettes, chimeric sequences, chromosomal DNA, or derivatives and combinations of these groups. RNA may be in the form of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "modified" when used to refer to a nucleic acid or protein sequence is used to denote that the sequence does not naturally occur. The sequence may be a truncated version of a larger sequence (e.g., a peptide fragment of a whole protein), may be a chimeric molecule (either by adding an additional sequence of the same type from a different source, or by adding a different biological molecule, such as a protein/DNA chimera etc.), or the sequence may have one or more deleted, added or substituted nucleic acids or amino acids. A genetically modified cell for instance may be modified by incorporating a mutation or other sequence into the genome, or may be modified by the addition of an expression vector etc.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell. An "inducible" promoter is a nucleotide sequence which, when operably linked with a polynucleotide which encodes or specifies a gene product, causes the gene product to be produced in a cell substantially only when an inducer which corresponds to the promoter is present in the cell. A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody or other protein, is meant an antibody which recognizes a specific antigen or a protein which preferentially binds a particular ligand or structure, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally.

The term "subject," "patient" and "individual" are used interchangeably herein and are intended to include living organisms in which an immune response can be elicited (e.g., mammals). Examples of subjects include humans, dogs, cats, mice, rats, and transgenic species thereof.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like. A vector may be an expression vector that is operably linked to a suitable control sequence capable of effecting the expression in a suitable host of the polypeptide encoded in the DNA sequence.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

II. Compositions and Methods

The present disclosure relates to methods and compositions useful for initiating and propagating ICOS-mediated signaling. In particular, the present disclosure provides three peptide motifs which promote ICOS binding and whose ablation leads to modulated ICOS signaling or signaling mediated by TBK1, IRF4, IKKβ, or TBKBP1. The binding these peptide motifs or the addition of such motifs as co-stimulatory agents leads to modulated immune responses, and provides new and unexpected therapies for neurodegenerative, cancer, autoimmune, metabolic, inflammatory, or immunodeficiency conditions, diseases, or disorders.

Proteins of Interest

In one embodiment, the present compositions modulate ICOS signaling through one of three motifs found in the short cytoplasmic tail of ICOS. In one particular embodiment, the present compositions modulate ICOS signaling through TBKI to modulate an immune response. In particular, ICOS binds TBK1 at the proximal motif (variously named "proximal motif" and "IProx") when stimulated by binding at the ICOSL and with CD3. Thus stimulating the TBKI mediated activation of NF-kB to promote transcription an generate a physiological response such as an inflammatory or immune response, a cell survival response, or cellular proliferation. Accordingly, these proteins of interest are more fully described below.

ICOS

As described herein, ICOS may be any ICOS protein including orthologs. In particular, the ICOS protein may be derived from human, *Pan troglodytes*, orangutan, *Macaca mulatta*, domesticated dog, domesticated cat, cow, panda, mouse, rat, rabbit, platypus, turkey, *gallus*, mallard, zebra finch, or *Xenopus topicalis*. In particular, the human ICOS sequence referred to herein is:

```
>gi|15029518|ref|NP_036224.1| inducible T-cell
costimulator precursor [Homo sapiens]
                                        (SEQ ID NO: 1)
MKSGLWYFFLFCLRIKVLIGEINGSANYEMFIFHNGGVQILCKYPDI

VQQFKMQLLKGGQILCDLIKTKGSGNIVSIKSLKFCHSQLSNNSVSF

FLYNLDHSHANYYFCNLSIFDPPPFKVILIGGYLHIYESQLCCQLKF

WLPIGCAAFVVVCILGCILICWLIKKKYSSSVHDPNGEYMFMRAVNT

AKKSRLTDVIL.
```

Reference to ICOS amino acid positions described herein are based on the human sequence SEQ ID NO: 1, however, a skilled artisan would understand that reference may be applied to homologous structures or motifs found in protein isoforms, mutant sequences, or orthologous ICOS sequences by sequence alignment techniques. Orthologous ICOS sequences may be found in the sequence listing at SEQ ID NOs: 2-17.

TBK11

TANK-binding kinase 1 (TBK1) is an enzyme encoded by the TBK1 gene. The NF-kappa-B (NFKB) complex of proteins is inhibited by I-kappa-B (1 KB) proteins, which inactivate NFKB by trapping it in the cytoplasm. Phosphorylation of serine residues on the IKB proteins by IKB kinases marks them for destruction via the ubiquitination pathway, thereby allowing activation and nuclear translocation of the NFKB complex. The TBK1 protein is similar to IKB kinases and can mediate NFKB activation in response to certain growth factors. For example, the TBK1 protein can form a complex with the IKB protein TANK and TRAF2 and release the NFKB inhibition caused by TANK. Inhibition of TBKI may treat inflammatory diseases, immunodeficiency disorders, and cancer.

As described herein, TBK1 may be any TBK1 protein including orthologs. The TBK1 protein may be derived from any mammal, in particular a human, mouse, or rat.

TBKBP1

TBK Binding Protein 1 (also known as SINTBAD) is an adaptor protein which constitutively binds TBK1 and IKKi to activate interferon regulatory factors (IRFs), which in turn drive transcription of antiviral genes during infection. Thus, inhibition or increases of signaling through TBKBP1 by prevention of binding of TBKBP1 to either TBK1 or IKKi may be useful in the treatment of infection.

IRFs

Interferon Regulatory Factors proteins which regulate transcription of interferons. As shown here, TBK1 signaling affects the IRF-4/BATF complex. TBK1 interacts with IRF-4/BATF after ICOS signaling. Thus, modulation of the interaction between ICOS and TBK1 modulates the IRF-4/BATF complex. Such modulation may alter the Tfh cell commitment to.

BATF

Basic leucine zipper transcriptional factor ATF-like (BATF) is a basic leucine zipper (bZIP) transcription factor and is part of the AP-1/ATF family that forms inhibitory dimers with members of the Jun family. Expression of BATF is largely restricted with highest levels found in mature T cells, and it is induced in B cells following immune responses including viral infection. BATF expression is also induced by IL-6 via a Stat3-dependent mechanism. BATF plays an important role in the differentiation of immune cell lineages. Studies of BATF-deficient mice have demonstrated a critical role for BATF in the formation of IL-17-expressing Th17 cells, in part, by regulating the expression of IL-17. BATF knockouts are resistant to experimental autoimmune encephalomyelitis (EEA), consistent with the role of Th17 cells in this model for autoimmunity (see Schram) et al., *Nature*, 2009 Jul. 16; 460(7253):405-9, the entire contents of which are hereby incorporated by reference). Additional studies have found that BATF is important in generating antibody class switching. BATF is required for the generation of follicular helper T cells (Tfh), by regulating BCL6 and c-Maf (see Betz et al., *J Exp Med*. 2010 May 10; 207(5):933-42; Ise et al., *Nat Immunol*. 2011 June; 12(6): 536-43, the entire contents of each are hereby expressly incorporated by reference). In B cells, BATF controls the expression of activation-induced cytidine deaminase (AID) and regulates class-switched antibody responses. As shown herein, BATF-mediated transcription may be modulated by signaling through the ICOS-TBK1 pathway by modification of binding with or ablation of the proximal motif, the YXXM motif, or the distal motif of ICOS.

TRAF-2

TNF receptor-associated factor 2 is a member of the TNF receptor associated factor (TRAF) protein family. TRAF proteins associate with, and mediate the signal transduction from members of the TNF receptor superfamily. This protein directly interacts with TNF receptors, and forms complexes with other TRAF proteins. TRAF-2 notably forms complexes with TBK1, described above.

The present examples demonstrate that ICOS associates with TANK-binding kinase 1 (TBK1), TBK1 binding protein 1 (TBKBP1, also known as SINTBAD) and inhibitor of nuclear factor kappa-B kinase subunit beta (IKK.3 or IKK.2) via a conserved motif, in particular the proximal motif. Disruption of this motif in particular in ICOS abolished their association with TBK1. Mutation of this motif in ICOS, or depletion of TBK1 in T cells severely impaired the differentiation of germinal center (GC) Tfh and B cell responses, but was dispensable for early Tfh cell differentiation. Further the present examples demonstrate that TBK1 associates with 1RF4 and Batf following ICOS stimulation, indicating that 1RF4 and Batf act as the transcription factors downstream of the ICOS-TBK1 pathway. These results reveal a novel ICOS-TBKBP1-TBK1-1KK?-1RF4-Batf signaling pathway that specifies the Tfh cell commitment to GC reactions.

Protein Therapies

Modified ICOS

In one embodiment, the present invention includes a modified ICOS protein. In one aspect, the ICOS protein sequence is modified by adding, deleting or substituting amino acids. In a particular aspect, the ICOS protein is modified by adding, deleting, or substituting one or more amino acid residues in SEQ ID NO: 1 at amino acid positions 170-179, 180-184, or 186-193 (WT human ICOS) or similar modification in orthologous counterparts.

In yet a further embodiment, the present invention includes modified ICOS proteins comprising the substitute motif sequences, where SEQ ID NO: 1 is substituted with one or more motifs such as at amino acid position 170-179 substituted with X1SSX2X3X4PX5X6X7, where X1 may be absent or present, and if present may be S; X2, X3, X4, X5, and X6 may be any amino acid and X7 is D or E (SEQ ID NO: 18), substituted at positions 180-183 with YX1X2M where X1 and X2 may be any amino acid, but XI preferably is M, X2 may be any amino acid but preferably is F or P (SEQ ID NO: 19), or substituted at amino acid positions 186-193, where XVNTAKK, where X may be any amino acid, but preferably is A or S (SEQ ID NO: 20). In yet a further embodiment, a modified ICOS protein has the sequence of SEQ ID NO: 21, where amino acid position 170-179 substituted with AAAAAAAAAA (SEQ ID NO: 22), Truncated ICOS Protein In yet another embodiment, the present invention includes modified ICOS protein, wherein the protein includes amino acids 1-169 of SEQ ID NO: 1, amino acids 1-179 of SEQ ID NO:1, or amino acids 1-185 of SEQ ID NO: 1. In one aspect, the modified ICOS protein consists of 1-169 of SEQ ID NO: 1, amino acids 1-179 of SEQ ID NO: 1, or amino acids 1-185 of SEQ ID NO: 1, or their orthologous counterparts. In one embodiment, the modified ICOS protein comprises amino acids 1-169 of SEQ ID NO: 1, joined to a linker LESGGGG (SEQ ID NO: 23) at either the N or C terminal.

In another embodiment, a modified ICOS protein may also include peptides having from about 19 to about 100 amino acid residues, about 20 to about 100 amino acids, or about 30 to about 100 amino acids comprising amino acids 170-199 of SEQ ID NO: 1, amino acids 180-199 of SEQ ID NO: 1, or amino acids 186-199 of SEQ ID NO: 1, and their orthologous counterparts. In one embodiment, the modified ICOS protein consists of amino acids 170-199 of SEQ ID NO: 1, amino acids 180-199 of SEQ ID NO: 1, or amino acids 186-199 of SEQ ID NO: 1, or their orthologous counterparts.

Motifs

In yet a further embodiment, the present invention includes modified ICOS protein fragments. In one aspect such fragments include peptides comprising SEQ ID NO: 24 (Proximal Motif hICOS aa 170-179), SEQ ID NO: 25

(YXXM Motif hICOS aa 180-183), or SEQ ID NO: 26 (Distal Motif hICOS aa 186-193), and their orthologous counterparts (see e.g., proximal motif sequences SEQ ID NO: 27-40), YXXM motif sequences SEQ ID NO: 41, and distal motif sequences.

In yet a further embodiment, the present invention includes modified ICOS proteins comprising protein fragments comprising peptide sequences selected from one or more of X1SSX2X3X4PX5X6X7, where X1 may be absent or present, and if present may be S; X2, X3, X4, X5, and X6, may be any amino acid and X7 is D or E (SEQ ID NO: 18); YX1X2M where X1 and X2 may be any amino acid, but X1 preferably is M, X2 may be any amino acid but preferably is F or P (SEQ ID NO: 19), or XVNTAKK, where X may be any amino acid but is preferably A or S (SEQ ID NO: 20).

In one embodiment, a protein fragment comprising X1SSX2X3X4PX5X6X7, where X1 may be absent or present, and if present may be S; X2, X3, X4, X5; and X6 may be any amino acid and X7 is D or E (SEQ ID NO: 18), which may act as an antagonist to ICOS-TBK1 signaling. In one aspect, the protein fragment is a competitive antagonist.

CARs

In one embodiment, the present invention includes a Chimeric antigen receptor (CAR). A CAR is an artificial T cell receptor, where T cells are removed from a patient and modified so that they express receptors specific to the particular form of cancer. The T cells, which can then recognize and kill the cancer cells, are reintroduced into the same patient or another patient. A CAR as described herein includes comprises an extracellular domain having an antigen recognition domain, a transmembrane domain, and a cytoplasmic domain.

A "Second-generation" CAR adds intracellular signaling domains from various costimulatory protein receptors (e.g., ICOS and optionally one or more of CD28, 41BB) to the cytoplasmic tail of the CAR to provide additional signals to the T cell. The structure of CARS is described in U.S. 2015-0017141, the entire contents of which are hereby incorporated by reference. Thus, in one embodiment, a modified ICOS protein or protein fragment is operably linked to the cytoplasmic domain.

In one embodiment, the present invention relates generally to the use of T cells genetically modified to express a desired CAR (chimeric antigen receptor). T cells expressing a CAR are referred to herein as CAR T cells or CAR modified T cells. Preferably, the cell can be genetically modified to express an antibody binding domain on its surface, conferring novel antigen specificity that is MHC independent. In some instances, the T cell is genetically modified to express a CAR that combines an antigen recognition domain of a specific antibody with an intracellular domain of the CD3-zeta chain or FcyR1 protein into a single chimeric protein.

In one embodiment, the CAR of the invention comprises an extracellular domain having an antigen recognition domain, a transmembrane domain, and a cytoplasmic domain. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. In some embodiments, the extracellular domain also comprises a hinge domain. Preferably, the hinge domain comprises the CD8a hinge domain. In one embodiment, the CAR includes a "spacer domain" between the extracellular domain and the transmembrane domain of the CAR or between the cytoplasmic domain and the transmembrane domain of the CAR. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

With respect to the cytoplasmic domain, the CAR of the invention can be designed to comprise the ICOS signaling domain by itself or be combined with any other desired cytoplasmic domain(s) useful in the context of the CAR of the invention. In one embodiment, the cytoplasmic domain of the CAR can be designed to further comprise the signaling domains of CD3-zeta, 4-1 BB, and/or CD28. For example, the cytoplasmic domain of the CAR can include but is not limited to the present ICOS motifs, CD3-zeta, 4-1 BB and CD28 signaling modules and combinations thereof. Accordingly, the invention provides CAR T cells and methods of their use for adoptive therapy.

Side effects of using second generation CAR-modified T cells include a clinically significant release of pro-inflammatory cytokines, pulmonary toxicity, multi-organ failure, and potential death. See Morgan et al. Molecular Therapy (2010) 18(4); 843-851, the entire contents herein expressly incorporated by reference. The cytokine response was thought to be due to CAR T cell toxicity against normal lung epithelial cells. Consequently, there is a need for an anti-inflammatory mitigator of CAR-stimulated inflammatory responses.

In one embodiment, the CAR comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

In one embodiment, the CAR of the invention can be engineered to target a tumor antigen of interest by way of engineering a desired antigen binding domain that specifically binds to an antigen on a tumor cell. In the context of the present invention, "tumor antigen" or "hyperproliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

Tumor antigens are proteins that are produced by tumor cells that elicit an immune response, particularly T-cell mediated immune responses. The selection of the antigen binding domain of the invention will depend on the particular type of cancer to be treated. Tumor antigens are well known in the art and include, for example, a glioma-associated antigen, carcinoembryonic antigen (CEA), (β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1 a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD 19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein \cyclophilin C-associated protein, TAAL6, TAG72, TLP, and TPS.

In a particular embodiment, the antigen binding domain portion of the CAR targets an antigen that includes but is not limited to CD19, CD20, CD22, ROR1, Mesothelin, CD33/IL3Ra, c-Met, PSMA, Glycolipid F77, EGFRvIII, GD-2, MY-ESO-1 TCR, MAGE A3 TCR, and the like.

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, ICOS. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability. In one embodiment, the intracellular signaling domain includes a peptide sequence comprising one or more of the ICOS motifs, such as a peptide comprising one or more of $X_1SSX_2X_3X_4PX_5X_6X_7$, where $X_1$ may be absent or present, and if present may be S; $X_2$, $X_3$, $X_4$, $X_5$; and $X_6$ may be any amino acid and $X_7$ is D or E (SEQ ID NO: 18), $YX_1X_2M$ where $X_1$ and $X_2$ may be any amino acid, but $X_1$ preferably is M, $X_2$ may be any amino acid but preferably is F or P (SEQ ID NO: 19), or XVNTAKK, where X may be A or S (SEQ ID NO: 20). In another embodiment, the intracellular signaling domain includes a modified ICOS protein as discussed above.

Vectors Encoding Proteins

One embodiment includes a vector encoding the modified ICOS proteins or modified ICOS protein fragments.

One embodiment includes a vector encoding a CAR linked to a modified ICOS protein or modified ICOS protein fragment. In one aspect, the vector encoding a CAR optionally also includes sequences encoding the T-cell co-stimulatory domains for CD28 and/or CD137 (4-1 BB)(extra domains shown to enhance in vivo anti-tumor activity of CARs) (see e.g., Morgan et al., supra).

In one aspect, the vector includes a transcription element or promoter.

Cells

One embodiment described herein provides for the expression of modified ICOS proteins or protein fragments in cells. Such expression may be the result of transfection or stable transformation with an expression vector containing a DNA sequence encoding the modified ICOS protein, or fragment thereof. In one aspect, the modified ICOS may be operably linked to a CAR as a co-stimulatory agent.

In one embodiment, the present modified ICOS proteins or fragments are expressed in T cells. In another embodiment, the modified ICOS proteins or fragments are expressed in host cells.

In one embodiment, the cells are T cells. In one aspect of this embodiment, the T cells are Tfh cells. In one aspect, the T cells are isolated from PBMCs.

Nucleic Acid Inhibitors of ICOS

In one embodiment, the present invention includes nucleic acid inhibitors of ICOS. Nucleic acid inhibitors of ICOS include DNA and RNA inhibitors. Such inhibitors decrease the transcription or translation of ICOS by blocking or interfering with transcription or translation of one or more of the ICOS motif regions. In one particular aspect, such inhibitors block or interfere with the transcription or translation of the proximal motif of ICOS. Such inhibitors include antisense, ribonucleic acid enzymes (ribozymes), small interfering RNA (siRNA), Dicer-substrate RNA (dsRNA), small hairpin RNA (shRNA), asymmetrical interfering RNA (aiRNA), and micro RNA (miRNA).

Methods of Treatment

In one aspect, the present compositions have an inhibitory, antagonistic, or disruptive activity. As used herein the terms inhibit, decrease, reduce, suppress, or disrupt are all used to indicate that the ICOS-mediated, TBK1-mediated, TBKBP1-mediated signaling, IKK?-mediated signaling, IRF4-mediated, or BATF-mediated signaling is decreased or stopped. In this embodiment, the compositions described herein act by inhibiting or otherwise decreasing the activation and/or cell signaling pathways of the cell expressing one or more of ICOS, TBK1, TBKBP1, IKKβ, IRF-4, and BATF.

In another aspect, the present compositions increase cell signaling or have an agonistic activity. In this embodiment, the compositions described herein act by increasing or otherwise agonizing the activation and/or cell signaling pathways of the cell expressing one or more of ICOS, TBK1, TBKBP1, IKKβ, IRF-4, and BATF.

Immune Response

The invention thus provides compositions for modifying or altering (i.e., increasing or decreasing in a statistically significant manner, for example, relative to an appropriate control as will be familiar to persons skilled in the art) immune responses or immune signaling in a host capable of mounting an immune response or conveying immunological signals. As will be known to persons having ordinary skill in the art, an immune response may be any active alteration of the immune status of a host, which may include any alteration in the structure or function of one or more tissues, organs, cells or molecules that participate in maintenance and/or regulation of host immune status. Typically, immune responses may be detected by any of a variety of well-known parameters, including but not limited to in vivo or in vitro determination of: soluble immunoglobulins or antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death); or any other criterion by which the presence of an immune response may be detected.

Immune responses may often be regarded, for instance, as discrimination between self and non-self structures by the cells and tissues of a host's immune system at the molecular and cellular levels, but the invention should not be so limited. For example, immune responses may also include immune system state changes that result from immune recognition of self molecules, cells or tissues, as may accompany any number of normal conditions such as typical regulation of immune system components, or as may be present in pathological conditions such as the inappropriate autoimmune responses observed in autoimmune and degenerative diseases. As another example, in addition to induction by up-regulation of particular immune system activities (such as antibody and/or cytokine production, or activation of cell mediated immunity) immune responses may also include suppression, attenuation or any other down-regulation of detectable immunity, which may be the consequence of the antigen selected, the route of antigen administration, specific tolerance induction or other factors. Thus, in one particular embodiment, the present compositions inhibit, decrease, antagonize, reduce, suppress, or prevent an immune response caused by a self antigen.

Determination of the induction or suppression of an immune response by the compositions described herein may be established by any of a number of well-known immunological assays with which those having ordinary skill in the art will be readily familiar. Such assays frequently determine immune signaling by detecting in vivo or in vitro determination of: soluble antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death). Procedures for performing these and similar assays are widely known and may be found, for example in Lefkovits (Immunology Methods Manual: The Comprehensive Sourcebook of Techniques, 1998; see also Current Protocols in Immunology; see also, e.g., Weir, Handbook of Experimental Immunology, 1986 Blackwell Scientific, Boston, Mass.; Mishell and Shigii (eds.) Selected Methods in Cellular Immunology, 1979 Freeman Publishing, San Francisco, Calif.; Green and Reed, 1998 Science 281:1309 and references cited therein).

A signal is "mediated" by a protein or other cell function when modification of the protein or function modifies the immune signal. For instance, ICOS-mediated signaling may be modified by interfering or increasing with ICOS binding to one of a variety of ligands or co-stimulators, an interference with or increase in ICOS stimulation of TBK1, interference or increase of the T cell cytokine production or secretion stimulated by ICOS/TBK1 binding, or an increase or decrease of transcription stimulated by ICOS/TBK1 interaction.

Any number of other immunological parameters may be monitored using routine assays that are well known in the art.

In certain embodiments the immune response may comprise at least one of production or inhibition of the production of one or a plurality of cytokines wherein the cytokine is selected from interferon-gamma (IFN-α), tumor necrosis factor-alpha (TNF-γ), production of one or a plurality of interleukins wherein the interleukin is selected from IL-1, IL-2, IL-3, IL-4, IL-6, IL-8, IL-10, IL-12, IL-13, IL-16, IL-18 and IL-23, production or inhibition of the production of one or a plurality of chemokines wherein the chemokine is selected from MIP-1 a, MIP-113, RANTES, CCL4 and CCL5, and a lymphocyte response that is selected from a memory T cell response, a memory B cell response, an effector T cell response, a cytotoxic T cell response and an effector B cell response. In one particular embodiment, the immune response includes the increase or decrease of transcription by Nf-κB or IRF-4

By decrease, decreasing, reduce, or reducing of an immune response is intended to mean a detectable decrease of an immune response that is the result of the administration of a given antagonist. For instance, the amount of decrease of an immune response by a composition described herein may be determined relative to the level of an immune response without administration of the composition, or as determined relative to administration level of an immune response after administration of an ICOS signaling agonist. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the absence of the administration of the antagonist. A detectable decrease can be about 5%, 10%, 15%, 20%, 25%, 30%, 35%, 40%, 45%, 50%, 55%, 60%, 65%, 70%, 75%, 80%, 85%, 90%, 95%, or at least about 100% lower than the immune response detected after administration of an ICOS signaling agonist. A decrease in the immune response to the antagonist is typically measured by a decrease in cytokine production (e.g., IFNy, IFNa, TNFa, IL-6, IL-8, or IL-12) by the binding cell or a responder (bystander) cell in vitro, a decrease in cytokine production in the sera, or a decrease in transcription after administration of the antagonist.

The term excipient as used herein refers to one or more inert substances which are commonly used as a diluent, vehicle, preservative, binder, or stabilizing agent for drugs and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, Remington's Pharmaceutical Sciences (1990) Mack Publishing Co., Easton, Pa., which is hereby incorporated by reference in its entirety.

A further aspect of the composition provides a pharmaceutical formulation comprising the present compositions in admixture with a pharmaceutically or veterinarily acceptable adjuvant, diluent or carrier.

Acceptable carriers are well known to those of skill in the art and can include, but not be limited to any of the standard pharmaceutical carriers, such as phosphate buffered saline, water and emulsions, such as oil/water emulsions and various types of wetting agents.

As used herein, pharmaceutical formulation means a therapeutically effective formulation according to the invention.

A therapeutically effective amount, or effective amount, or therapeutically effective, as used herein, refers to that amount which provides a therapeutic effect for a given condition and administration regimen. This is predetermined quantity of active material calculated to produce a desired therapeutic effect in association with the required additive and diluent, i.e. a carrier or administration vehicle. Further, it is intended to mean an amount sufficient to inhibit, decrease, antagonize, reduce, suppress, or prevent a clinically significant deficit in the activity, function and response of the host. Alternatively, a therapeutically effective amount is sufficient to cause an improvement in a clinically significant condition in a host. As is appreciated by those skilled in the art, the amount of a composition may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

More particularly, an effective amount or therapeutically effective amount of an active agent or therapeutic agent such as the antagonist is an amount sufficient to produce the desired effect, e.g., inhibition of expression of a cytokine in comparison to the normal expression level detected in the absence of the present compositions, inhibition or decrease of one or more symptoms of an immune modulated disease, neurodegenerative disease, or metabolic disease. Inhibition of expression of a cytokine is achieved when the value obtained is with an antagonist relative to the control is about 95%, 90%, 85%, 80%, 75%, 70%, 65%, 60%, 55%, 50%, 45%, 40%, 35%, 30%, 25%, 20%, 15%, 10%, 5%, or 0% of the value obtained with a control composition. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, as well as phenotypic assays known to those of skill in the art.

It will be appreciated by persons skilled in the art that the compositions of the invention will generally be administered in admixture with a suitable pharmaceutical excipient, diluent or carrier selected with regard to the intended route of administration and standard pharmaceutical practice (for example, see Remington: The Science and Practice of Pharmacy, 19th edition, 1995, Ed. Alfonso Gennaro, Mack Publishing Company, Pennsylvania, USA).

In one embodiment, the pharmaceutical formulation of the present invention is a unit dosage containing a daily dose or unit, daily sub-dose or an appropriate fraction thereof, of the active ingredient. Alternatively, the unit dosage may contain a dose (or sub-dose) for delivery at longer intervals, for example bi-weekly, weekly, bi-monthly, monthly, or longer.

The compositions and pharmaceutical formulations thereof will normally be administered intranasally, by inhalation, or by any parenteral route, in the form of a pharmaceutical formulation comprising the active ingredient, in a pharmaceutically acceptable dosage form. Depending upon the disease or disorder and patient to be treated, as well as the route of administration, the compositions may be administered at varying doses. In one embodiment, the present compositions are administered by inhalation or by a parenteral route.

In human therapy, the compositions of the invention can be administered alone but will generally be administered in admixture with a suitable pharmaceutical excipient, diluent or carrier selected with regard to the intended route of administration and standard pharmaceutical practice.

The compositions of the invention can be administered parenterally, for example, intravenously (i.v.), intra-articularly, intra-arterially, intraperitoneally (i.p.), intra-thecaliy, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH or from 3 to 9), if necessary. The preparation of suitable formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For parenteral administration to human patients, the daily dosage level of the compositions of the invention will usually be from 1 to 1000 mg per adult (i.e. from about 0.015 to 15 mg/kg), administered in single or divided doses.

The physician in any event will determine the actual dosage which will be most suitable for any individual patient and it will vary with the age, weight and response of the particular patient. The above dosages are merely exemplary of the average case. There can, of course, be individual instances where higher or lower dosage ranges are merited and such are within the scope of this invention.

Generally, in humans, parenteral administration of the compositions of the invention is the preferred route, being the most convenient.

It will be appreciated by persons skilled in the art that such an effective amount of the composition or formulation thereof may be delivered as a single bolus dose (i.e. acute administration) or, more preferably, as a series of doses over time (i.e. chronic administration).

It will be further appreciated by persons skilled in the art that the compositions and pharmaceutical formulations thereof have utility in both the medical and veterinary fields.

Thus, the methods of the invention may be used in the treatment of both human and non-human animals (such as horses, dogs and cats). In a particular embodiment, however, the patient is human.

For veterinary use, a composition of the invention is administered as a suitably acceptable formulation in accordance with normal veterinary practice and the veterinary surgeon will determine the dosing regimen and route of administration which will be most appropriate for a particular animal.

Thus a further embodiment provides a pharmaceutical formulation comprising an amount of a composition of the invention effective to modulate ICOS-mediated, TBK1-mediated, TBKBP1-mediated, IRF4-mediated, IKKβ-mediated, and/or BATF-mediated signaling in a patient, and a pharmaceutically and biochemically acceptable carrier suitable for parenteral administration in a human.

In a further aspect of the invention, there is provided a composition or a pharmaceutical formulation for use in medicine.

A further aspect of the present compositions includes a method of treating an immune modulated disease, neurodegenerative disease, cancer, metabolic disease, or a condition caused by an immunodeficiency by administering the composition or a pharmaceutical formulation thereof to a patient having the immune modulated disease, neurodegenerative disease, cancer or metabolic disease. In one aspect, the present compositions may be used for the treatment of immune modulated disease. As used herein "immune modulated diseases" include autoimmune diseases as discussed above and such diseases as multiple sclerosis, experimental autoimmune encephalomyelitis (both relapsing and remitting), inflammatory conditions (such as rheumatoid arthritis), allergic disorders (such as anaphylactic hypersensitivity, asthma, allergic rhinitis, atopic dermatitis, vernal conjunctivitis, eczema, urticarial, food allergies, allergic encephalomyelitis, multiple sclerosis, insulin-dependent diabetes mellitus, and autoimmune uveoretinitis), inflammatory bowel disease (e.g., Crohn's disease, regional enteritis, distal ileitis, granulomatous enteritis, regional ileitis, terminal ileitis, ulcerative colitis), autoimmune thyroid disease, hypertension, infectious diseases (such as *Leishmania major, Mycobacterium leprae, Candida albicans, Toxoplasma gondi*, respiratory syncytial virus, human immunodeficiency virus), allograft rejection (such as graft vs host disease), airway hyper reactivity, atherosclerosis, inflammatory liver disease, amyotrophic lateral sclerosis (ALS), and cancer. In a particular aspect, the immune modulated disease may be allograft rejection (such as graft vs host disease), airway hyper reactivity, atherosclerosis, inflammatory liver disease, and cancer. In one aspect, the composition used for treatment of cancer is an agonist of one or more activities of the ICOS/TBK1 pathway, such as ICOS/TBK1-mediated signaling. In one aspect, the composition used for treatment of an autoimmune disease or an inflammatory disease is an antagonist of one or more activities of the ICOS/TBK1 pathway, such as ICOS/TBK1-mediated signaling.

In one particular embodiment, the present compositions may be used for treatment of a neurodegenerative disease such as one or more of dementia, motor neuron disease, Tay-Sachs disease, ataxia telangiectasia, Baggio-Yoshinari syndrome, Batten disease, Corticobasal degeneration, Creutzfeldt-Jakob disease, Fatal familial insomnia, Parkinson's disease, neuropathy, JUNQ and IPOD, Lyme disease, Locomotor ataxia, Machado-Joseph disease, multipal system atrophy, ALS, Refsum disease, pyruvate dehydrogenase deficiency, protein aggregation diseases (such as Alzheimer's, Parkinson's, prion disease, amyloidosis, and ALS), toxic leukoencephalopathy, toxic encephalopathy, tabes *dorsalis*, subacute sclerosing panencephalitis, Lichtheim's disease, spinocerebellar ataxia, and Sandhoff disease.

In yet another particular embodiment, the present compositions may be used for treatment of metabolic diseases including obesity, huyperthyroidism, hypothyroidism, diabetes (type I or type II), dyslipidemia, hypolipidemia, galactosemia, Tay Sachs disease, Pompe disease, and phenylketonuria. In one aspect, the composition used for treatment of an a metabolic disease is an antagonist of one or more activities of the ICOS/TBK1 pathway, such as ICOS/TBK1-mediated signaling.

In yet a further embodiment, the present compositions may be used for treatment of immunodeficiency diseases or disorders. Immunodeficiency disorders include deficiencies in B-cells, combined T- and B-cell deficiencies, phagocyte deficiencies, complement deficiencies, and periodic fevers related to an immunodeficiency. Immunodeficiency disorders include B-cell deficiencies such as X-linked a gamma-globulinaemia (Bruton's Disease or XLA); common variable immunodeficiency (CVID); selective IgA deficiency; IgG subclass deficiency; immunodeficiency with thymoma, (Good Syndrome); Transient Hypoagammaglobulinaemia of infancy (THI); and hyper IgM syndrome—AR (AID deficiency). T cell and combined T and B cell deficiencies include: severe combined immunodeficiency, (SCID, several forms); CATCH 22 syndrome, (Digeorge's syndrome); X-Linked Lymphoproliferative syndrome (Duncan's syndrome); Hyper IgM syndrome—XI (CD40 ligand deficiency); MHC Class II deficiency (Bare Lymphocytes); Ataxia-teleangiectasia (Louis Bar's Syndrome); Wiskott-Aldrich's Syndrome; IPEX; Hyper IgM syndromes (AR—forms); and Chronic Mucocutaneous Candidiasis. Immunodeficiencies as described herein also include phagocyte deficiencies such as: Chronic Granulamotous Disease (CDG); deficiencies in Interferony/Interleukin-12 and receptors; Familial Hemophagocytic Lymphohistiocytosis (FHL); Congenital Agranulocytousis (Kostmann's Syndrome); Cyclid Neutropenia; Leukocyte Adhesion Deficiency (LAD); Chediak-Higashi's Syndrome; Griscelli's Syndrome (GS); and Hyper IgE Syndrome (HIES). Immunodeficiences as described herein also include complement deficiencies such as: Porperdin Deficiency; Mannan-Binding Lectin Deficiency (MBL); Hereditary Angioedema (HAE) and other complement deficiencies. Immunodeficiencies also include periodic fevers such as: TRAPS (tumor necrotic factor receptor associated periodic syndrome); Familial Mediterranean Fever (FMF); Hyper-IgD Syndrome (HIDS); PFAPA and others. In one embodiment, the composition used to treat an immunodeficiency is an agonist of ICOS/TBK1-mediated signaling.

A further aspect of the invention provides the use of a composition or a pharmaceutical formulation thereof in the preparation of a medicament for treating an immune modulated disease, a neurodegenerative disease, a metabolic disease, cancer, an immunodeficiency or a disease or condition capable of being treated by an agent that modulates ICOS-mediated, TBK1-mediated, TBK1 BP-mediated, I RF4-mediated, IKKβ-mediated, or BATF-mediated immune signaling. A related aspect of the invention provides a composition described herein or a pharmaceutical formulation thereof for treating a disease or condition capable of being treated by an agent which modulates ICOS-mediated, TBK1-mediated, TBK1BP-mediated, IRF4-mediated, IKKβ-mediated, and/or BATF-mediated immune signaling.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment. Furthermore, the treatment may be prophylactic. The term 'prophylactic is used to encompass the use of a composition or formulation thereof described herein which either prevents or reduces the likelihood of a condition or disease state in a patient or subject.

"Palliating" a disease or disorder means that the extent and/or undesirable clinical manifestations of a disorder or a disease state are lessened and/or time course of the progression is slowed or lengthened, as compared to not treating the disorder. A "delay" in the onset or recurrence of a symptom includes a delay of at least 1 hour, at least 2 hours, at least 6 hours, at least 12 hours, at least 24 hours, at least 48 hours, at least 72 hours, at least 1 week, at least 2 weeks, at least a month, at least three months, at least 6 months, or at least a year. Further, palliation does not necessarily occur by administration of one dose, but often occurs upon administration of a series of doses. Thus, an amount sufficient to palliate a response or disorder may be administered in one or more administrations.

In one embodiment, the present compositions prevent one or more symptoms of a condition, or of the generation of an immune response. The term "prevent" as used herein is applied to a patient, in whom symptoms have already been observed at some time in the past or in whom symptoms will develop due to the administration or presence of a triggering agent. By 'treatment' we include both therapeutic and prophylactic treatment of the patient.

To "suppress" or "inhibit" a function or activity, such as transcription, translation, cytokine production, antibody production, or histamine release, is to reduce the function or activity when compared to otherwise same conditions except for a condition or parameter of interest, or alternatively, as compared to another condition.

In yet a further embodiment, the present compositions (modified proteins and peptides, and pharmaceutical compositions) may be adjuvants. In one embodiment, the adjuvants may comprise an agonist of ICOS-mediated, TBK1-mediated, TBKBP1-mediated, IRF4-mediated, IKK?-mediated signaling, and/or BATF-mediated signaling.

Kits

Kits with unit doses of the subject compositions, usually in injectable doses, are provided. In such kits, in addition to the containers containing the unit doses will be an informational package insert describing the use and attendant benefits of the drugs in treating pathological condition of interest. Preferred compositions and unit doses are those described herein above.

EXAMPLES

Example 1: Materials and Methods

Antibodies (Abs) and reagents. Monoclonal antibodies (mAbs) specific for anti-human CD3 mAb (clone OKT3), and anti-mouse CD3 (clone 145-2C11), -CD28 (clone 37.51), -CTLA-4 (clone UC10-4B9) or -ICOS (clone C398.4A) were purchased from Biolegend, as was phycoerythrin-conjugated anti-CD150/SLAMfl (clone TC 15-12F12.2). Fluorophore-conjugated anti-CD4 (clone RM4-5), -CD8a (clone 53-6.7), -CD19 (clone eBio1D3), -CD25 (clone PC61), -CD4OL (clone MR1), -CD44 (clone IM7), -CD45.1 (clone A20), -CD62L (clone MEL-14), -GL7 (clone GL-7), -IgD (clone 11-26) and -PD1 (clone J43) mAbs were obtained from eBioscience. Anti-mouse CXCR5 (clone 2G8), biotinylated anti-CD138 (clone 281-2), FITC-conjugated TCR 13-chain (H57-597), phycoerythrin-conjugated anti-Fas/CD95 (clone Jo2) and allophycocyanin-conjugated anti-mouse Bcl6 (clone K112-91) were procured from BD Biosciences. FITC-conjugated PNA was purchased from Vector Laboratories. Monoclonal anti-TBK1 (#3013), -phospho-TBK1 (Ser172) (clone D52C2, #5483), -TRAF2 (#4712), -TRAF3 (#4729), p-ERK1/2 (T202/Y204) (clone E10, #9106) and -IKKE (#2690) Abs were obtained from Cell Signaling Technology. Monoclonal anti-p85α (sc-1637), -ERK2 (sc-1647) and -TRAF5 (sc-7220) were purchased from Santa Cruz Biotechnology. Recombinant IL-2 and IL-7 cytokines were obtained from Biolegend.

Plasmids. Plasmids of full-length human and mouse Icos were generated via PCR amplification and cloned into the pMIG retroviral vector. FLAG-tagged TRAF2 and TRAF3 clones were previously described (Sanjo H, Zajonc D M, Braden R, Norris P S, Ware C F. Allosteric Regulation of the Ubiquitin:NIK and Ubiquitin:TRAF3 E3 Ligases by the Lymphotoxin β Receptor. J Biol Chem 2010, 285(22): 17148-17155.). Point mutations in Icos, Traf2 and Traf3 cDNAs were generated using Quikchange II Site-directed Mutagenesis Kit (Stratagene).

The modified ICOS (IProx mutant) (170SSSVHDPNGE179 (SEQ ID NO: 24) to 170AAAAAAAAAA179 (SEQ ID NO: 22)) was generated using overlapping PCR. The tailless Icos mutant was generated via PCR amplification by inframe joining of amino acid 1-170 of ICOS to a flexible linker, LESGGGG (SEQ ID NO: 23), to stabilize its surface expression. Short hairpin RNA (shRNA) targeting the mouse Tbk1 gene (5'-AAGA-CATAAAGTGCTTATTATG-3' (SEQ ID NO: 59) or shTbk1-2: 5'-ACTAATCAGTGTTTCGATAT-3' (SEQ ID NO: 94)) and Icos gene (5'-TTCAGTTAATATGGTTTAC-TAT-3' (SEQ ID NO: 60)) were amplified via PCR and cloned into an LMP plasmid as previously described (Johnston et al., Science 2009, 325(5943): 1006-1010; Choi et al., Immunity 2011, 34(6): 932-946.; Chen et al., Immunity 2014, 41(2): 325-338, the entire contents of which are hereby incorporated by reference).

Mice and primary cell cultures. C57BL/6 (B6), TCR-transgenic SMARTA B6 mice expressing a TCR transgene recognizing the immunodominant MHC class II-restricted LCMV epitope GP61-80, SMARTA Icos$^{-/-}$ and CD4-Crex Bcl6$^{fl/fl}$ mice were housed and maintained under specific pathogen-free conditions, and manipulated according to guidelines approved by the LIAI Animal Care Committee. CD4$^+$ T cells were isolated by a CD4 negative selection kit (Miltenyi), and cultured in RPMI-1640 medium (Mediatech, Inc.) supplemented with 10% heat-inactivated fetal bovine serum, 2 mM glutamine, 1 mM sodium pyruvate, 1 mM MEM nonessential amino acids, and 100 Wml each of penicillin G and streptomycin (Life Technologies, CA). No statistical method was used to estimate the sample size. No pre-established inclusion/exclusion criteria were used for the analysis. Mice were randomly selected for adoptive transfer experiments, and investigators/experimenters were blinded from the group allocation when assessing the outcome.

Retroviral production, cell transfers and viral infections. ICOS-expressing retroviral plasmids and shRNA-carrying retroviral plasmids (pLMP) DNAs were transfected into Plat-E cell lines for virion production, as previously described with some modifications (Johnston et al., supra, Choi et al., supra, and Chen et al., supra). Cultured supernatants were obtained 1 day later, filtered through 0.45 μm syringe filters and spin-infected into in vitro activated SMARTA or Icos$^{-/-}$ SMARTA CD4$^+$ T cells by centrifugation at 2,000 rpm for 90 minutes at 37° C. Following two consecutive rounds of retroviral infection, CD4$^+$ T cells were maintained and expanded in the presence of 10 ng/ml of IL-2 for 2 days, and rested subsequently in the presence of 2 ng/ml of IL-7 overnight prior to cell sorting.

Retrovirally transduced GFP$^+$ or Ame$^+$ cells (5×10$^5$ and 2.5×10$^4$ cells 3- and 7-day experiments, respectively) were transferred into recipient mice by i.v. injection. LCMV Armstrong viral stocks were prepared and quantified as previously described. Fivex10$^5$ and 2×10$^5$ plaque-forming units (PFU) per mouse were inoculated i.p. for 3-, 5- and 7-day experiments, respectively.

Protein immunizations and B cell responses. 2×10$^5$ retrovirally transduced GFP$^+$ cells were transferred into CD4-crexBcl6$^{fl/fl}$ recipients by i.v. injection. A total of 20 μg of LCMV gp61-80 peptide (GLNGPDIYKGVYQFKSVEFD (SEQ ID NO: 61)) conjugated to keyhole limpet hemocyanin (KLH) was resuspended in alum and 2 μg LPS for i.p. injection. Spleens were obtained 10 days post-immunization for B cell analyses. For shRNA knockdown study, 2×10$^5$ retrovirally transduced Ametrine$^+$ cells were transferred into CD4-crexBcl6$^{fl/fl}$ recipients by i.v. injection. A total of 30 μg of LCMV gp61-80 peptide conjugated to keyhole limpet hemocyanin (KLH) was resuspended 1:1 in AddaVax (Invivogen Inc., San Diego Calif.) for footpad injection. Popliteal lymph nodes were obtained 10 days post-immunization for B cell analyses.

Flow cytometry. Single cell suspensions were prepared by a gentle mechanical disruption of spleens. The triple-step CXCR5 stains and intracellular Bcl6 stains were described previously (Johnston et al., supra, Choi et al., supra, and Chen et al., supra). All FACS samples were acquired with an LSRII (BD Biosciences) immediately after the staining protocol, and analyzed later with FlowJo (TreeStar, CA).

Immunofluorescence staining of germinal centers. Popliteal lymph nodes from mice immunized with KLH-gp61 were frozen in OCT medium (Sakura Finetek, USA), and 6-8 μm sections were prepared using a cryostat. LN sections were fixed with acetone, and stained with biotinylated-PNA followed by streptavidin conjugated to Alexa Fluor 555 (Life Technologies, CA), anti-IgD mAb conjugated to FITC, anti-CD4 mAb conjugated to Alexa Fluor 647 and DAPI to reveal the germinal centers, B cell zone, T cell zone and nuclei, respectively. Sectioned were fixed with mounted with ProLong gold antifade reagent (Life Technologies, CA), and imaged by Zeiss AxioScan Z1 Slide Scanner.

Immunofluorescence staining for localization study. Congenic CD45.1$^+$ Icos$^{-/-}$ SMARTA T cells were reconstituted with retroviral vector expressing WT ICOS or mlProx. 2×10$^6$ retrovirally transduced cells were sorted and transferred into CD45.2+ B6 recipients by i.v. injection. Fivex10$^5$ PFU of LCMV Armstrong were inoculated i.p. Spleens were frozen in OCT medium (Sakura Finetek, USA), and 6-8 μm sections were prepared using a cryostat. Spleen sections were fixed with acetone and stained with biotinylated-anti-CD45.1 mAb followed by streptavidin conjugated to Alexa Fluor 555 (Life Technologies, CA), anti-IgD mAb conjugated to FITC, anti-CD4 mAb conjugated to Alexa Fluor 647 and DAPI, to reveal the transferred T cells, B cell area, T cell zone and nuclei, respectively. Sectioned were fixed with mounted with ProLong gold antifade reagent (Life Technologies, CA), and imaged by Zeiss AxioScan Z1 Slide Scanner. To analyze the CD45.1+ SMARTA T cells in B cell follicles, first, a perimeter was manually drawn around the border between the T cell zone and B cell zone in a white pulp using a composite image of the CD4 and IgD stains, respectively. To identify SMARTA T cells, image of the CD45.1 stain was first masked using Otsu's method. An erosion and then dilation was performed on the cell mask, and objects smaller than cells removed from the mask. Cells inside the T-B border region were counted and normalized to the B cell areas. This was process was repeated for all identifiable B cell follicles in each spleen section.

Anti-KLH-gp61-80 ELISA. Sera were obtained through retro-orbital bleeding 10 days after protein immunization with KLH-gp61 plus adjuvants. 96-well PolySorp microtiter plates (Nunc, Thermo Scientific) were coated overnight with KLH-gp61-80 in PBS. Sera were serially titrated at 1:3 and incubated for 2 hours. After incubation of sample serum, plates were washed and then incubated with horseradish peroxidase-conjugated goat antibody to mouse IgG, followed by colometric detection with tetramethylbenzidine substrate solution (172-1068; Bio-Rad). Reaction was terminated using 2N sulfuric acid and the absorbance was read at 450 nm. Data were analyzed by two methods, endpoint titer and area under the curve (AUC). Endpoint titers of log transformed data were calculated as the interpolated serum dilution at 0.1 OD above background. AUC analysis better accounts for both the quantity and quality of the IgG, as it accounts for the shape of the curve. AUC total peak area above baseline calculations (Graphpad Prism 6.0) were done for each individual sample, log transformed.

Immunoprecipitation and immunoblotting. The human leukemic Jurkat T cell line, JTAg, was previously described (Li, J et al. J Immunol 2013, 191(1): 200-207; Rolf J et al., J Immunol 2010, 185(7): 4042-4052) and the HEK 293T cell line was obtained from ATCC. These cell lines have not been recently STR profiled but tested negative for *mycoplasma* contamination. JTAg cells in logarithmic growth phase were transfected with plasmid DNAs by electroporation and incubated for 24 hours. Transfection of HEK293T cells was carried out via liposomes-mediated transfection with plasmid DNAs. For experiments using primary mouse T cells, purified CD4+ T cells were activated in vitro with anti-mouse CD3 (clone 145-2C11) and CD28 (clone 37.51) for 48 hours prior to resting in the presence of IL-2 for another 48 hours. Transfected JTAg cells and preactivated mouse CD4+ T cells were stimulated with anti-CD3 and anti-ICOS (clone C398.4A) monoclonal antibodies (mAbs) in the presence of a cross-linking antibody (Ab) for 2 minutes. Cell lysis in 1% NP-40 lysis buffer (50 mM TrisHCl, pH 7.4, 50 mM NaCl, 5 mM EDTA), immunoprecipitation, and immunoblotting were carried out as previously described (Kong K F, et al., Nat Immunol 2011, 12(11): 1105-1112, the entire contents of which are hereby incorporated by reference). The intensity of bands was measured using the ImageJ software (NIH). To determine the ratio of TBK1 to p85a, the band intensity on IP blots and WCL blots were measured for TBK1 and p85a, respectively, and the ratio was expressed as (IP TBK1)/(WCL TBK1): (IP p85a)/(WCL p85a).

Isolation of mRNA, cDNA synthesis and real-time PCR. Total RNA was extracted from sorted CD4+ Ametrine- and CD4+ Ametrine+ cells using the RNeasy kit (Qiagen). RNA was used to synthesize cDNA by the SuperScript III First-Strand cDNA synthesis kit (Life Technologies). Gene expression was determined using real-time PCR with iTaq SYBR Green (Bio-Rad) in the presence of the following primer sets for mouse Icos (Forward: 5'-ACTGGT-GATCTCTATGCTGTCA-3' (SEQ ID NO: 62); Reverse: 5'-TTCTGGAAGTCCATACGCATTG-3')(SEQ ID NO: 63), Tbk1 (Forward: 5'-TGACCCACCTCCTTTTCAAG-3' (SEQ ID NO: 64); Reverse: 5'-TTAGGGT-CATGCACACTGGA-3'(SEQ ID NO: 65)) and the house-keeping gene 13-actin (ACTB). Relative gene expression levels were determined in triplicates, calculated using the 2-° Act method and normalized to the level of ACTB.

SILAC and proteomic analysis. Plasmids expressing WT ICOS and ICOS with mutated proximal motif (mlProx) were transfected into JTAg cells as described above in regular RPMI-1640 medium or medium supplemented with $^{13}C$ $^{15}N$ labeled lysine and arginine for SILAC labeling (Kong K F, et al., Nat Immunol 2014, 15(5): 465-472.). FACS-sorted GFP+ transduced cells were stimulated with a-CD3 plus a-ICOS mAbs for 2 minutes. 300 μg of the protein mixture derived from WT and mutant cell lysate were mixed at a 1:1 ratio, and immunoprecipitated with anti-ICOS mAb. Immunoprecipitants were subjected to an on-bead digestion protocol. The proteins were reduced with 100 mM Tris-HCl/8 M urea/5 mM tris(2-carboxyethyl)phosphine, and alkylated with 10 mM iodoacetamide. The solution was diluted 1:4 and digested with 1 μg of trypsin at 37° C. overnight. Digestion was terminated by adding 2% formic acid, and the resulting peptides were subjected to 6-step MudPIT LC-MS/MS analysis as described previously (Washburn M P, et al., Nat Biotechnol 2001, 19(3): 242-247). MS analysis was performed using an LTQ-Orbitrap Velos mass spectrometer (Thermo Fisher). A cycle of one full-scan mass spectrum (300-1800 rn/z) at a resolution of 60,000 followed by 20 data dependent MS/MS spectra at a 35% normalized collision energy was repeated continuously throughout each step of the multidimensional separation. The experiments were biologically repeated in four replicates, including medium isotope type swapping (heavy or light) between WT and mutant cells.

The mass spec data were analyzed by the Integrated Proteomics Pipeline—IP2 (Integrated Proteomics Applications, Inc., San Diego, Calif.) using ProLuCID, DTASelect2 (Tabb D L, et al., J Proteome Res 2002, 1(1): 21-26) and Census (Park S K, et al., Nat Methods 2008, 5(4): 319-322).

The tandem mass spectra were searched against EBI IPI human target/decoy protein database. The protein false discovery rates were controlled below 1% for each sample. In ProLuCID database search, the cysteine carboxyamidomethylation was set as a stable modification. The peptide quantification was performed by Census software, in which the isotopic distributions for both the unlabeled and labeled peptides were calculated and this information was then used to determine the appropriate m/z range from which to extract ion intensities.

Statistical analysis. Unless otherwise stated, statistical analyses were performed using the non-parametric Mann-Whitney U test for the comparison of two groups, and ANOVA with post-hoc Tukey's corrections for the comparison of more than two groups. P<0.05 was considered as statistically significant.

Example 2: Amino Acid Sequence Alignments

The IProx motif is required for the development of GC Tfh cells. Besides the PI3K-binding YXXM motif (see, e.g., SEQ ID NO: 19), the cytoplasmic tail of ICOS lacks known canonical motifs that mediate protein-protein interactions. To unveil other potential binding sites, we performed amino acid sequence alignments of the cytoplasmic tail in ICOS orthologs from primates, rodents, birds and amphibians (FIG. 1a). Intriguingly, this analysis revealed that, in addition to PI3K-binding motif, there are two additional highly conserved motifs in the intracellular domain of ICOS (FIG. 1a and Table 1).

TABLE 1

| | | | | |
|---|---|---|---|---|
| | Homology in ICOS | | | |
| Species | Sequence | SEQ ID NO | NCBI Accession | SEQ ID NO |
| Homo sapiens | KYSSSVHDPNGEYMFMRAVNTAKKSRLTDV | 42 | NP_036224 | 1 |
| Pan troglodytes | KYSSSVHDPNGEYMFMRAVNTAKKSRLTDV | 43 | XP_001173460 | 2 |
| Pongo abelii (Orangutan) | KYSSSVHDPNGEYMFMRAVNTAKKSKLTDVTI | 44 | XP_002812818 | 3 |
| Macaca mulatta | KYSSTVHDPNGEYMFMRAVNTAKKSRLTGTT | 45 | NP001253918 | 4 |
| Canis familiaris | KYRSSVHDPNSEYMFMAAVNTAKKPGLTGVTH NLELCGTQA | 46 | NP_001002972 | 5 |
| Fells catus | KYRSSGHDPNSEYMFMAAVNTAKKPGLTGVTH NLELCGTQA | 47 | XP_006935547 | 6 |
| Bos Taurus (Cow) | KYPTSVHDPNSEYMFMAAVNTAKKPGLTGVTH NLELCGTQA | 48 | NP_001029447 | 7 |
| Ailuropoda melanoleuca (Panda) | KYRSSVHDPNSEYMFMAAVNTAKKPGVTGVTH NLELCGTQA | 49 | XP_002919993 | 8 |
| Mus musculus | KYGSSVHDPNSEYMFMAAVNTNKKSRLAGTA | 50 | NP_059508 | 9 |
| Rattus norvegicus | KYRSSVHDPNSEYMFMAAVNTNKKSRLAGMTS | 51 | NP_072132 | 10 |
| Oryctolagus cuniculus (Rabbit) | KYQSSVHDPNSEYMFMAAVNTAKKPTPPVIL | 52 | XP_008257233 | 11 |
| Ornithorhynchus anatinus (Platypus) | QCPSSLHEPNSEYMPMAAVTAAKKSGFR | 53 | XP_007662906 | 12 |
| Meleagris gallopavo (Turkey) | QCESSSHEYNSEYMPMAAVNAAKKPRI | 54 | XP_003207549 | 13 |
| Gallus | QCESNSHEYNSEYMPMAAVNAAKKPRI | 55 | NP_001093758 | 14 |
| Anas platyrhynchos (Mallard) | QCESNSHEYNSEYMPMAAVNAAKKTRI | 56 | XP_005016889 | 15 |
| Taeniopygia guttata (Zebra finch) | KCESNSHEYNSEYMPMAAVNAAKKPRI | 57 | XP_002199832 | 16 |
| Xenopus tropicalis | QGNTQNNECNSEYMPMASVNPAKRPVIPRL | 58 | XP_002936434 | 17 |

Proximal motif (IProx) underlined;
YXXM motif bold;
Distal motif double underlined The finding of the YxxM (SEQ ID NO: 19) motif as one of the three conserved motifs validated our bioinformatics search. The other two conserved motifs are the proximal motif shown in SEQ ID NO: 18, (e.g., in human, 170SSSVHDPNGE179 (SEQ ID NO: 24)) and the distal motif shown in SEQ ID NO: 20 (e.g., in human, 186AVN-TAKK193 (SEQ ID NO:26)). The conservation of these two motifs suggested that they have important function(s), and potentially the recruitment of other molecule(s) that may mediate downstream ICOS signaling.

Example 3: Functional Analysis of Modified ICOS Proteins

Figure 8:
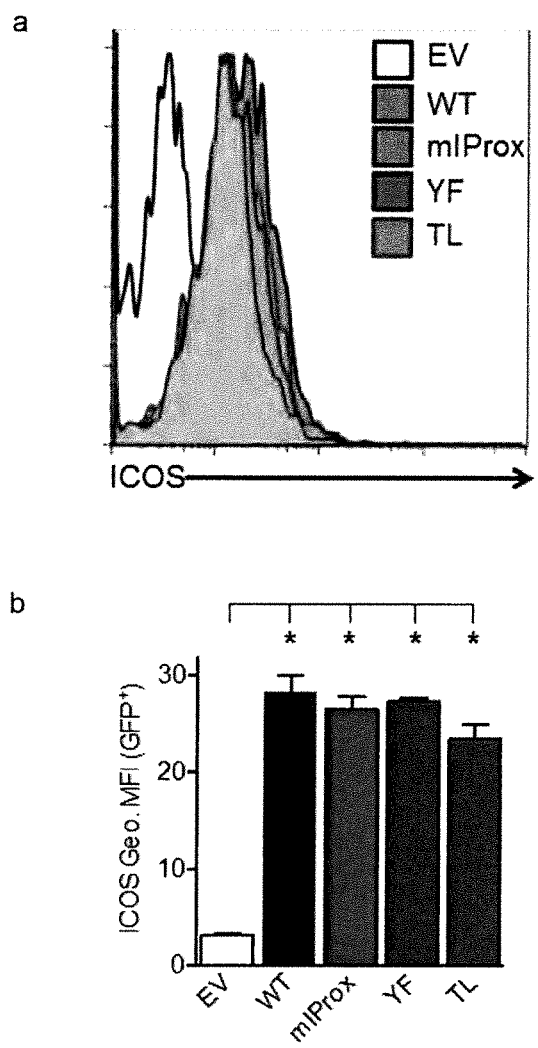
FIG. 8. Surface expression of reconstituted ICOS. SMARTA Icos$^{-/-}$ cells transduced with RV encoding WT ICOS, ICOS with alanine-substituted IProx motif (mIProx), mutation of the PI3K-binding site (Y181F; YF), or tailless (deletion of amino acid residues 170-200; TL) were adoptively transferred into B6 mice, which were infected with LCMV Armstrong strain and analyzed 7 d later. Shown are histograms of cells gated on CD4+CD44.+GFP+ (a) with geometric mean fluorescent intensity of ICOS protein expression in CD4+GFP+ T cells (b). *P<0.01; ANOVA with post-hoc Tukey's corrections analysis.

We focused on the proximal motif, for example in human, 170SSSVHDPNGE179 (SEQ ID NO: 24) (IProx). To examine the physiologic significance of this motif, we generated retroviral (RV) vectors that express wild-type (WT) ICOS or three ICOS mutants, i.e. replacement of the IProx motif by a string of 10 Ala substitutions (Ser170_Glu179>A1a; in mIProx), mutation of the PI3K-binding site (Y181F; YF), and deletion of the cytoplasmic tail (amino acid residues 170-200 of mouse ICOS; TL), respectively. The corresponding RV were used to reconstitute ICOS expression in $Icos^{-/-}$ TCR-transgenic SMARTA $CD4^+$ T cells. All transduced LCOS proteins displayed a similar level of surface expression in the reconstituted cells (FIG. 8). Sorted transduced ($GFP^+$) cells were adoptively transferred into B6 recipient mice, and analyzed 7 days after an acute infection with LCMV Armstrong strain. As expected, Icos-1-SMARTA $CD4^+$ T cells reconstituted with WT ICOS differentiated into $CXCR5^+SLAM^{lo}$ Tfh cells; in contrast, Ag-specific $CD4^+$ T cells reconstituted with each of the three LCOS mutants failed to generate the $CXCR5^+SLAM^{lo}$ Tfh cell population (FIGS. 1b & 1c), suggesting that, in addition to the PI3K-binding motif, the IProx motif is also required for of Tfh cell differentiation.

Example 4: Differentiation of GC Tfh Cells

Figure 9:
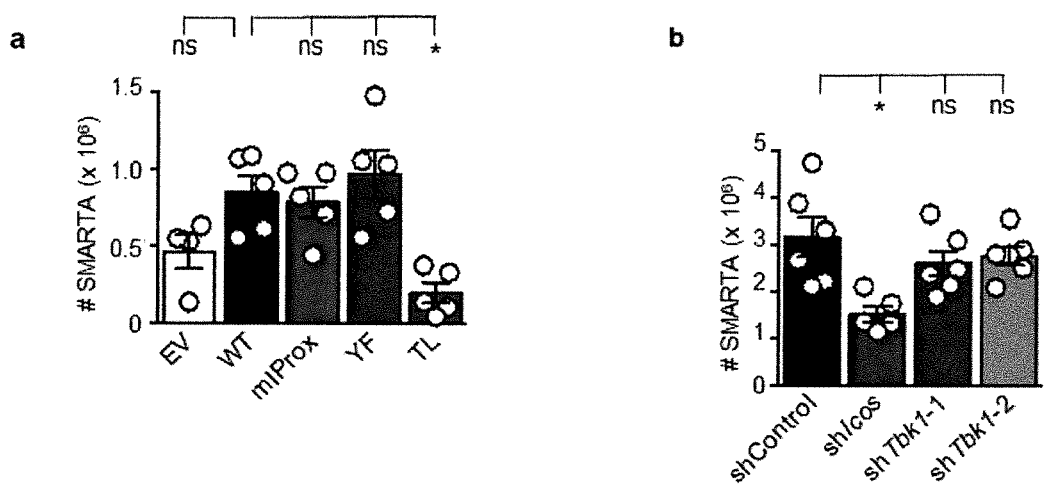
FIG. 9. Number of SMARTA CD4+ T cells in spleens. (a) SMARTA Icos$^{-/-}$ T cells were transduced with RV encoding WT ICOS, ICOS with alanine-substituted IProx motif (mlProx), mutation of the PI3K-binding site (Y181F; YF), or tailless (deletion of amino acid residues 170-200; TL), which were infected with LCMV Armstrong strain and analyzed 7 d later. Shown are cumulative data (mean±SEM) of CD4+GFP+ T cells from at least two independent experiments. Each data point represents a single mouse. (b) SMARTA CD4+ T cells transduced with shRNA targeting the Tbk1 (shTbk1-1 and shTbk1-2), Icos or control genes were adoptively transferred into B6 mice, which were infected with LCMV Armstrong strain and analyzed 7 d later. Shown are cumulative data (mean±SEM) of CD4+ Ametrine+ T cells from at least two independent experiments. Each data point represents a single mouse. *P<0.01; ANOVA with post-hoc Tukey's corrections analysis.

In addition, we also assessed the presence of GC Tfh cells, which express high levels of PD-1. The differentiation of $CXCR5^+PD1^{hi}$ GC Tfh cells was restored in $Icos^{-/-}$ SMARTA $CD4^+$ T cells reconstituted with WT ICOS, but remained significantly impaired upon reconstitution with each of the three ICOS mutants (FIGS. 1d & 1e). As internal controls, endogenous $CD4^+GFP$-cells were equally efficient in their GC Tfh differentiation in all groups (FIG. 9). As internal controls, endogenous $CD4^+GFP$-cells were equally efficient in their GC Tfh differentiation in all groups (FIG. 9a). With the exception of the TL mutant, we recovered similar levels of transduced cells in all groups (FIG. 10a), suggesting that the observed defects are not due to differences in T cell proliferation and/or cell death. Taken together, our data demonstrated that, in addition to the PI3K-binding motif, the IProx motif is also required for Tfh cell differentiation.

To further elucidate the physiologic relevance of the IProx motif in B cell responses, we performed similar transfers of Icos-1-SMARTA $CD4^+$ T cells transduced with the different ICOS RV into recipient mice with a CD4-specific conditional deletion of Bcl6 (in order to eliminate potential interference from endogenous Tfh cell responses).

The CD4-$Cre^+$ $Bcl6^{fl/fl}$ recipient mice are intrinsically unable to generate T-dependent B cell responses, despite having fully functional B cells. By virtue of the $Bcl6^{fl/fl}$ Tfh deficiency, the B cell responses generated are fully dependent on the ability of transferred T cells to differentiate into bona fide GC Tfh cells. Adoptive transferred mice were immunized with keyhole limpet hemocyanin (KLH)-conjugated LCMV gp61-80 peptide (KLH-gp61), and their responses were analyzed. As a benchmark for proper development of GC Tfh cells, the transfer of $Icos^{-/-}$ SMARTA $CD4^+$ T cells reconstituted with WT ICOS supported the differentiation of $Fas^+GL7^+$ GC B cells (FIG. 1f, 1g) and class-switched $IgD-CD138^+$ plasma cells (PC) in response to KLH-gp61 immunization (FIG. 1h, 1i). In sharp contrast, B cell differentiation was severely affected in the absence of a functional IProx motif, or PI3K-binding motif, or the complete absence of the ICOS intracellular tail, with GC B cell frequencies indistinguishable from the $Icos^{-/-}$ control (FIG. 1f-1i). Moreover, the anti-KLH-gp61 IgG response was greatly diminished in mice receiving $Icos^{-/-}$ $CD4^+$ T cells reconstituted with IProx ICOS, YF ICOS or tailless ICOS (FIG. 1j). Both the quantity and quality of the antigen-specific IgG response was significantly and severely impaired in the absence of either IProx-dependent or PI3K-dependent ICOS signaling (FIG. 1k, 1l). Therefore, the development of these antigen-specific T-dependent B cell responses required the provision of complete ICOS signaling involving both the IProx and YxxM motifs. These data strongly indicate that the IProx motif is required for the in vivo differentiation of GC Tfh cells.

Example 5: Physical Interaction of TBK1 and ICOS

TBK1 physically interacts with the proximal motif of ICOS. To identify putative molecule(s) that could bind to the IProx motif, we undertook an unbiased proteomic approach using stable isotope labeling by amino acid in cell culture (SILAC), which allows for quantitative comparative measurement of proteins. We analyzed the proteomes of ICOS immunoprecipitates (IPs) obtained from cells expressing WT ICOS or mIProx. We obtained >8,000 peptides from the screen, a strong indicator of good detection coverage. We applied a series of stringent selection criteria to the dataset, including >4 identifying peptides with significant difference (P<0.05) between WT and mIProx. One cytosolic protein, TANK-binding kinase 1 (TBK1), a non-canonical member of the IKB kinase (IKK) family, had the highest differential binding ratio (~8-fold) in WT- vs. mIProx-expressing cells (See Table 2).

TABLE 2

| IKK family Differential Binding Ratio | | |
|---|---|---|
| Protein | Putative Function | Fold Change |
| TBK1 | Signaling kinase | 7.69 |
| MYCBP2 | E3 ligase | 5.26 |
| BAG6 | Chaperone | 3.13 |
| NAA10 | Acetyltransferase | 2.95 |
| GAK | Cell cycle kinase | 2.17 |
| SLP76 | TCR signaling | 2.08 |
| Erlin2 | ER protein | 1.81 |
| GSTZ1 | Metabolism | 1.64 |
| KLC1 | Cytoskeleton | 1.59 |

TBK1 plays critical role in the production of Type I interferon by innate immune cells (Akira S and Takeda K. Nat Rev Immunol 2004, 4(7):499-511). However, the role of TBK1 in T cells has not been pinpointed.

Example 6: Co-ImmunoPrecipitation (co-IP) of ICOS

Figure 2:
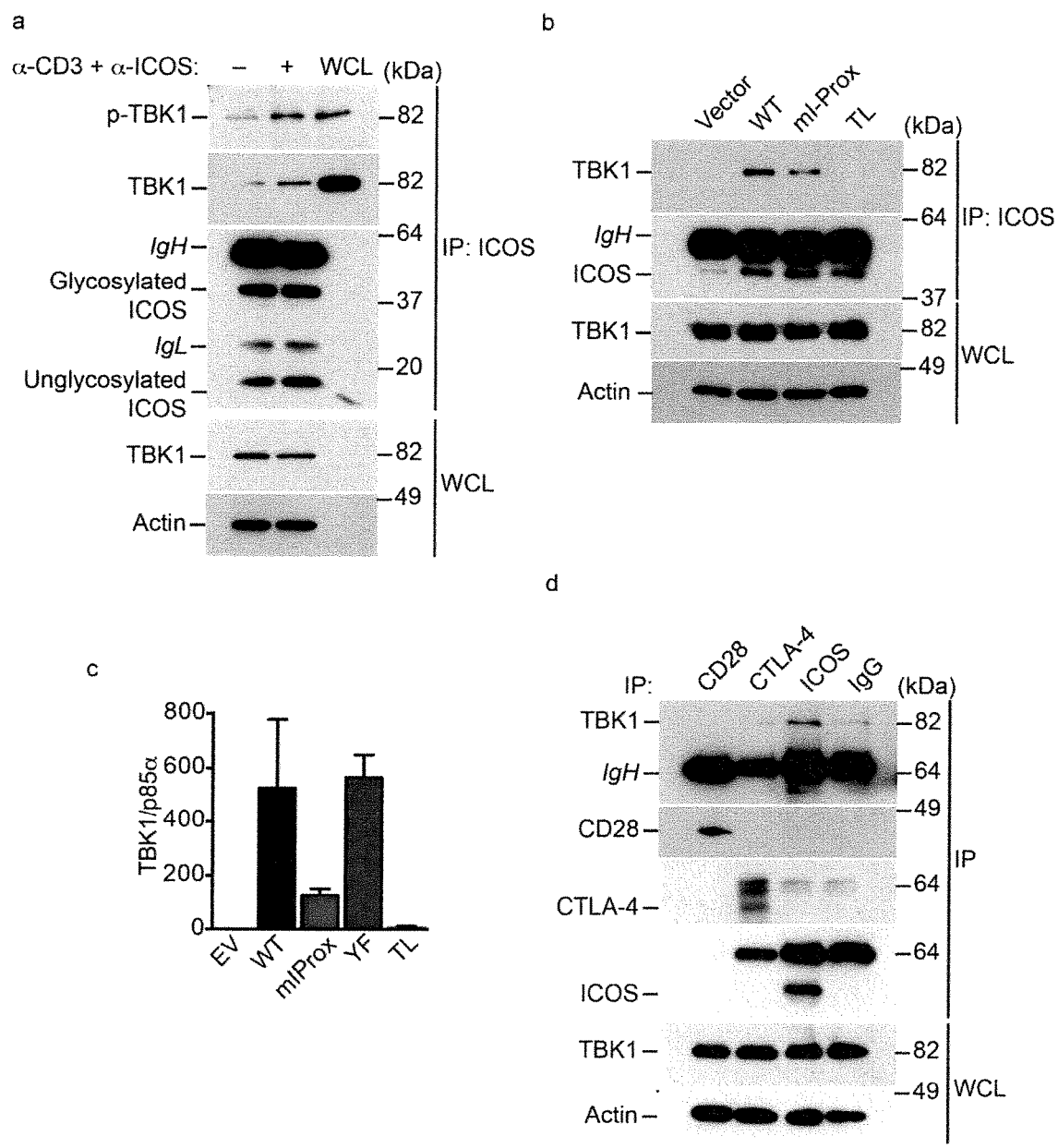
FIG. 2. ICOS-TBK1 interaction. Jurkat T cells transfected with WT ICOS or ICOS with mutated IProx motif (mIProx) were metabolically labeled and subjected to SILAC and mass spectrometric analysis following stimulation with anti-CD3 plus -ICOS mAbs and anti-ICOS IP. (a) ICOS IPs were prepared from mouse primary CD4$^+$ T cells activated in vitro with anti-CD3 plus -CD28 mAbs and rested in IL-2, followed by restimulation with anti-CD3 plus -ICOS mAbs. IPs or whole cell lysates (WCL) were immunoblotted with the indicated Abs. 5% WCL was used as input to control for IP Western. (b) IProx motif mediates ICOS-TBK1 interaction. Jurkat T cells transfected with WT ICOS, mIProx, YF or tailless (TL) ICOS plasmids were stimulated with anti-CD3 plus -ICOS mAbs prior to IP and immunoblotting. Intensity of TBK1 and p85α bands was quantified using ImageJ software and expressed as TBK1/p85α (c). Shown are mean±SEM. p>0.05 for comparative analyses of all groups; ANOVA with post-hoc Tukey's corrections. (d) Specific TBK1 association with ICOS. In vitro activated primary mouse CD4$^+$ T cells were stimulated with anti-CD3 plus the indicated costimulatory mAbs, and IP or WCL were subjected to immunoblotting with the indicated Abs. Shown are representative of three experiments.

To validate the proteomic data, we first performed a co-IP analysis and found that ICOS co-immunoprecipitated with endogenous TBK1 in pre-activated primary CD4+ T cells upon restimulation with anti-CD3 plus -ICOS mAbs; minimal interaction was observed in non-restimulated cells (FIG. 2a). More importantly, TBK1 phosphorylated on the activating residue[35] ($^{172}$S) was detected in ICOS immunoprecipitation, suggesting that LCOS can recruit the active form of TBK1. Next, we transfected Jurkat (JTAg) T cells with WT ICOS, mlProx or TL mutant, and analyzed the presence of TBK1 in ICOS IPs from stimulated cells. WT ICOS interacted strongly with endogenous TBK1, but the interaction was substantially reduced in cells expressing mlProx (FIG. 2b), consistent with the proteomic data. Mutation of tyrosine residue (Y181F) abolished the binding of p85α (the regulatory subunit of PI3K) without affecting the ICOS-TBK1 interaction, and binding of p85α to ICOS was not impaired in mlProx (FIG. 2b, 2c). In addition, we determined that TBK1 associated only with ICOS, but not with the closely related surface receptors, CD28 and CTLA-4 (FIG. 2d), demonstrating that this signaling pathway is unique to ICOS. Taken together, these data indicate that ICOS physically interacts with active TBK1 via the conserved IProx motif.

Example 7: RNAi Knockdown

TBK1 is required for the development of GC Tfh cells. Since we demonstrated that the IProx motif is required for Tfh development (FIG. 1), and that this motif physically interacts with TBK1 (FIG. 2), we hypothesized that TBK1 plays a role in the differentiation of Tfh cells. To test this hypothesis, we used an RNAi knockdown strategy. Similar knockdown approaches have been routinely and successfully used to establish the importance of different proteins, including Bcl6, in Tfh cell differentiation (Johnston R J, et al., Science 2009, 325(5943): 1006-1010; Choi et al., Immunity 2011, 34(6): 932-946; and Chen R, et al., Immunity 2014, 41(2): 325-338, the entire contents of each are hereby expressly incorporated by reference). Ag-specific SMARTA CD4+ T cells were retrovirally transduced with a modified LMP vector, which co-expresses short hairpin RNA (shRNA) targeting the Tbk1 gene (shTBK1-1 or shTBK1-2, FIG. 11a) and mAmetrine fluorescent protein (see Johnston et al., and Chen et al., supra). In parallel, we used LMP plasmids containing shRNA targeting an irrelevant gene (shControl) and Icos (shIcos), as negative and positive controls, respectively. Transduced mAmetrine+ SMARTA CD4+ T cells were adoptively transferred into B6 mice and analyzed 7 days post-LCMV infection to assess the development of the Tfh cells.

Figure 10:
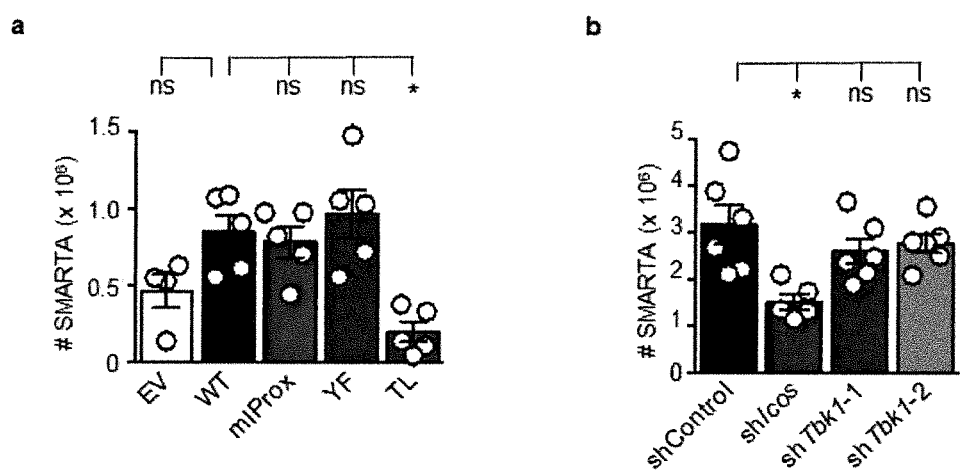
FIG. 10. Number of SMARTA CD4+ T cells in spleens. (a) SMARTA Icos$^{-/-}$ T cells were transduced with RV encoding VVT ICOS, ICOS with alanine-substituted IProx motif (mlProx), mutation of the PI3K-binding site (Y181F; YF), or tailless (deletion of amino acid residues 170-200; TL), which were infected with LCMV Armstrong strain and analyzed 7 d later. Shown are cumulative data (mean±SEM) of CD4+GFP+ T cells from at least two independent experiments. Each data point represents a single mouse. (b) SMARTA CD4+ T cells transduced with shRNA targeting the Tbk1 (shTbk1-1 and shTbk1-2), Icos or control genes were adoptively transferred into B6 mice, which were infected with LCMV Armstrong strain and analyzed 7 d later. Shown are cumulative data (mean±SEM) of CD4+ Annetrine+ T cells from at least two independent experiments. Each data point represents a single mouse. *P<0.01; ANOVA with post-hoc Tukey's corrections analysis.
Figure 11:
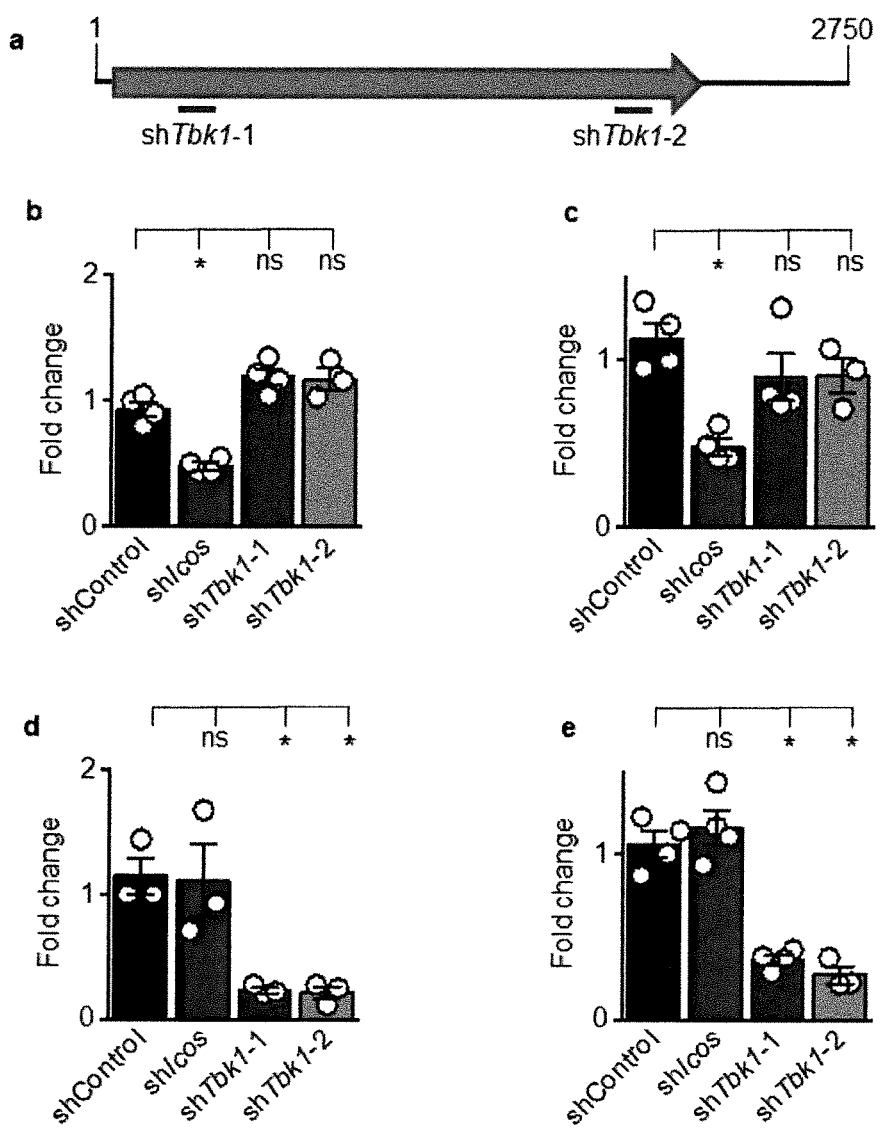
FIG. 11. In vivo knockdown efficiency of Icos and Tbk1 genes. (a) Schematic representation of mouse Tbk1 transcript of 2750 base pairs (blue arrow represents the open reading frame). Regions targeted by shTbk1-1 and shTbk1-2 are indicated with short red lines. (b-e) SMARTA CD4+ T cells transduced with shRNA targeting the Tbk1 (shTbk1-1 and shTbk1-2), Icos or control genes were adoptively transferred into B6 mice, which were infected with LCMV Armstrong strain for 3 d (b, d) and 7 d (c, e). Transduced cells (Ame+) were sorted and analyzed by quantitative PCR. Shown are the fold-change (mean±SEM) for the expression of Icos (b, c) and Tbk1 (d, e) in Anne+transduced cells from at least two independent experiments. Each data point represents a single mouse. *P<0.05; n.s., not significant; ANOVA with post-hoc Tukey's corrections analysis.

As expected, depletion of ICOS in SMARTA CD4+ T cells significantly reduced the CXCR5+SLAM$^{lo}$ Tfh cell population, as well as the CXCR5+PD1$^{hi}$ and CXCR5+GL-7+ GC Tfh cell populations (FIGS. 3a-3f). Importantly, knockdown of Tbk1 in Ag-specific CD4+ T cells also significantly impaired the full development of GC Tfh cell populations (FIGS. 3a-3f), demonstrating that TBK1 is critical for the full commitment of Tfh differentiation. The Tbk1 transcript was reduced by ~80% in vivo in sorted shTbk1+CD4+ T cells (FIG. 11d, 11e). SMARTA T cells containing shTbk1-1 or shTbk1-2 accumulated comparably to control SMARTA T cells in response to the acute viral infection (FIG. 10b). As an internal control, endogenous CD4+ T cells were equally efficient in their GC Tfh differentiation in all groups (FIG. 9b).

Figure 3:
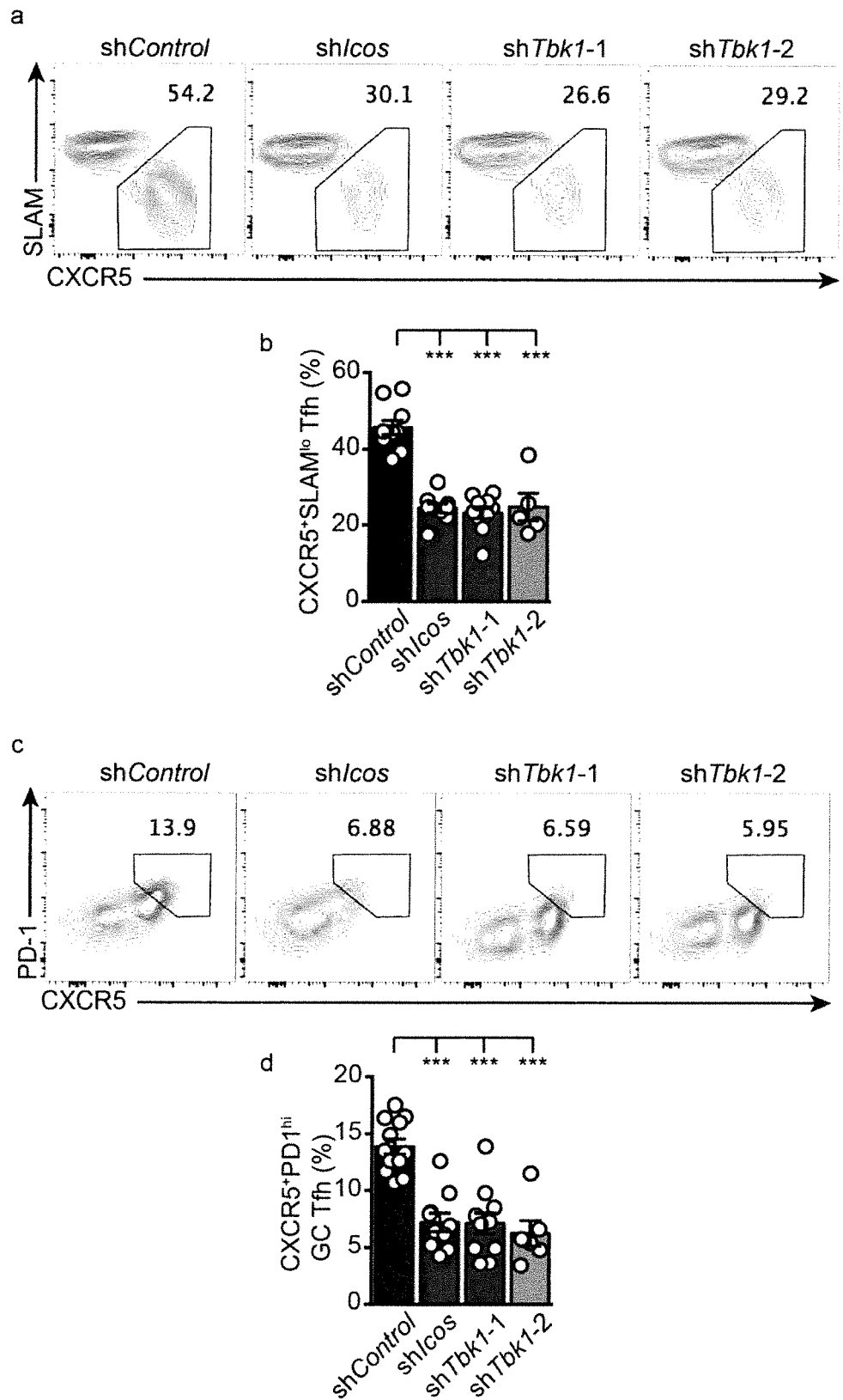
FIG. 3. TBK1 is required for Tfh cell differentiation. (a-f) SMARTA CD4$^+$ T cells transduced with shRNA targeting the Tbk1 (shTbk1-1 and shTbk1-2), Icos or control genes were adoptively transferred into B6 mice, which were infected with LCMV Armstrong strain. CXCR5$^+$SLAM$^{lo}$ Tfh cells (a, b), CXCR5$^+$PD1$^{hi}$GC Tfh cells (c, d), and CXCR5$^+$GL7$^+$GC Tfh cells (e, f) were analyzed 7 d later by FACS (a, c, e), with cumulative data from three independent experiments shown in (b, d, f). Each data point represents a single mouse. Shown are mean±SEM. (g-l) SMARTA CD4$^+$ T cells transduced as in (a) were adoptively transferred into CD4-CrexBc/6" recipients, which were immunized with KLH-gp61 suspended in AddaVax as an adjuvant. Shown are mean±SEM; ANOVA with post-hoc Tukey's corrections CD95$^+$GL7$^+$GC B cells were analyzed 10 d later by FACS (g), with cumulative data from two independent experiments (h). Anti-KLH-gp61 IgG from sera of mice immunized as in (g) were analyzed ELISA and presented as absorbance at 450 nm (l), and the endpoint titer (j) and area under curve (k) were calculated. Each data point represents a single mouse. Shown are mean±SEM; unpaired two-tailed Student's t-test. *P<0.001; **P<0.0001. (l) Representative immunofluorescence images of LN sections stained with PNA (red), anti-IgD mAb (green), and anti-CD4 mAb (blue) to reveal the germinal centers, B cell follicles and T cell areas, respectively. 20× magnification.
Figure 3:
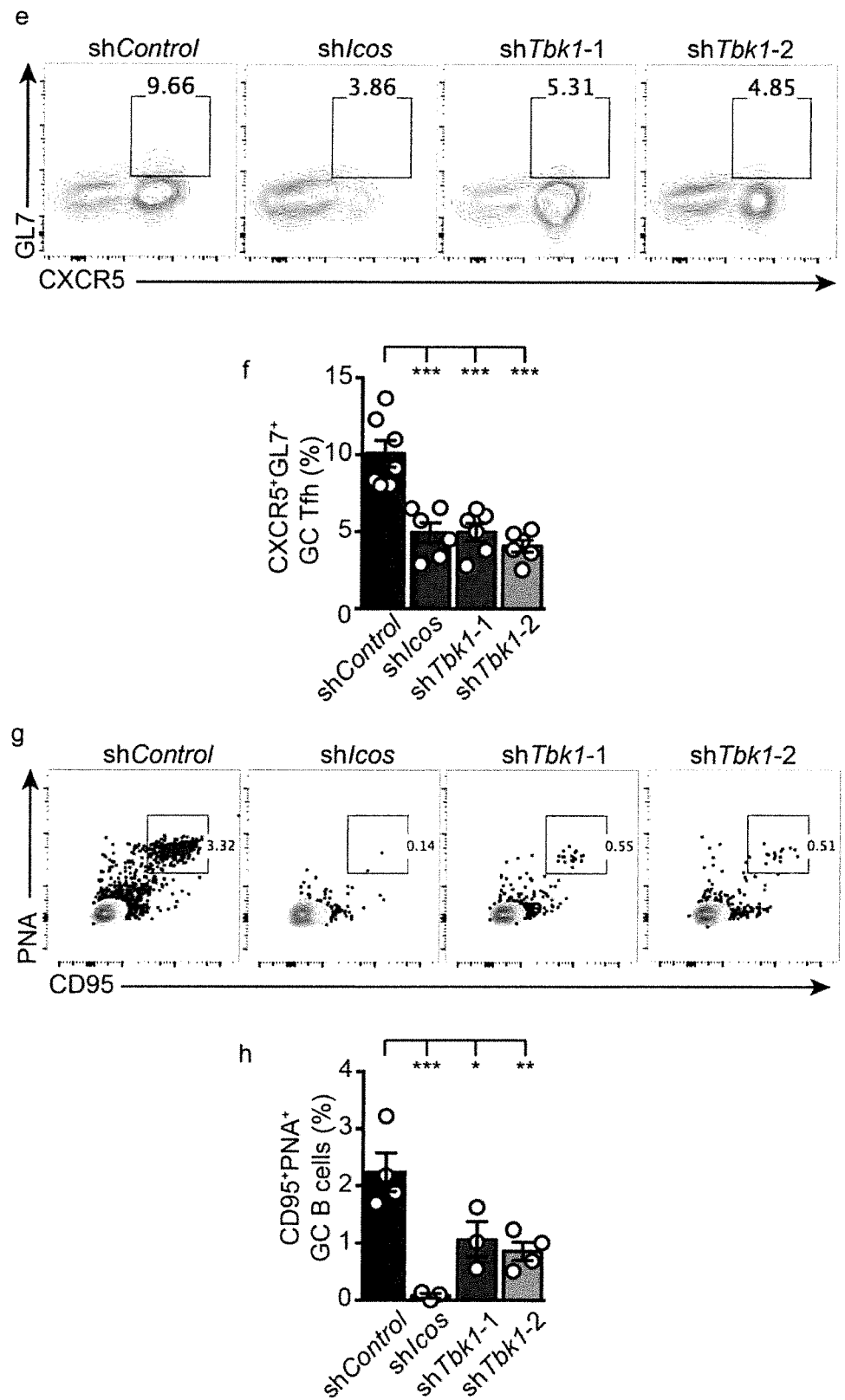
Figure 3:
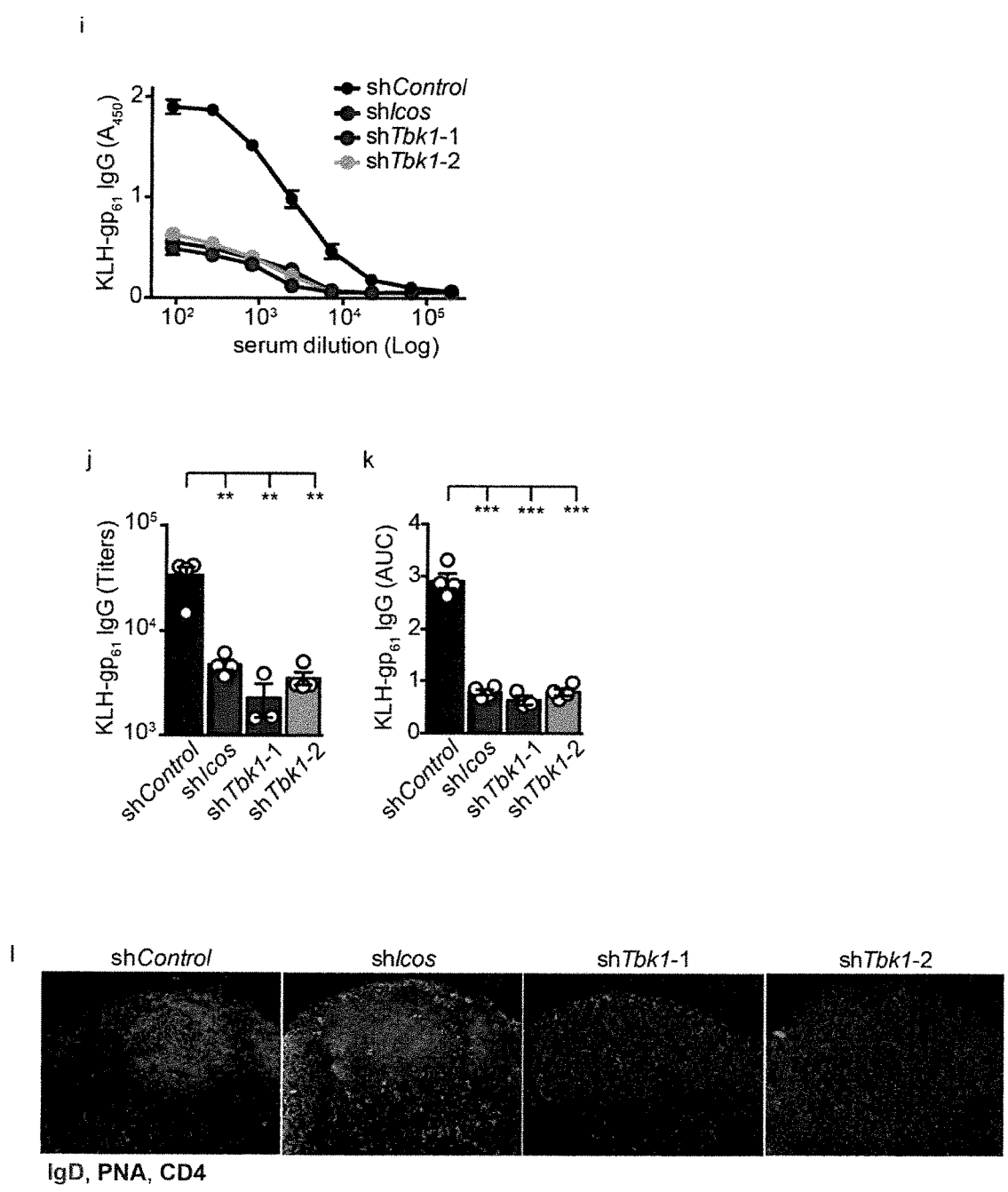

To assess the physiologic relevance of TBK1 in T-dependent B cell responses, we employed CD4-Cre+ Bcl6$^{fl/fl}$ mice immunized with KLH-gp61 and examined the germinal center and antibody responses supported by SMARTA T cells deficient in TBK1 expression. Germinal center B cell frequencies were significantly reduced when TBK1 was depleted in SMARTA CD4+ T cells (FIG. 3g, 3h), consistent with the loss of GC Tfh differentiation (FIGS. 3a-3f). Anti-KLH-gp61 specific IgG responses were also significantly impaired when ICOS or TBK1 was depleted (FIGS. 3i-3k). Anti-KLH-gp61 IgG titers were ~10-fold lower in the absence of an intact ICOS-TBK1 signaling pathway (FIG. 3j). Concomitantly, the architecture of PNA+ GCs was severely compromised in mice receiving shIcos+, shTbk1-1+ or shTbk1-2+ SMARTA CD4+ T cells, compared to controls (FIG. 3l), indicating that TBK1 in CD4+ T cells is required to support Tfh differentiation and the development of germinal centers and antigen-specific T-dependent IgG responses.

Example 8: Importance of IProx Motif in Tfh Cell Differentiation

Figure 4:
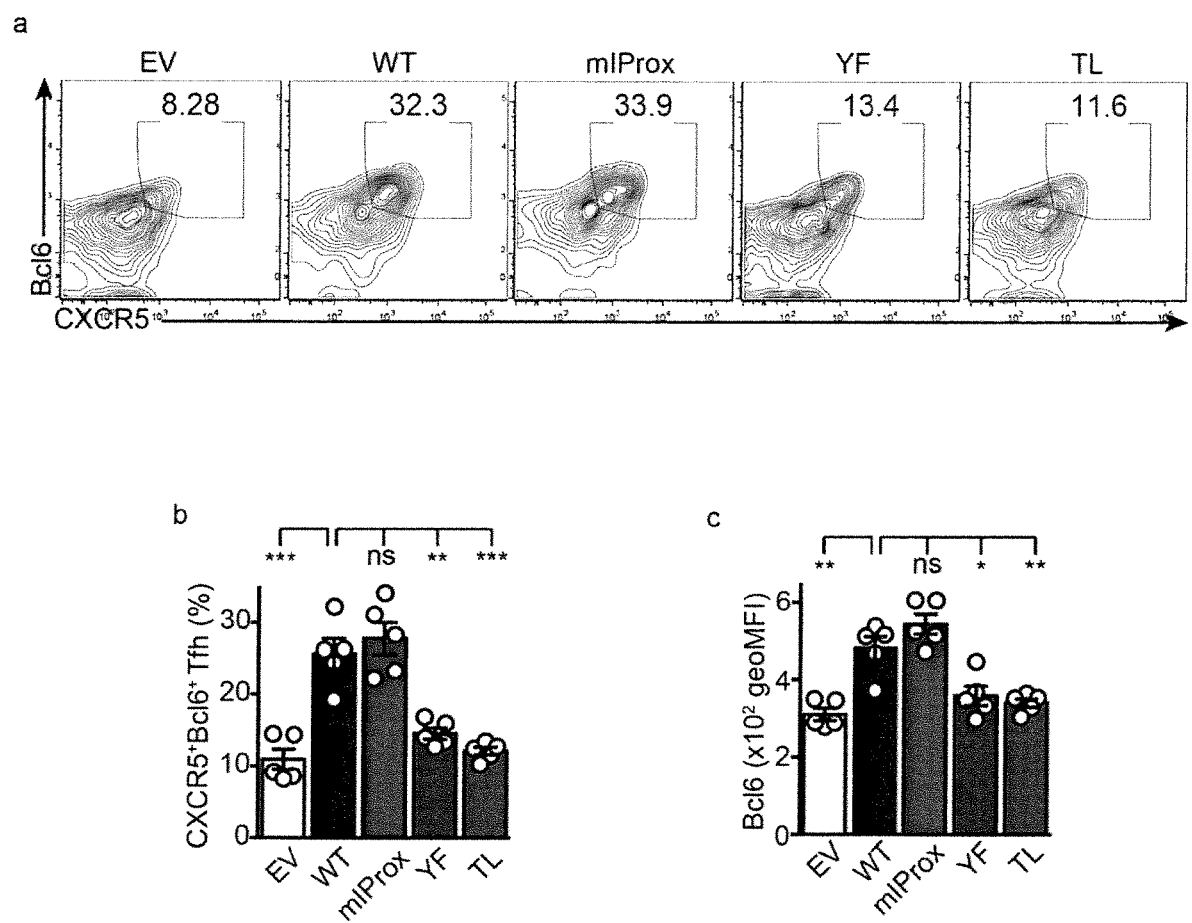
FIG. 4. The IProx ICOS motif is dispensable for the development of nascent Tfh cells. Icos$^{-/-}$ SMARTA CD4$^+$ T cells reconstituted with indicated ICOS constructs were adoptively transferred and infected with LCMV Armstrong strain. Bcl6+CXCR5+ (a, b), and CXCR5+CD25$^{lo}$ nascent Tfh cells (d, e) were analyzed 3 d later by FACS (a, d), with cumulative data from two independent experiments shown in (b, e). (c) Mean fluorescent intensity of Bcl6 protein in CD4+GFP+ T cells. Each data point represents a single mouse. Shown are mean±SEM. *P<0.01; P<0.001; *P<0.0001; ns: not significant; ANOVA with post-hoc Tukey's corrections. (f) Congenic CD45.1+Icos$^{-/-}$ SMARTA CD4+ T cells reconstituted with indicated ICOS constructs were adoptively transferred and infected with LCMV Armstrong strain. Four days later, spleen sections were stained with anti-CD45.1 (red), anti-IgD mAb (green), and anti-CD4 mAb (blue) to reveal the SMARTA cells, B cell follicles and T cell areas, respectively, and transferred CD45.1+ T cells found in B cell follicles and at the T:B border were enumerated and normalized to the area. Each data point represents a B cell follicle. Right panels are representative immunofluorescence images outlining B cell follicles and the identified CD45.1+ T cells transduced with WT ICOS or mIProx. Graph is mean±SEM; ns: not significant; Mann-Whitney U test.
Figure 4:
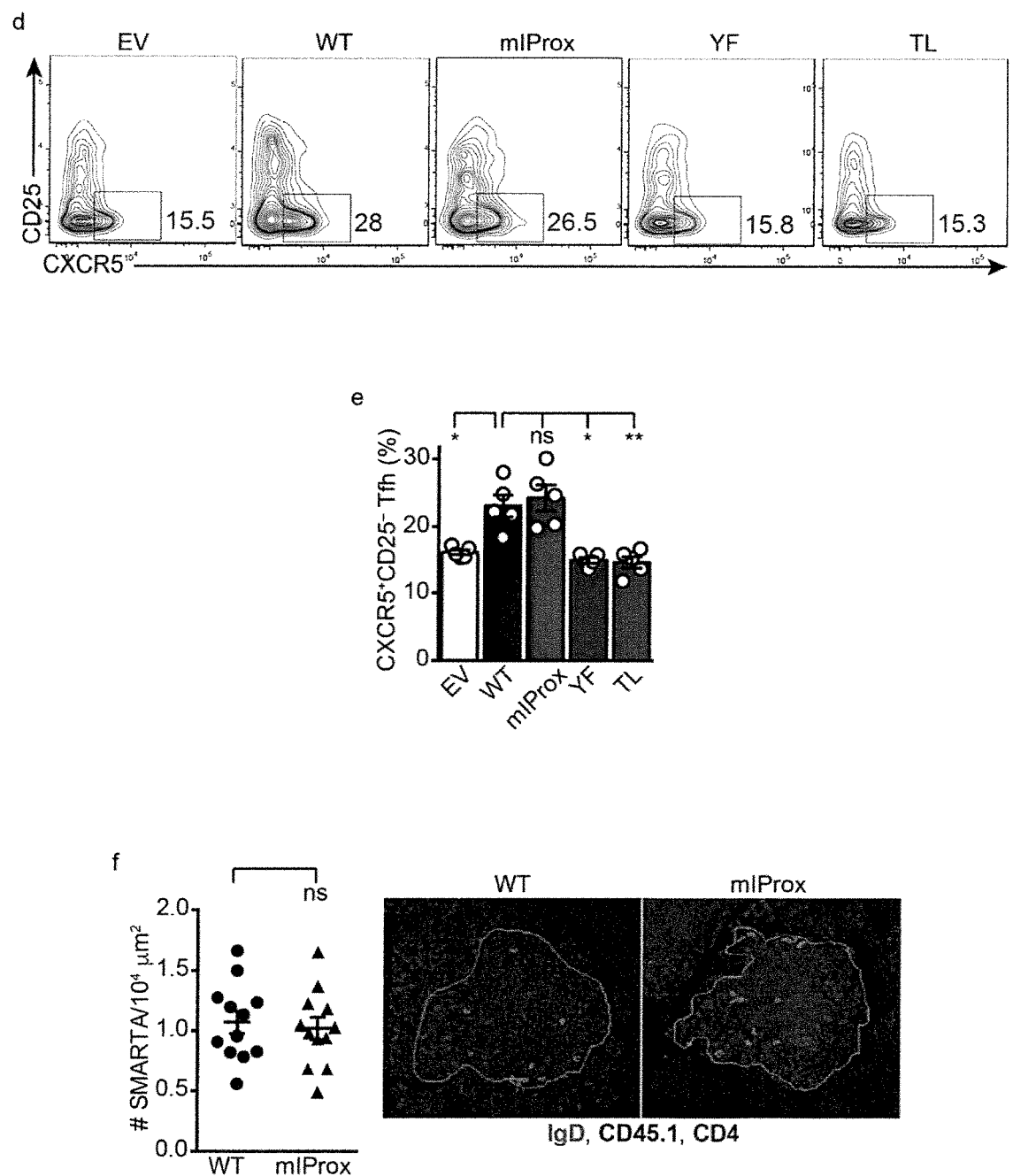

The IProx motif is dispensable for the development of nascent Tfh cells. The complete programming of Tfh cells is a multistep process involving T cell-DC interaction at the early stage and T-B cell interaction at a later phase (Choi et al., supra.; Goenka R, et al. J Immunol 2011, 187(3): 1091-1095; Barnett L G, et al., J Immunol 2014, 192(8): 3607-3617; and Kerfoot S M, et al., Immunity 2011, 34(6): 947-960, the entire contents of each are hereby incorporated by reference). To assess the importance of the IProx motif in the differentiation of nascent Tfh cells, we carried out a similar reconstitution and adoptive transfer experiment, but instead of analyzing the response 7 days post-LCMV infection, we performed the analysis earlier, i.e., after 3 days. Icos$^{-/-}$ SMARTA CD4+ T cells reconstituted with WT ICOS were able to differentiate into CXCR5+Bcl6+ Tfh cells. However, to our surprise, Icos$^{-/-}$ SMARTA CD4+ T cells reconstituted with the mlProx were equally capable of polarizing into nascent Tfh cells (FIGS. 4a & 4b). In contrast, Icos$^{-/-}$ SMARTA CD4+ T cells reconstituted with the YF or TL mutants failed to differentiate into the nascent Tfh cell population (FIGS. 4a & 4b). Additionally, the Bcl6 protein expression level was comparable between Ag-specific T cells reconstituted with WT or mlProx ICOS (FIG. 4c), indicating that the early expression of Bcl6, and potentially its regulatory functions, is independent of the IProx motif.

Example 9: Analysis of Tfh Cell Markers

Figure 12:
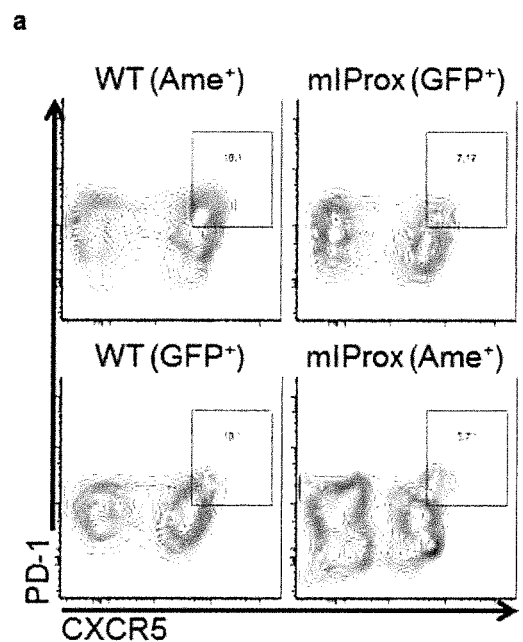
FIG. 12. Icos$^{-/-}$ SMARTA CD4+ T cells transduced with GFP+ or Ametrine (Ame+) RV encoding WT ICOS or ICOS with alanine-substituted IProx motif (mlProx) were co-transferred into B6 mice, which were infected with LCMV Armstrong strain. CXCR5+PD1$^{hi}$ GC Tfh cells (a) were analyzed 5 d later by FACS, with cumulative data from at least two independent experiments shown in (b). *P<0.001; Mann-Whitney U test.
Figure 12:
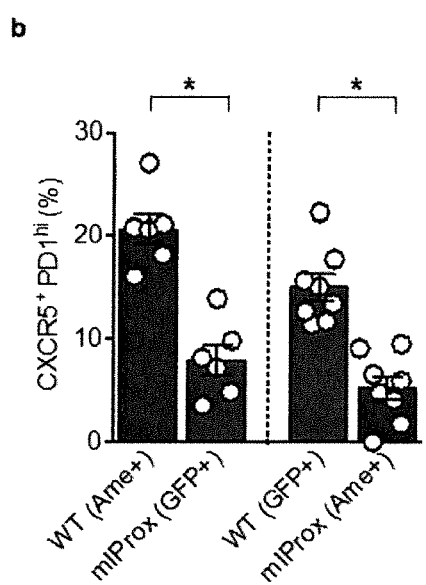
Figure 13:
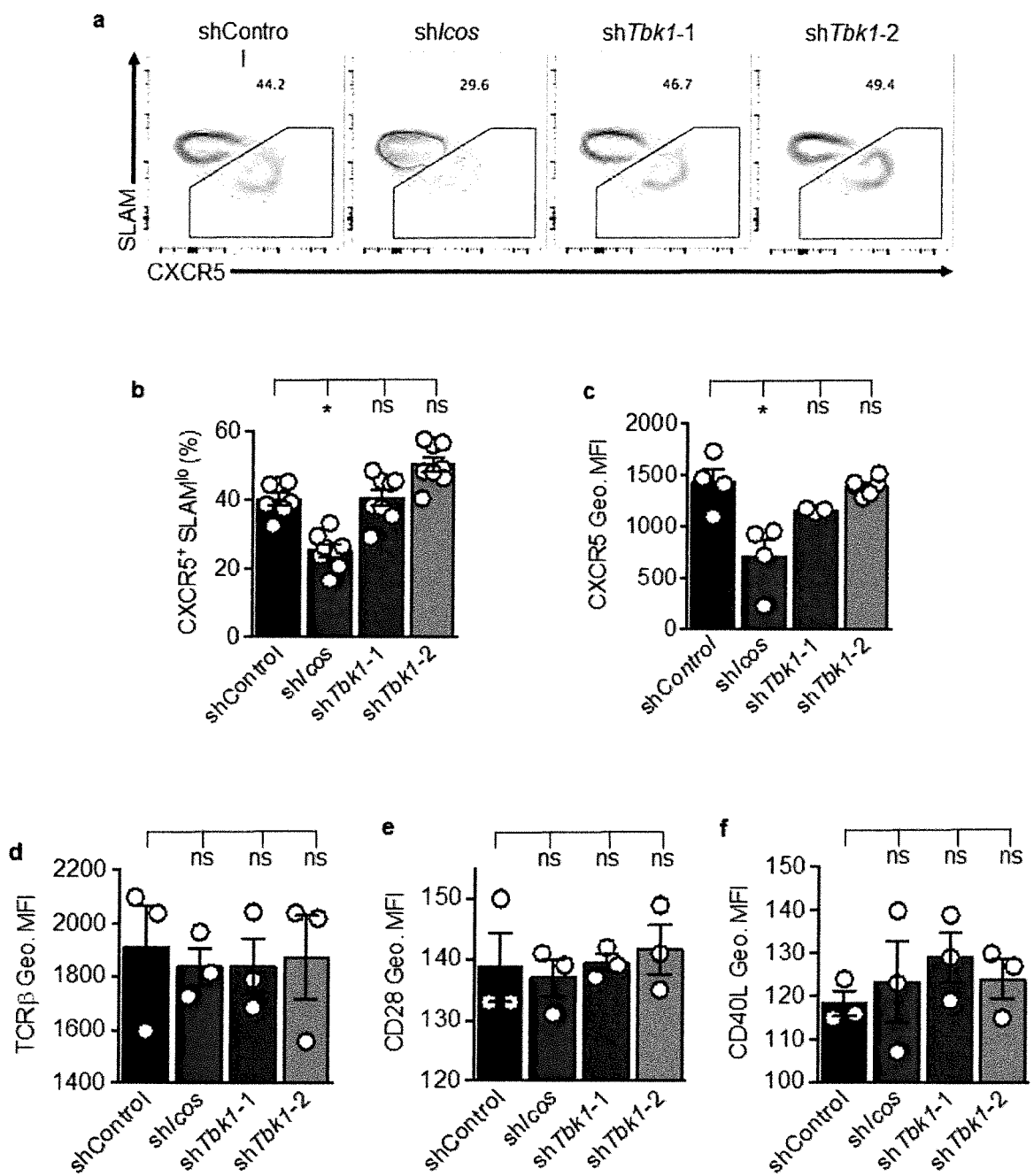
FIG. 13. TBK1 is dispensable for nascent Tfh differentiation. Adoptive transfer of shRNA-transduced SMARTA CD4+ T cells and LCMV infection were performed as in FIG. 5. (a) CXCR5+SLAM$^{lo}$ Tfh cells were analyzed 3 d later by FACS, with cumulative data from at least two independent experiments shown in (b). (c-f) Geometric mean fluorescent intensity of CXCR5 (c), TCRb chain (d), CD28 (e) and CD4OL (f) protein expression in CD4+ Ametrine+ T cells. Each data point represents a single mouse. Shown are mean±SEM. Comparative analyses of all groups were not statistically significant in (d-e). *P<0.01; ANOVA with post-hoc Tukey's corrections.

To rule out other potential Bcl6-independent mechanisms, we examined whether other markers of nascent Tfh cells are affected in the absence of the IProx motif. Down-regulation of IL2Rα or CD25 is an additional characteristic of early Tfh programming[9]. The CXCR5+CD25$^{lo}$ nascent Tfh population was comparable between icos$^{-/-}$ SMARTA CD4+ T cells reconstituted with VVT ICOS or the mlProx ICOS (FIGS. 4d & 4e). However, mice receiving the Icos$^{-/-}$ SMARTA CD4+ T cells reconstituted with the YF ICOS mutant had reduced nascent Tfh cells identified by CXCR5+Bcl6+or CXCR5+CD25$^{lo}$ phenotyping (FIGS. 4d & 4e) and also expressed lower levels of Bcl6 (FIG. 4c). Furthermore, we performed immunofluorescence histology enumerating the transduced CD45.1+ SMARTA T cells in B cell follicles at this early stage of the adaptive immune response. There was no significant difference between Icos$^{-/-}$ SMARTA CD4+ T cells reconstituted with WT ICOS or mlProx ICOS in B cell follicles (FIG. 4f), consistent with nascent Tfh differentiation and migration being independent of the ICOS-TBK1 pathway. Additionally, the CXCR5+PD1$^{hi}$ GC Tfh population was significantly abated in Icos$^{-/-}$ SMARTA CD4+ T cells reconstituted with mIProx as early as 5 days post-infection (FIG. 12). Thus, nascent Tfh differentiation occurs in the absence of the IProx motif. However, the subsequent maturation of Tfh cells is blocked in the absence of this ICOS-mediated pathway. Taken together, these results shows that the ICOS-PI3K pathway regulates the very early stage of Tfh polarization, whereas the signaling emanating from the IProx motif is critically required for the progression from nascent Tfh to GC Tfh cells.

TBK1 is dispensable for the development of nascent Tfh cells. ICOS provides a crucial costimulatory signal to induce the early programming of Tfh cells. To further dissect the role of TBK1 in Tfh development, we tracked the development of the nascent Tfh cell population in TBK1-depleted, Ag-specific T cells at an earlier time point, i.e. 3-days post-infection.

Figure 5:
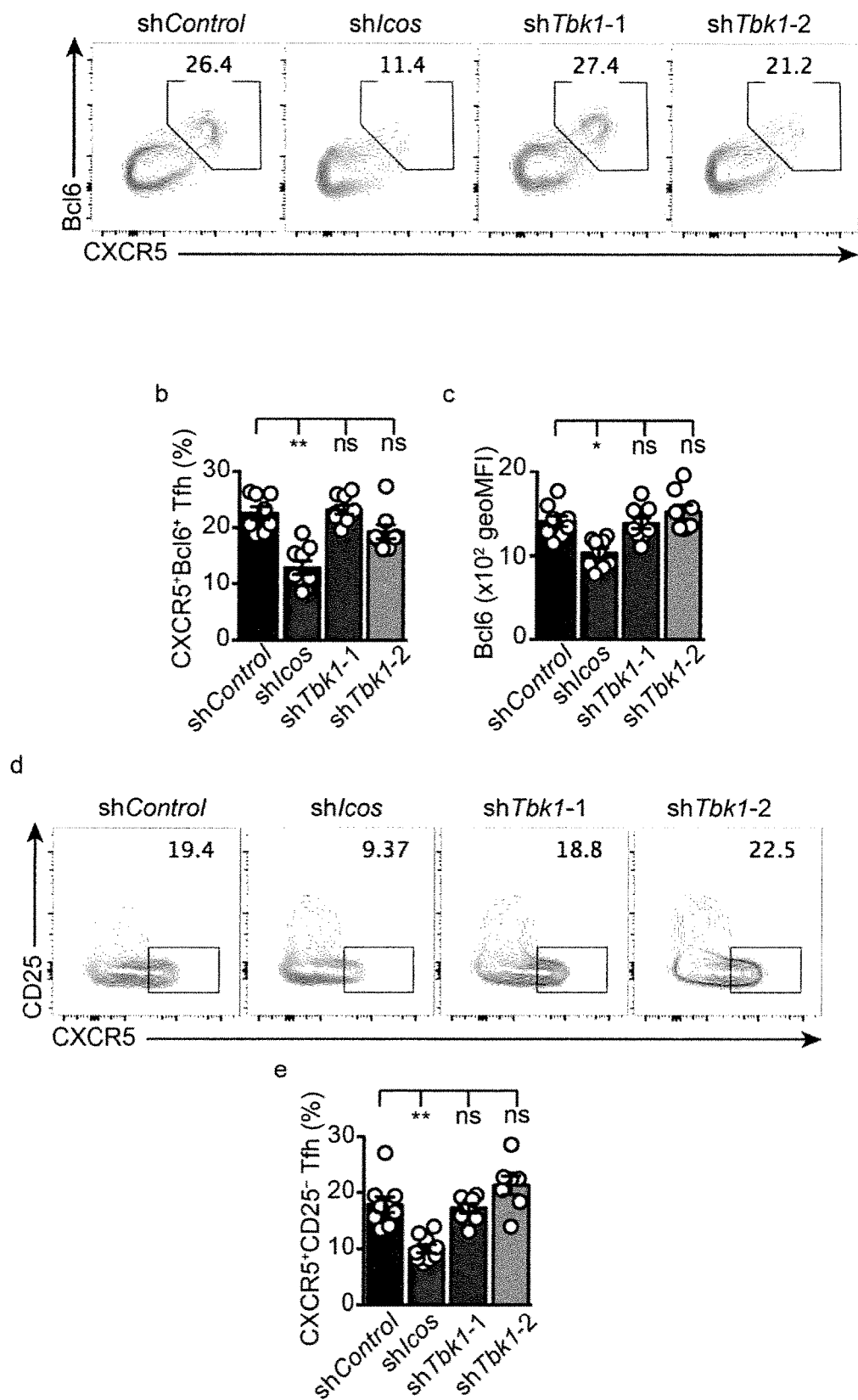
FIG. 5. TBK1 is dispensable for nascent Tfh differentiation. Adoptive transfer of shRNA-transduced SMARTA CD4+ T cells and LCMV infection were performed as in FIG. 3. CXCR5+Bcl6+ Tfh cells (a, b) or CXCR5+CD25$^{lo}$ Tfh cells (d, e) were analyzed 3 d later by FACS (a, e), with cumulative data from three two independent experiments shown in (b, d). (c) Mean fluorescent intensity of Bcl6 protein expression in sorted CD4-EGFP+ T cells. Each data point represents a single mouse. Shown are mean±SEM. *P<0.01; P<0.001; *P<0.0001; ns: not significant; ANOVA with post-hoc Tukey's corrections.

Knockdown of Icos, used as a positive control, in SMARTA CD4+ T cells significantly impeded the differentiation of nascent Tfh cells that co-express high levels of CXCR5 and Bcl6 (FIGS. 5a & 5b). However, the OXOR5+ Bcl6+ Tfh cell population was comparable in cells, in which the expression of the control gene or Tbk1 was knocked down (FIGS. 5a & 5b). Commensurate with this, there was no significant difference in the expression level of Bcl6 protein between the two groups (FIG. 5c). Additionally, the CXCR5+SLAM$^{lo}$ and CXCR5+CD25-nascent Tfh cells were significantly diminished with the depletion of ICOS, but not by TBK1 depletion (FIG. 5c-5g). We ascertained that the in vivo knockdown efficiency of Icos and Tbk1 mRNA 3 days post-infection was 88% and 93%, respectively (data not shown). In agreement with the reconstitution data (FIG. 4), knockdown of TBK1 in SMARTA CD4+ T cells did not interfere with the early differentiation of nascent Tfh cells, indicating that signals mediated by TBK1 binding to the IProx motif license nascent Tfh cells to enter the GC phase of Tfh development.

Example 10: Comparison of the ICOS-PI3K and ICOS-TBK1 Pathways

Figure 6:
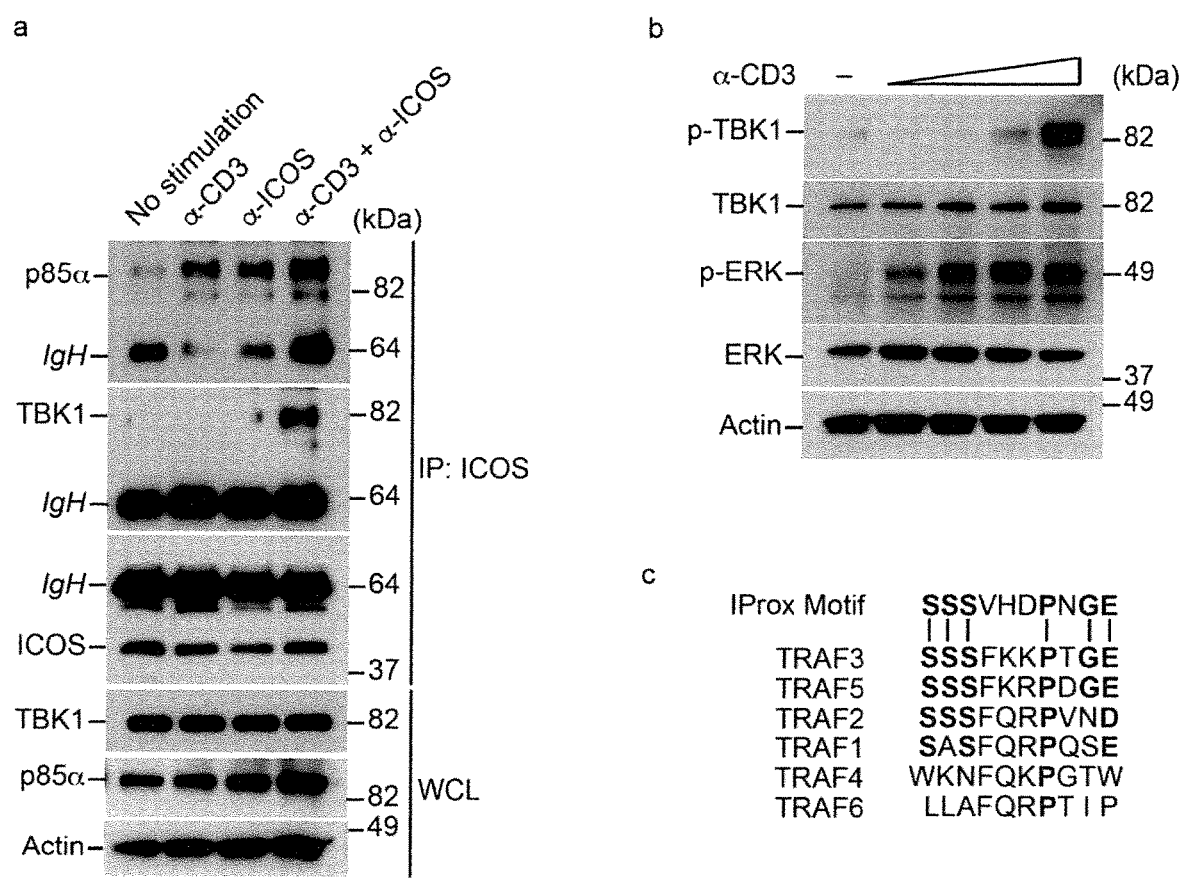
FIG. 6. Molecular basis of ICOS-TBK1 interaction. (a) In vitro activated primary mouse CD4+ T cells were left unstimulated or stimulated with cross-linked anti-CD3 mAb alone, anti-ICOS alone, or a combination of both mAbs. ICOS IPs or WCL were immunoblotted with the indicated Abs. (b) In vitro activated primary mouse CD4+ T cells were left unstimulated (-) or stimulated with increasing concentration of anti-CD3 mAb ($10^{-2}$, $10^{-1}$, $10^0$ and 101 μg/ml) plus anti-ICOS (5 μg/ml) for 5 minutes. WCL were immunoblotted with the indicated Abs. ERK phosphorylation (p-ERK) was used as a surrogate marker for T cell activation. (c) Alignment of the motif shared between the IProx motif and TRAF proteins. (d, e) Mapping of the TBK1-binding motif in TRAF3 and TRAF2. Human HEK293T cells were transfected with FLAG-tagged WT or mutated TRAF2 (d) or TRAF3 (e). Anti-FLAG IPs, IPs, or WCL were immunoblotted with the indicated Abs. Shown are representative of three experiments.
Figure 6:
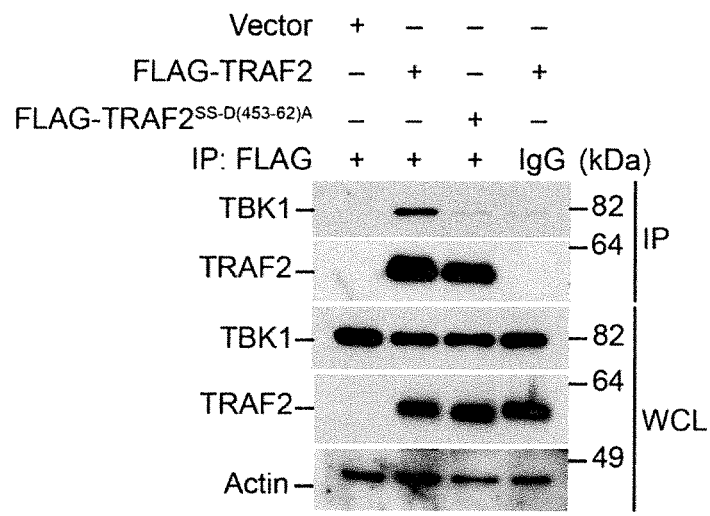
Figure 6:
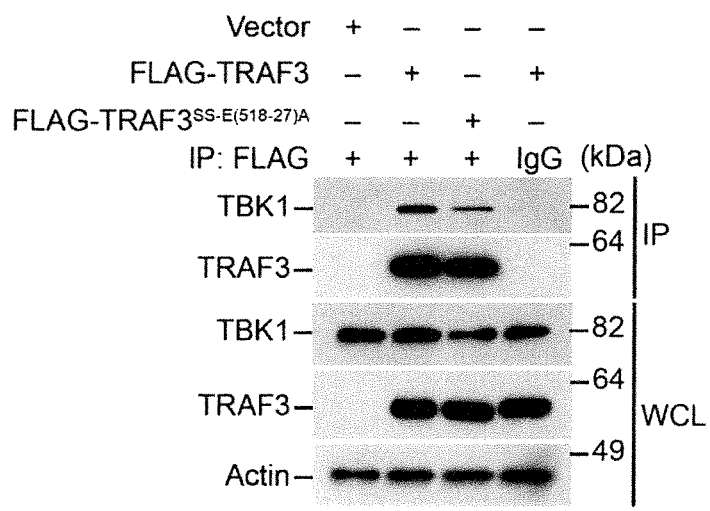
Figure 7:
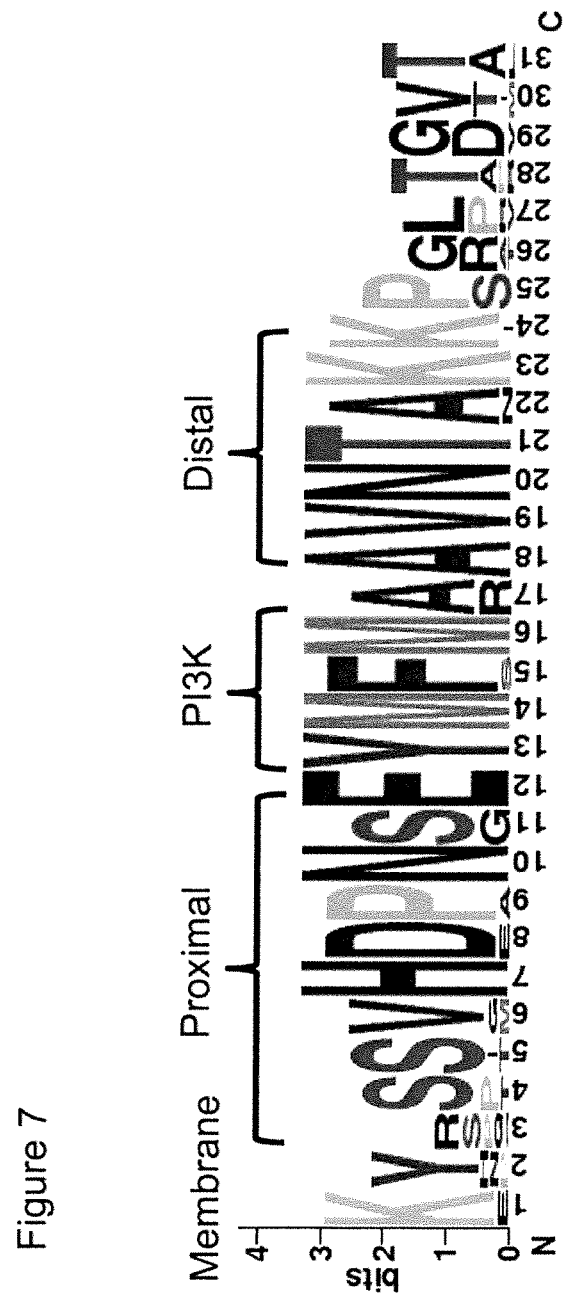
FIG. 7 Evolutionary conservation of the proximal motif, PI3K binding YxxM motif and distal motif in the cytoplasmic tail of ICOS. Amino acid sequences of putative ICOS orthologs from the indicated organisms were aligned with human ICOS.

Because the ICOS-PI3K and ICOS-TBK1 pathways exhibit distinctive behavior with regard to the priming and GC stages of Tfh development, we hypothesized that the two pathways are activated by different stimulating signals. To investigate this hypothesis, we stimulated in vitro activated CD4+ T cells in the presence of anti-CD3 mAb alone, anti-ICOS mAb alone, or the combination of both cross-linked mAbs, to mimic TCR signaling, ICOS-ICOSL signaling, or the simultaneous activation of both signals, respectively. We then analyzed the association of ICOS with either p85α or TBK1 in the absence or presence of these stimulatory conditions. In the absence of stimulation, ICOS did not co-IP with p85a, but the ICOS-p85α association was rapidly induced by all three forms of stimulation (FIG. 6a). Strikingly and in sharp contrast, TBK1 co-immunoprecipitated with ICOS only when the cells were costimulated with anti-CD3 and anti-ICOS mAbs, but not under conditions of no stimulus or when single stimuli were applied (FIG. 6a). These results indicate that combined signaling from the TCR and ICOS is required to induce ICOS-TBK1 association and the resulting signaling pathway. Additionally, in in vitro activated CD4+ T cells, the phosphorylation of TBK1 was induced only in the presence of a strong anti-CD3 plus anti-ICOS signal (FIG. 6b), supporting the notion that strong TCR stimulation favors a TBK1-dependent signal to drive the differentiation of GC Tfh cells38. Thus, the requirement for activation of the ICOS-TBK1 signaling is more stringent than that for the ICOS-PI3K pathway in that it requires two simultaneous signals provided by the strong cognate interaction between T cells and APCs.

Figure 14:
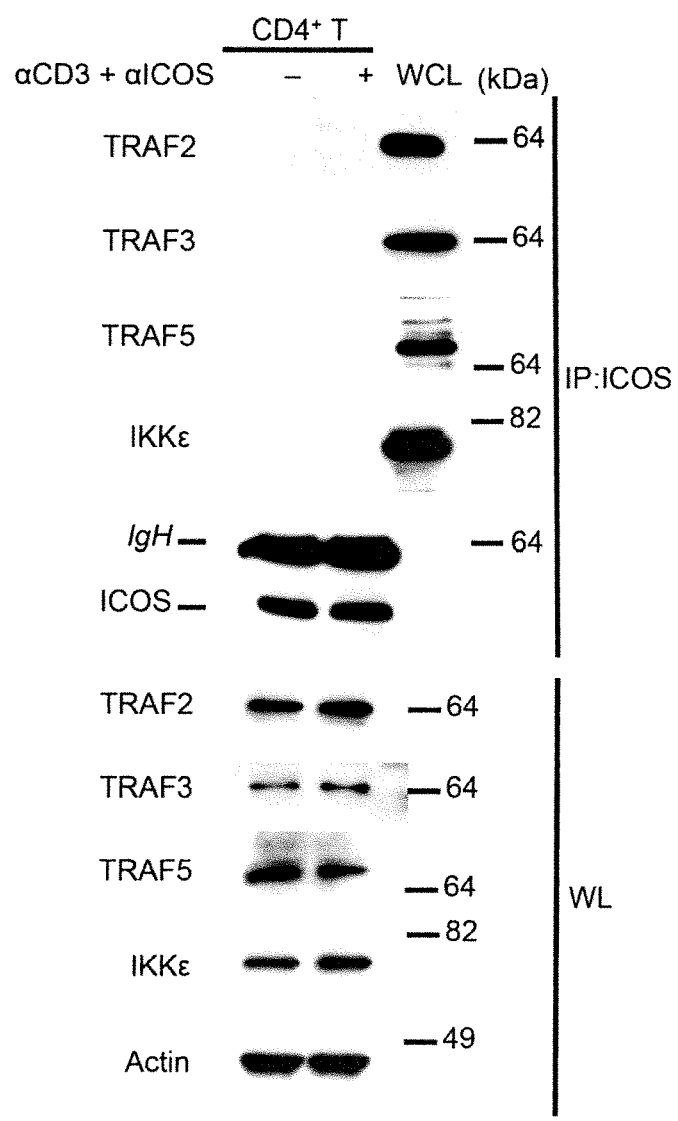
FIG. 14. ICOS signalosome is independent of TRAF molecules and IKKE. ICOS immunoprecipitates (I Ps) were prepared from mouse primary CD4$^+$ T cells activated in vitro with anti-CD3 plus -CD28 mAbs and rested in IL-2, followed by restimulation with anti-CD3 plus -ICOS mAbs. Ilps or whole cell lysates (WCL) were immunoblotted with the indicated Abs. 5% WCL was used as input to control for IP Western.
Figure 15:
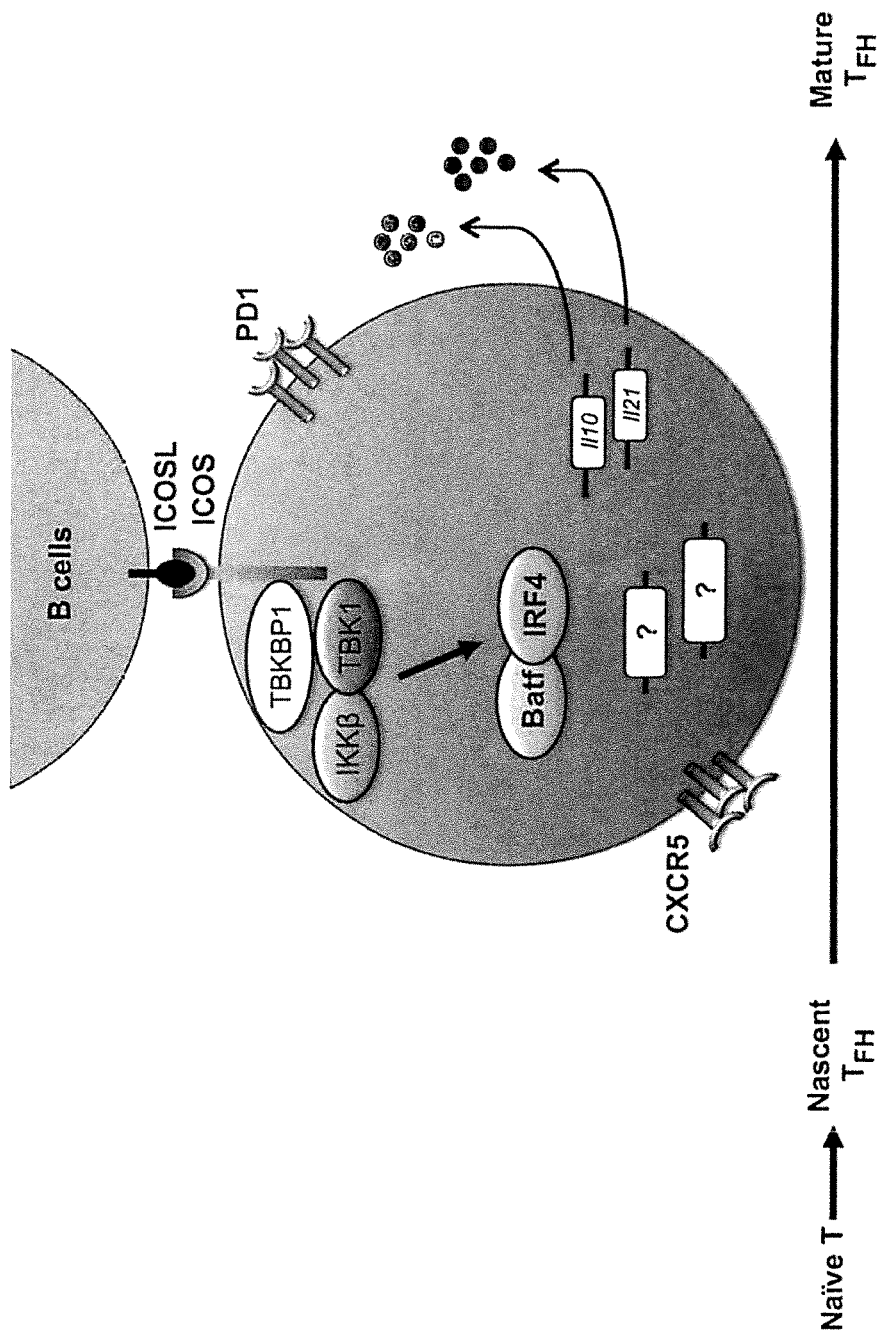
FIG. 15. The working model.

Example 11: The ICOS-TBK1 Pathway is Mechanistically Distinct from the TNFR or TLR Pathways TBK1 transduces pivotal activating signals from the membrane-associated TNFR and TLR molecules in innate immune cells (Akira S and Takeda K. Nat Rev Immunol 2004, 4(7):499-511). TRAF proteins, particularly TRAF2, TRAF3 and TRAF5, but not TRAF6, have been shown to physically interact with TBK1 to mediate the downstream effector functions (Hacker H, et al. Nature 2006, 439(7073): 204-207 and Sato S, et al., J Immunol 2003, 171(8): 4304-4310, the entire contents of each are hereby incorporated by reference) although the TBK1-binding motif in TRAFs has not been defined. We were not able to detect TRAF2, TRAF3 or TRAF5 in ICOS IP from T cells, consistent with the fact that ICOS does not belong to the TNFR or TLR superfamilies (FIG. 14). Additionally, IKKε, which forms a complex with TBK1 in innate immune cells (Sharma S et al., Science 2003, 300(5622): 1148-1151 and Fitzgerald K A, et al. Nat Immunol 2003, 4(5): 491-496), was also absent from the immunoprecipitated ICOS signalosome (FIG. 14), reinforcing the notion that the ICOS-TBK1 pathway is mechanistically distinct from the TNFR or TLR pathways. We speculated that, instead of recruiting TBK1 via TRAFs, perhaps ICOS itself might contain a motif shared with TBK1-binding TRAF proteins. To test this idea, we performed a BLASTp search analysis by comparing the human protein sequences between the ICOS cytoplasmic tail and full-length TRAF2 and TRAF3. To our surprise, this analysis revealed a significant homology between the IProx motif and a motif known as the "serine tongs" of TRAF2 and TRAF3 (FIG. 6b). More importantly, the homology extends beyond the triple serine residues, encompassing a proline residue and a negatively charged aspartic or glutamic acid at the C-terminus. This region is found in TRAF2, TRAF3 and TRAF5, which are the known TRAF to bind TBK1, but not in TRAF4 and TRAF6 (FIG. 6b). Additionally, the extended "serine tongs" motif is also well conserved among TRAF2 and TRAF3 orthologs throughout evolution from primitive multicellular organisms, including sponges and Cnidarians, to primates (Tables 3 and 4).

TABLE 3

Conservation of TRAF2 Serine Tongs Across Species

| Species | Sequence | SEQ ID NO | NCBI Accession | SEQ ID No |
|---|---|---|---|---|
| Homo sapiens | SSSFQRPVND | 66 | ADQ89802 | 72 |
| Mus musculus | SSSFQRPVSD | 67 | AAF59928 | 73 |
| Gallus gallus | SSSFQRPVTE | 68 | CDZ92726 | 74 |
| Dario rerio (Zebrafish) | SSSFQRPVSD | 69 | XP_005172003 | 75 |
| Branchiostoma floridae (Lancelet) | SSSFKRPTSD | 70 | XP_002592506 | 76 |

TABLE 3-continued

Conservation of TRAF2
Serine Tongs Across Species

| Species | Sequence | SEQ ID NO | NCBI Accession | SEQ ID No |
|---|---|---|---|---|
| Amphimedon queenslandica (Sponge) | SSSFQRPKSD | 71 | XP_003390171 | 77 |

Conserved residues in bold.

TABLE 4

Conservation of TRAF3 Serine Tongs Across Species

| Species | Sequence | SEQ ID NO | NCBI Accession | SEQ ID NO |
|---|---|---|---|---|
| Homo sapiens | SSSFKKPTGE | 78 | NP_663777 | 86 |
| Mus musculus | SSSFKKPTGE | 79 | NP_035762 | 87 |
| Gallus gallus | SSSFKKPTGE | 80 | XP_004936405 | 88 |
| Dario rerio (Zebrafish) | SSSFRRPTGE | 81 | NP_001003513 | 89 |
| Eptatretus burgeri (Hagfish) | SSSFKRPTSE | 82 | BAG85182 | 90 |
| Pinctada fucata (Molluscs) | SSSFRKPTTE | 83 | AFL03408 | 91 |
| Strongylocentrotus purpuratus (Sea urchin) | SSSFQRPTSN | 84 | XP_783477 | 92 |
| Nematostella vectensis (Starlet sea anemone) | SSSFKRPTSN | 85 | XP_001641527 | 93 |

Conserved residues in bold.

Example 12: Consensus Sequences Between ICOS and TRAF Proteins

The homology between ICOS and TRAF proteins suggested that the shared motif is a consensus TBK1-binding motif. To validate this notion, we substituted the corresponding region in TRAF2 (amino acid 453-462) and TRAF3 (amino acid residues 518-527), with a string of 10 alanine residues and examined the interaction of these TRAF mutants with TBK1. While TBK1 interacted strongly with WT TRAF2 (FIG. 6d) and TRAF3 (FIG. 6e), its association with the corresponding mutated TRAFs was strongly reduced, similar to the defective association of TBK1 with the mIProx (FIG. 2b). Therefore, these results support the notion that the IProx motif by itself acts as a direct TBK1-binding site, thus bypassing the requirement of TRAF molecules as intermediary partners, and foster the commitment of nascent Tfh cells to enter the GC phase of development.

Analysis of Results

Specifically, the inventors have: i) identified a previously unknown, evolutionarily conserved membrane-proximal ICOS, IProx, motif that is required for Tfh development and function; ii) identified TBK1 as an activation-induced interacting partner of this motif; iii) demonstrated that the recruitment of TBK1 is required for the development of fully mature GC Tfh cells while being dispensable for the differentiation of early, nascent Tfh cells; and iv) identified a putative TBK1-binding consensus sequence that is shared between the ICOS cytoplasmic domain and TRAF2/3 molecules.

Since the initial demonstration of the importance of the TBK1-IKKE complex in mediating the production of type I interferon (Sharma et al., and Fitzgerald et al., supra), much work has been devoted to the understanding of the role of this complex (which is coupled to TRAF2/3 proteins) in innate immune cells. However, over time it has become clear that TBK1 plays a role in non-immune cells (Hemmi H, et al. J Exp Med 2004, 199(12): 1641-1650 and Bonnard M, et al. EMBO J 2000, 19(18): 4976-4985) as well as in immune responses to DNA vaccines, owing to defects in both the innate and adaptive arms of the immune system (Ishii K J, et al. Nature 2008, 451(7179): 725-729). Furthermore, loss-of-function mutations of the human TBK1 gene have been identified in patients with childhood herpes simplex virus-1 encephalitis (Herman M, et al. J Exp Med 2012, 209(9): 1567-1582). Surprisingly, responses to other viruses remained intact in these patients, despite the fact that TBK1 is the dominant signal transducer for all type I interferon-inducing pathways. However, these studies have not defined the particular immune cell type that is affected by TBK1 deletion or mutations. TBK1 has also been shown to play a critical role in B cell responses, as B cell-specific Tbk1 deletion in mice leads to hyper-production of IgA and autoantibodies, (Jin J, et al. *Nat Immunol* 2012, 13(11): 1101-1109) reflecting a function of TBK1 in B cell immunity. Our findings pinpoint a key mechanism for TBK1 in T cell immunity.

Using a yeast-two-hybrid screen, TBK1 was found to interact with TRAF2 and activate NF-κB signaling in response to TNFα, IL-1β or CD4OL stimulation (Pomerantz J L and Baltimore D., EMBO J 1999, 18(23): 6694-6704). Subsequently, TRAF3, but not TRAF6, was shown to bind TBK1 and to function as a molecular link between Toll-like receptors and TBK1 (Hacker H, et al., supra and Oganesyan G, et al. Nature 2006, 439(7073): 208-211). However, the actual motif in TRAF2 and TRAF3 required for binding to TBK1 has not been definitively mapped. Here, we mapped the TBK1-binding site in the ICOS cytoplasmic domain to the IProx motif and found that this motif is also present in several TBK1-binding TRAF proteins. Moreover, mutation of this motif abolished the interaction of both TRAF proteins with TBK1. This TRAF motif, termed a "serine tongs" motif, was initially proposed to function as a TRAF2 binding site for the cytoplasmic domain of CD40 (McWhirter S M, et al., Proc Natl Acad Sci USA 1999, 96(15): 8408-8413) but subsequent mutagenesis and biochemical analyses failed to corroborate this notion (Li C, et al. J Biol Chem 2003, 278(50): 50523-50529). Thus, the role of the highly conserved "serine tongs" motif in TRAF2 and TRAF3 has remained controversial. Our findings strongly suggest that the proximal motif which is evolutionarily conserved in ICOS proteins, represents the canonical TBK1-binding sequence.

Initial signals required for the polarization of nascent Tfh cells include CD28-B7 and ICOS-ICOSL receptor-ligand pair interactions that form between naïve T cells and DC during the priming phase. As mentioned above, previous studies have circumstantially linked these early events of Tfh differentiation to the PI3K-mediated ICOS pathway (Choi et al., supra and Gigoux M, et al. Proc Natl Acad Sci USA 2009, 106(48): 20371-20376). Moreover, ICOS stimulation induces the interaction of the PI3K p85α subunit with intracellular osteopontin, resulting in the latter protein interacting with Bcl6 and protecting it from degradation. Thus, ablation of intracellular osteopontin led to the failure of Bcl6 maintenance as early as three days post protein immunization (Leavenworth J W, et al., *Nat Immunol* 2015, 16(1): 96-106). Our finding that mutation of the PI3K-binding site in ICOS abolished the polarization of nascent Tfh cells and significantly compromised early Bcl6 protein expression is fully consistent with the above studies.

The inventors have discovered a new molecular pathway, i.e. the TBK1-dependent signaling pathway mediated by the, ICOS proximal motif, which functions to drive the differentiation of T cells from the nascent Tfh stage to the mature, fully functional GC Tfh stage. Further the inventors have discovered methods for modifying the components of this pathway to achieve therapeutic results. Nascent Tfh cells are the precursors of bona fide GC Tfh cells. Only upon contact with cognate B cells do these nascent Tfh cells receive additional maturation signals to become CXCR5$^+$PD1$^{hi}$ GC Tfh cells. GC Tfh cells fail to develop in the absence of B cells (Haynes N M, et al., *J Immunol* 2007, 179(8): 5099-5108), upon B cell-specific conditional deletion of ICOSL (Nurieva R I, et al., *Immunity* 2008, 29(1): 138-149) or following anti-ICOSL antibody blockade (Choi et al., supra and Akiba H, et al., *J Immunol* 2005, 175(4): 2340-2348), indicating that ICOS-ICOSL engagement mediated by cognate T-B cell interaction is essential for the continuous maturation of these interacting cells. Recent data have also shown that ICOS-driven motility, which promotes Tfh cell migration deep into the follicular parenchyma, can also be dependent on ICOS-coupled PI3K-mediated signaling triggered by ICOSL present on bystander follicular B cells, which do not present cognate antigen (Xu H, et al., *Nature* 2013, 496(7446): 523-527).

The present findings demonstrating a role for distinct ICOS-linked signaling modules in full Tfh differentiation can potentially unify these seemingly opposing observations, since we have demonstrated that while either TCR or ICOS stimulation alone can induce the association of ICOS with PI3K, a combination of both signals was required to recruit and activate TBK1. The polarization of nascent Tfh cells is independent of ICOS-TBK1 signaling. Therefore, it could be argued that upon encountering B cells expressing cognate peptide-WIC and ICOSL, ICOS-TBK1 signaling, possibly in conjunction with ICOS-PI3K pathway, induces the maturation process of nascent Tfh cells. Upon this differentiation step, mature Tfh cells could migrate into the follicular parenchyma through serial interactions with bystander follicular B cells in a manner dependent on the ICOS, ICOSL interaction (Kerfoot et al., supra) but independent of TCR signals, which would be sufficient to trigger the ICOS-PI3K signaling pathway. Consistently, we found that there was no defect in early Tfh migration in the absence of ICOS-TBK1 pathway, but the nascent immature Tfh cells infiltrated into B cell follicles are incapable of supporting B cell maturation and germinal center development. Therefore, there is a bifurcation in functionality between the IProx-motif dependent ICOS-TBK1 pathway and the ICOS-PI3K pathway. Our data demonstrate that both pathways are essential, independently, for Tfh differentiation, germinal center development and class-switched IgG response.

Ab production is a double-edged process. CD4$^+$ Tfh cells are endowed with the ability to positively support the maturation of B cells producing Abs with the highest affinity for the immunizing antigen, while counter-selecting for B cells expressing self-recognizing Abs. Here, we showed that ICOS regulates, in addition to PI3K signaling, TBK1-dependent signaling pathway, with both pathways acting together to promote the sequential development of Tfh cells. Furthermore, the studies presented herein demonstrated that the ICOS-TBK1 interaction is expressly required to allow the commitment to become fully functional GC Tfh cells, which represent the ultimate regulators of Ab-producing B cells. Therefore, the studies provided herein expand the essential roles of TBK1 to antigen-specific CD4$^+$ T cell immunity. Strategic manipulations of these ICOS-dependent pathways could lead to treatments for immunomodulatory diseases, neurodegenerative diseases, cancer and metabolic diseases, better vaccine design, autoimmune diseases, and treatment of infectious diseases.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of modulating the interaction between ICOS and TBK1 in a cell selected from the group of a T-cell, a B-cell, or a Tfh cell comprising contacting the cell with an agonist or antagonist of ICOS-mediated or TBK1-mediated immune signaling wherein the agonist or antagonist is a peptide consisting of any one of SEQ ID NOs 24 or 25.

2. A method of modulating the interaction between TBKBP1, IKKβ and IRF4 and BATF in a cell by modulating the interaction between ICOS and TBK1 comprising contacting the cell with a peptide consisting of SEQ ID NO 24.

3. The method of claim 1, wherein the peptide consists of SEQ ID NO 24.

4. The method of claim 1, wherein the cell is a T cell or a Tfh cell.

5. A method of modulating the interaction between ICOS and TBK1 in a cell comprising contacting the cell with a peptide consisting SEQ ID NO 24.

6. The method of claim 5, wherein the cell is selected from group of a T-cell, a B-cell, or a Tfh cell.

* * * * *